US008361053B2

(12) United States Patent
Gonnelli et al.

(10) Patent No.: US 8,361,053 B2
(45) Date of Patent: Jan. 29, 2013

(54) MULTI-CARTRIDGE FLUID DELIVERY DEVICE

(75) Inventors: Robert R. Gonnelli, Mahwah, NJ (US); Steven F. Levesque, Hanson, MA (US); Ronald V. Nardi, Mahwah, NJ (US)

(73) Assignee: Valeritas, Inc., Bridgewater, NJ (US)

( * ) Notice: Subject to any disclaimer, the term of this patent is extended or adjusted under 35 U.S.C. 154(b) by 0 days.

(21) Appl. No.: 13/013,379

(22) Filed: Jan. 25, 2011

(65) Prior Publication Data

US 2011/0137287 A1 Jun. 9, 2011

Related U.S. Application Data

(63) Continuation of application No. 12/295,173, filed as application No. PCT/US2007/065363 on Mar. 28, 2007, now Pat. No. 7,914,499.

(60) Provisional application No. 60/787,616, filed on Mar. 30, 2006.

(51) Int. Cl.
*A61M 31/00* (2006.01)

(52) U.S. Cl. ...................................................... 604/506

(58) Field of Classification Search ...................... 604/19
See application file for complete search history.

(56) References Cited

U.S. PATENT DOCUMENTS

| 2,828,743 A | 4/1858 | Ashkenaz et al. |
| 2,605,765 A | 8/1952 | Kollsman |
| 2,702,547 A | 2/1955 | Glass |
| 3,055,362 A | 9/1962 | Uytenbogaart |
| 3,187,749 A | 6/1965 | Sarnoff |
| 3,731,681 A | 5/1973 | Blackshear et al. |
| 3,886,938 A | 6/1975 | Szabo et al. |
| 3,963,151 A | 6/1976 | North, Jr. |
| 4,042,153 A | 8/1977 | Callahan et al. |
| 4,065,230 A | 12/1977 | Gezari |
| 4,085,749 A | 4/1978 | Chambron |
| 4,150,672 A | 4/1979 | Whitney et al. |
| 4,190,048 A | 2/1980 | Sampson |
| 4,193,397 A | 3/1980 | Tucker et al. |
| 4,202,333 A | 5/1980 | Thill et al. |
| 4,209,014 A | 6/1980 | Sefton |
| 4,258,711 A | 3/1981 | Tucker et al. |
| 4,265,241 A | 5/1981 | Portner et al. |
| 4,267,836 A | 5/1981 | Whitney et al. |
| 4,298,000 A | 11/1981 | Thill et al. |

(Continued)

FOREIGN PATENT DOCUMENTS

| DE | 3634725 A1 | 4/1998 |
| DE | 3739657 A1 | 5/1998 |

(Continued)

OTHER PUBLICATIONS

Notification of Reasons for Rejection in Japanese Patent Application No. 2009-503245.

(Continued)

*Primary Examiner* — Nicholas Lucchesi
*Assistant Examiner* — Jason Flick
(74) *Attorney, Agent, or Firm* — Morgan, Lewis & Bockius LLP

(57) ABSTRACT

A fluid delivery device for administering a first medicament and a second medicament includes a first fluid reservoir configured to contain the first medicament and a second fluid reservoir configured to contain the second medicament. The fluid delivery device may include one or more basal drive mechanisms to provide a basal delivery of one or more of the first and second medicaments. The fluid delivery device may further include one or more bolus drive mechanisms to provide a bolus delivery of one or more of the first and second medicaments.

22 Claims, 20 Drawing Sheets

U.S. PATENT DOCUMENTS

| | | |
|---|---|---|
| 4,313,439 A | 2/1982 | Babb et al. |
| 4,340,048 A | 7/1982 | Eckenhoff |
| 4,351,335 A | 9/1982 | Whitney et al. |
| 4,360,019 A | 11/1982 | Portner et al. |
| 4,398,908 A | 8/1983 | Siposs |
| 4,411,651 A | 10/1983 | Schulman |
| 4,430,079 A | 2/1984 | Thill et al. |
| 4,431,426 A | 2/1984 | Groshong et al. |
| 4,437,859 A | 3/1984 | Whitehouse et al. |
| 4,443,218 A | 4/1984 | DeCant, Jr. et al. |
| 4,496,343 A | 1/1985 | Prosl et al. |
| 4,525,165 A | 6/1985 | Fischell |
| 4,529,401 A | 7/1985 | Leslie et al. |
| 4,548,607 A | 10/1985 | Harris |
| 4,552,561 A | 11/1985 | Eckenhoff et al. |
| 4,559,038 A | 12/1985 | Berg et al. |
| 4,561,856 A | 12/1985 | Cochran |
| 4,565,542 A | 1/1986 | Berg |
| 4,568,335 A | 2/1986 | Updike et al. |
| 4,583,973 A | 4/1986 | Humphrey et al. |
| 4,596,575 A | 6/1986 | Rosenberg et al. |
| 4,601,707 A | 7/1986 | Albisser et al. |
| 4,627,839 A | 12/1986 | Young |
| 4,648,872 A | 3/1987 | Kamen |
| 4,650,469 A | 3/1987 | Berg et al. |
| 4,685,902 A | 8/1987 | Edwards et al. |
| 4,699,615 A | 10/1987 | Fischell et al. |
| 4,715,852 A | 12/1987 | Reinicke et al. |
| 4,718,893 A | 1/1988 | Dorman et al. |
| 4,723,947 A | 2/1988 | Konopka |
| 4,731,058 A | 3/1988 | Doan |
| 4,734,092 A | 3/1988 | Millerd |
| 4,741,736 A | 5/1988 | Brown |
| 4,744,786 A | 5/1988 | Hooven |
| 4,747,824 A | 5/1988 | Spinello |
| 4,749,109 A | 6/1988 | Kamen |
| 4,755,172 A | 7/1988 | Baldwin |
| 4,772,263 A | 9/1988 | Dorman et al. |
| 4,772,273 A | 9/1988 | Alchas |
| 4,781,688 A | 11/1988 | Thoma et al. |
| 4,784,576 A | 11/1988 | Bloom et al. |
| 4,784,577 A | 11/1988 | Ritson et al. |
| 4,790,829 A | 12/1988 | Bowden et al. |
| 4,808,161 A | 2/1989 | Kamen |
| 4,808,167 A | 2/1989 | Mann et al. |
| 4,813,951 A | 3/1989 | Cannon et al. |
| 4,816,019 A | 3/1989 | Kamen |
| 4,818,186 A | 4/1989 | Pastrone et al. |
| 4,822,339 A | 4/1989 | Tran |
| 4,826,482 A | 5/1989 | Kamen |
| 4,834,704 A | 5/1989 | Reinicke |
| 4,838,857 A | 6/1989 | Strowe et al. |
| 4,842,584 A | 6/1989 | Pastrone |
| 4,846,806 A | 7/1989 | Wigness et al. |
| 4,856,340 A | 8/1989 | Garrison |
| 4,861,341 A | 8/1989 | Woodburn |
| 4,874,386 A | 10/1989 | O'Boyle |
| 4,886,499 A | 12/1989 | Cirelli et al. |
| 4,894,054 A | 1/1990 | Miskinyar |
| 4,900,305 A | 2/1990 | Smith et al. |
| 4,902,278 A | 2/1990 | Maget et al. |
| 4,919,134 A | 4/1990 | Streeter |
| 4,925,444 A | 5/1990 | Orkin et al. |
| 4,927,411 A | 5/1990 | Pastrone et al. |
| 4,931,050 A | 6/1990 | Idriss |
| 4,952,210 A | 8/1990 | Alchas |
| 4,971,900 A | 11/1990 | Ahnell et al. |
| 4,976,162 A | 12/1990 | Kamen |
| 4,976,696 A | 12/1990 | Sanderson et al. |
| 4,998,926 A | 3/1991 | Alchas |
| 5,000,994 A | 3/1991 | Romberg et al. |
| 5,009,641 A | 4/1991 | Gorton |
| 5,024,664 A | 6/1991 | Mitchell |
| 5,037,396 A | 8/1991 | Streeter |
| 5,039,279 A | 8/1991 | Natwick et al. |
| 5,041,094 A | 8/1991 | Perego et al. |
| 5,045,064 A | 9/1991 | Idriss |
| 5,053,031 A | 10/1991 | Borsanyi |
| 5,055,001 A | 10/1991 | Natwick et al. |
| 5,059,174 A | 10/1991 | Vaillancourt |
| 5,062,774 A | 11/1991 | Kramer et al. |
| 5,088,515 A | 2/1992 | Kamen |
| 5,090,963 A | 2/1992 | Gross et al. |
| 5,098,262 A | 3/1992 | Wecker et al. |
| 5,100,380 A | 3/1992 | Epstein et al. |
| 5,106,374 A | 4/1992 | Apperson et al. |
| 5,108,367 A | 4/1992 | Epstein et al. |
| 5,135,498 A | 8/1992 | Kam et al. |
| 5,135,500 A | 8/1992 | Zdeb |
| 5,144,515 A | 9/1992 | Frauhauf et al. |
| 5,158,437 A | 10/1992 | Natwick et al. |
| 5,165,869 A | 11/1992 | Reynolds |
| 5,167,631 A | 12/1992 | Thompson et al. |
| 5,169,390 A | 12/1992 | Athayde et al. |
| 5,176,502 A | 1/1993 | Sanderson et al. |
| 5,176,641 A | 1/1993 | Idriss |
| 5,176,644 A | 1/1993 | Srisathapat et al. |
| 5,178,182 A | 1/1993 | Kamen |
| 5,178,609 A | 1/1993 | Ishikawa |
| 5,180,287 A | 1/1993 | Natwick et al. |
| 5,181,910 A | 1/1993 | Scanlon |
| 5,188,603 A | 2/1993 | Vaillancourt |
| 5,193,990 A | 3/1993 | Kamen et al. |
| 5,197,322 A | 3/1993 | Indravudh |
| 5,207,642 A | 5/1993 | Orkin et al. |
| 5,207,666 A | 5/1993 | Idriss et al. |
| 5,211,201 A | 5/1993 | Kamen et al. |
| 5,217,442 A | 6/1993 | Davis |
| 5,219,279 A | 6/1993 | Natwick et al. |
| 5,219,428 A | 6/1993 | Stern |
| 5,222,946 A | 6/1993 | Kamen |
| 5,232,449 A | 8/1993 | Stern et al. |
| 5,242,408 A | 9/1993 | Jhuboo et al. |
| 5,248,300 A | 9/1993 | Bryant et al. |
| 5,250,649 A | 10/1993 | Onwumere et al. |
| 5,254,096 A | 10/1993 | Rondelet et al. |
| 5,257,971 A | 11/1993 | Lord et al. |
| 5,257,987 A | 11/1993 | Athayde et al. |
| 5,259,732 A | 11/1993 | Stern |
| 5,261,884 A | 11/1993 | Stern et al. |
| 5,263,323 A | 11/1993 | Maus et al. |
| 5,281,210 A | 1/1994 | Burke et al. |
| 5,290,240 A | 3/1994 | Horres, Jr. |
| 5,295,966 A | 3/1994 | Stern et al. |
| 5,295,967 A | 3/1994 | Rondelet et al. |
| 5,300,041 A | 4/1994 | Haber et al. |
| 5,304,126 A | 4/1994 | Epstein et al. |
| 5,306,257 A | 4/1994 | Zdeb |
| 5,308,334 A | 5/1994 | Sancoff |
| 5,312,364 A | 5/1994 | Jacobs et al. |
| 5,318,540 A | 6/1994 | Athayde et al. |
| 5,319,979 A | 6/1994 | Abrahamson |
| 5,320,600 A | 6/1994 | Lambert |
| 5,322,422 A | 6/1994 | Natwick et al. |
| 5,328,459 A | 7/1994 | Laghi |
| 5,338,157 A | 8/1994 | Blomquist |
| 5,338,312 A | 8/1994 | Montgomery |
| 5,349,852 A | 9/1994 | Kamen et al. |
| 5,350,357 A | 9/1994 | Kamen et al. |
| 5,356,379 A | 10/1994 | Vaillancourt |
| 5,364,242 A | 11/1994 | Olsen |
| 5,368,562 A | 11/1994 | Blomquist et al. |
| 5,368,571 A | 11/1994 | Horres, Jr. |
| 5,370,622 A | 12/1994 | Livingston et al. |
| 5,376,070 A | 12/1994 | Purvis et al. |
| 5,389,078 A | 2/1995 | Zalesky et al. |
| 2,703,084 A | 3/1995 | Tomlinson |
| 5,396,925 A | 3/1995 | Poli |
| 5,399,166 A | 3/1995 | Laing |
| 5,399,823 A | 3/1995 | McCusker |
| 5,405,614 A | 4/1995 | D'Angelo et al. |
| 5,421,823 A | 6/1995 | Kamen et al. |
| 5,431,626 A | 7/1995 | Bryant et al. |
| 5,431,634 A | 7/1995 | Brown |
| 5,433,710 A | 7/1995 | Van Antwerp et al. |
| 5,438,510 A | 8/1995 | Bryant et al. |
| 5,445,621 A | 8/1995 | Poli et al. |

| Patent No. | Date | Inventor(s) |
|---|---|---|
| 5,447,286 A | 9/1995 | Kamen et al. |
| 5,453,099 A | 9/1995 | Lee et al. |
| 5,456,909 A | 10/1995 | Marsh, Jr. et al. |
| 5,456,940 A | 10/1995 | Funderburk |
| 5,460,618 A | 10/1995 | Harreld |
| 5,462,525 A | 10/1995 | Srisathapat et al. |
| 5,464,392 A | 11/1995 | Epstein et al. |
| 5,466,218 A | 11/1995 | Srisathapat et al. |
| 5,472,317 A | 12/1995 | Field et al. |
| 5,474,683 A | 12/1995 | Bryant et al. |
| 5,480,386 A | 1/1996 | Brohy et al. |
| 5,485,408 A | 1/1996 | Blomquist |
| 5,487,737 A | 1/1996 | Meyer et al. |
| 5,492,534 A | 2/1996 | Athayde et al. |
| 5,505,704 A | 4/1996 | Pawelka et al. |
| 5,505,706 A | 4/1996 | Maus et al. |
| 5,505,709 A | 4/1996 | Funderburk et al. |
| 5,505,713 A | 4/1996 | Van Antwerp |
| 5,507,277 A | 4/1996 | Rubsamen et al. |
| 5,514,103 A | 5/1996 | Srisathapat et al. |
| 5,515,713 A | 5/1996 | Saugues et al. |
| 5,526,844 A | 6/1996 | Kamen et al. |
| 5,527,288 A | 6/1996 | Gross et al. |
| 5,527,307 A | 6/1996 | Srisathapat et al. |
| 5,529,463 A | 6/1996 | Layer et al. |
| 5,531,697 A | 7/1996 | Olsen et al. |
| 5,531,698 A | 7/1996 | Olsen |
| 5,533,389 A | 7/1996 | Kamen et al. |
| 5,533,994 A | 7/1996 | Meyer et al. |
| 5,538,399 A | 7/1996 | Johnson |
| 5,538,511 A | 7/1996 | Van Antwerp |
| 5,540,561 A | 7/1996 | Johnson |
| 5,544,519 A | 8/1996 | Hammarberg et al. |
| 5,545,152 A | 8/1996 | Funderburk et al. |
| 5,564,915 A | 10/1996 | Johnson |
| 5,567,119 A | 10/1996 | Johnson |
| 5,567,136 A | 10/1996 | Johnson |
| 5,569,186 A | 10/1996 | Lord et al. |
| 5,570,716 A | 11/1996 | Kamen et al. |
| 5,574,008 A | 11/1996 | Johnson et al. |
| 5,575,310 A | 11/1996 | Kamen et al. |
| 5,575,770 A | 11/1996 | Melsky et al. |
| 5,578,002 A | 11/1996 | Slettenmark et al. |
| 5,578,005 A | 11/1996 | Sancoff et al. |
| 5,578,012 A | 11/1996 | Kamen et al. |
| 5,582,591 A | 12/1996 | Cheikh et al. |
| 5,584,813 A | 12/1996 | Livingston et al. |
| 5,602,171 A | 2/1997 | Tang et al. |
| 5,607,418 A | 3/1997 | Arzbaecher |
| 5,614,642 A | 3/1997 | Tang et al. |
| 5,616,123 A | 4/1997 | Cheikh et al. |
| 5,628,908 A | 5/1997 | Kamen et al. |
| 5,634,896 A | 6/1997 | Bryant et al. |
| 5,635,387 A | 6/1997 | Fei et al. |
| 5,637,095 A | 6/1997 | Nason et al. |
| 5,637,099 A | 6/1997 | Durdin et al. |
| 5,641,892 A | 6/1997 | Larkins et al. |
| 5,647,853 A | 7/1997 | Feldmann et al. |
| 5,647,854 A | 7/1997 | Olsen et al. |
| 5,655,897 A | 8/1997 | Neftel et al. |
| 5,656,032 A | 8/1997 | Kriesel et al. |
| 5,658,250 A | 8/1997 | Blomquist et al. |
| 5,658,252 A | 8/1997 | Johnson |
| 5,660,846 A | 8/1997 | Cheikh et al. |
| 5,665,065 A | 9/1997 | Colman et al. |
| 5,665,070 A | 9/1997 | McPhee |
| 5,669,877 A | 9/1997 | Blomquist |
| 5,672,167 A | 9/1997 | Athayde et al. |
| 5,694,919 A | 12/1997 | Rubsamen et al. |
| 5,695,473 A | 12/1997 | Olsen |
| 5,700,244 A | 12/1997 | Kriesel |
| 5,700,904 A | 12/1997 | Baker et al. |
| 5,702,372 A | 12/1997 | Nelson |
| 5,707,361 A | 1/1998 | Slettenmark et al. |
| 5,713,865 A | 2/1998 | Manning et al. |
| 5,716,343 A | 2/1998 | Kriesel et al. |
| 5,718,568 A | 2/1998 | Neftel et al. |
| 5,722,397 A | 3/1998 | Eppstein |
| 5,722,956 A | 3/1998 | Sims et al. |
| 5,735,263 A | 4/1998 | Rubsamen et al. |
| 5,738,658 A | 4/1998 | Maus et al. |
| 5,741,125 A | 4/1998 | Neftel et al. |
| 5,749,835 A | 5/1998 | Glantz |
| 5,755,683 A | 5/1998 | Houle et al. |
| 5,764,159 A | 6/1998 | Neftel et al. |
| 5,772,409 A | 6/1998 | Johnson |
| 5,777,060 A | 7/1998 | Van Antwerp |
| 5,782,798 A | 7/1998 | Rise |
| 5,785,681 A | 7/1998 | Indravudh |
| 5,785,688 A | 7/1998 | Joshi et al. |
| 5,788,671 A | 8/1998 | Johnson |
| 5,788,673 A | 8/1998 | Young et al. |
| 5,788,678 A | 8/1998 | Van Antwerp |
| 5,792,123 A | 8/1998 | Ensminger |
| 5,800,420 A | 9/1998 | Gross et al. |
| 5,800,421 A | 9/1998 | Lemelson |
| 5,807,315 A | 9/1998 | Van Antwerp et al. |
| 5,807,375 A | 9/1998 | Gross et al. |
| 5,810,015 A | 9/1998 | Flaherty |
| 5,810,771 A | 9/1998 | Blomquist |
| 5,820,622 A | 10/1998 | Gross et al. |
| 5,823,746 A | 10/1998 | Johnson |
| 5,827,262 A | 10/1998 | Neftel et al. |
| 5,837,234 A | 11/1998 | Gentile et al. |
| 5,837,276 A | 11/1998 | Cheikh et al. |
| 5,837,680 A | 11/1998 | Moses et al. |
| 5,843,023 A | 12/1998 | Cecchi |
| 5,848,990 A | 12/1998 | Cirelli et al. |
| 5,851,197 A | 12/1998 | Marano et al. |
| 5,858,001 A | 1/1999 | Tsals et al. |
| 5,858,969 A | 1/1999 | Marsh, Jr. et al. |
| 5,868,711 A | 2/1999 | Kramer et al. |
| 5,873,857 A | 2/1999 | Kriesel |
| 5,876,370 A | 3/1999 | Blomquist |
| 5,879,143 A | 3/1999 | Cote et al. |
| 5,882,494 A | 3/1999 | Van Antwerp |
| 5,891,086 A | 4/1999 | Weston |
| 5,906,592 A | 5/1999 | Kriesel et al. |
| 5,921,962 A | 7/1999 | Kriesel et al. |
| 5,928,196 A | 7/1999 | Johnson et al. |
| 5,935,099 A | 8/1999 | Peterson et al. |
| 5,935,105 A | 8/1999 | Manning et al. |
| 5,935,106 A | 8/1999 | Olsen |
| 5,935,598 A | 8/1999 | Sage et al. |
| 5,944,695 A | 8/1999 | Johnson et al. |
| 5,951,521 A | 9/1999 | Mastrototaro et al. |
| 5,952,347 A | 9/1999 | Arison et al. |
| 5,954,485 A | 9/1999 | Johnson et al. |
| 5,954,695 A | 9/1999 | Sims et al. |
| 5,957,890 A | 9/1999 | Mann et al. |
| 5,957,895 A | 9/1999 | Sage et al. |
| 5,960,797 A | 10/1999 | Kramer et al. |
| 5,961,499 A | 10/1999 | Bonutti et al. |
| 5,968,014 A | 10/1999 | Neftel et al. |
| 5,976,109 A | 11/1999 | Heruth |
| 5,989,423 A | 11/1999 | Kamen et al. |
| 5,995,860 A | 11/1999 | Sun et al. |
| 6,002,954 A | 12/1999 | Van Antwerp et al. |
| 6,006,753 A | 12/1999 | Efendic |
| 6,007,555 A | 12/1999 | Devine |
| 6,011,984 A | 1/2000 | Van Antwerp et al. |
| 6,012,034 A | 1/2000 | Hamparian et al. |
| 6,013,057 A | 1/2000 | Danby et al. |
| 6,017,318 A | 1/2000 | Gauthier et al. |
| 6,022,316 A | 2/2000 | Eppstein et al. |
| 6,024,539 A | 2/2000 | Blomquist |
| 6,025,331 A | 2/2000 | Moses et al. |
| 6,030,399 A | 2/2000 | Ignotz et al. |
| 6,040,194 A | 3/2000 | Chick et al. |
| 6,041,801 A | 3/2000 | Gray et al. |
| 6,043,273 A | 3/2000 | Duhaylongsod |
| 6,045,734 A | 4/2000 | Luther et al. |
| 6,048,328 A | 4/2000 | Haller et al. |
| 6,049,727 A | 4/2000 | Crothall |
| 6,051,557 A | 4/2000 | Drucker |
| 6,053,893 A | 4/2000 | Bucher et al. |
| 6,056,718 A | 5/2000 | Funderburk et al. |
| 6,056,734 A | 5/2000 | Jacobsen et al. |

| | | | | | | |
|---|---|---|---|---|---|---|
| 6,057,131 | A | 5/2000 | Marsh, Jr. et al. | 6,315,769 | B1 | 11/2001 | Peer et al. |
| 6,059,753 | A | 5/2000 | Faust et al. | 6,316,038 | B1 | 11/2001 | Veech |
| 6,065,941 | A | 5/2000 | Gray et al. | 6,319,540 | B1 | 11/2001 | Van Antwerp et al. |
| 6,068,613 | A | 5/2000 | Kriesel et al. | 6,321,597 | B1 | 11/2001 | Demers et al. |
| 6,070,761 | A | 6/2000 | Bloom et al. | 6,323,237 | B1 | 11/2001 | Veech |
| 6,074,369 | A | 6/2000 | Sage et al. | 6,329,336 | B1 | 12/2001 | Bridon et al. |
| 6,077,055 | A | 6/2000 | Vilks | 6,334,856 | B1 | 1/2002 | Allen et al. |
| 6,077,246 | A | 6/2000 | Kullas et al. | 6,338,730 | B1 | 1/2002 | Bonutti et al. |
| 6,077,248 | A | 6/2000 | Zumschlinge et al. | D453,830 | S | 2/2002 | McDowell et al. |
| 6,077,259 | A | 6/2000 | Caizza et al. | 6,343,614 | B1 | 2/2002 | Gray et al. |
| 6,083,201 | A | 7/2000 | Skinkle | 6,346,095 | B1 | 2/2002 | Gross et al. |
| 6,085,574 | A | 7/2000 | Neftel et al. | 6,348,043 | B1 | 2/2002 | Hagen et al. |
| 6,087,394 | A | 7/2000 | Duhaylongsod | 6,355,019 | B1 | 3/2002 | Kriesel et al. |
| 6,092,249 | A | 7/2000 | Kamen et al. | 6,355,021 | B1 | 3/2002 | Nielsen et al. |
| 6,093,167 | A | 7/2000 | Houben et al. | 6,360,888 | B1 | 3/2002 | McIvor et al. |
| 6,093,172 | A | 7/2000 | Funderburk et al. | 6,362,591 | B1 | 3/2002 | Moberg |
| 6,110,152 | A | 8/2000 | Kovelman | 6,364,279 | B1 | 4/2002 | Neftel et al. |
| 6,110,427 | A | 8/2000 | Uffenheimer | 6,364,857 | B1 | 4/2002 | Gray et al. |
| 6,110,721 | A | 8/2000 | Gibbs et al. | 6,368,274 | B1 | 4/2002 | Van Antwerp et al. |
| 6,112,111 | A | 8/2000 | Glantz | 6,374,876 | B2 | 4/2002 | Bynum |
| RE36,871 | E | 9/2000 | Epstein et al. | 6,375,459 | B1 | 4/2002 | Kamen et al. |
| 6,120,460 | A | 9/2000 | Abreu | 6,375,638 | B2 | 4/2002 | Nason et al. |
| 6,122,536 | A | 9/2000 | Sun et al. | 6,379,345 | B1 | 4/2002 | Constantz |
| 6,123,668 | A | 9/2000 | Abreu | 6,382,923 | B1 | 5/2002 | Gray |
| 6,123,685 | A | 9/2000 | Reynolds | 6,394,981 | B2 | 5/2002 | Heruth |
| 6,123,686 | A | 9/2000 | Olsen et al. | 6,403,558 | B1 | 6/2002 | Moses et al. |
| 6,126,642 | A | 10/2000 | Kriesel et al. | 6,406,455 | B1 | 6/2002 | Willis et al. |
| 6,127,410 | A | 10/2000 | Duhaylongsod | 6,414,018 | B1 | 7/2002 | Duhaylongsod |
| 6,135,978 | A | 10/2000 | Houben et al. | 6,416,293 | B1 | 7/2002 | Bouchard et al. |
| D434,142 | S | 11/2000 | Cheney, II et al. | 6,416,495 | B1 | 7/2002 | Kriesel et al. |
| 6,142,939 | A | 11/2000 | Eppstein et al. | 6,416,496 | B1 | 7/2002 | Rogers et al. |
| 6,142,972 | A | 11/2000 | Cheikh et al. | 6,422,057 | B1 | 7/2002 | Anderson |
| 6,152,898 | A | 11/2000 | Olsen | 6,423,001 | B1 | 7/2002 | Abreu |
| 6,155,824 | A | 12/2000 | Kamen et al. | 6,423,035 | B1 | 7/2002 | Das et al. |
| 6,165,154 | A | 12/2000 | Gray et al. | 6,424,847 | B1 | 7/2002 | Mastrototaro et al. |
| 6,168,609 | B1 | 1/2001 | Kamen et al. | 6,427,088 | B1 | 7/2002 | Bowman, IV et al. |
| 6,175,752 | B1 | 1/2001 | Say et al. | D461,241 | S | 8/2002 | Moberg et al. |
| 6,183,434 | B1 | 2/2001 | Eppstein | D461,891 | S | 8/2002 | Moberg |
| 6,183,441 | B1 | 2/2001 | Kriesel et al. | 6,429,197 | B1 | 8/2002 | Coolidge et al. |
| 6,186,982 | B1 | 2/2001 | Gross et al. | 6,432,383 | B1 | 8/2002 | Modi |
| 6,190,359 | B1 | 2/2001 | Heruth | 6,436,072 | B1 | 8/2002 | Kullas et al. |
| 6,191,102 | B1 | 2/2001 | DiMarchi et al. | 6,440,933 | B1 | 8/2002 | Bodor et al. |
| 6,193,704 | B1 | 2/2001 | Winters | 6,443,942 | B2 | 9/2002 | Van Antwerp et al. |
| 6,202,708 | B1 | 3/2001 | Bynum | 6,453,956 | B2 | 9/2002 | Safabash |
| 6,203,528 | B1 | 3/2001 | Deckert et al. | 6,458,102 | B1 | 10/2002 | Mann et al. |
| 6,206,850 | B1 | 3/2001 | O'Neil et al. | 6,458,355 | B1 | 10/2002 | Hsei et al. |
| 6,207,856 | B1 | 3/2001 | Veech | 6,461,329 | B1 | 10/2002 | Van Antwerp et al. |
| 6,210,361 | B1 | 4/2001 | Kamen et al. | 6,461,331 | B1 | 10/2002 | Van Antwerp |
| 6,213,943 | B1 | 4/2001 | Abreu | 6,464,667 | B1 | 10/2002 | Kamen et al. |
| 6,214,617 | B1 | 4/2001 | Herman | 6,464,671 | B1 | 10/2002 | Elver et al. |
| 6,223,130 | B1 | 4/2001 | Gray et al. | 6,465,431 | B1 | 10/2002 | Thorn et al. |
| 6,228,060 | B1 | 5/2001 | Howell | 6,468,532 | B1 | 10/2002 | Hsei et al. |
| 6,231,320 | B1 | 5/2001 | Lawless et al. | 6,471,436 | B1 | 10/2002 | Gjata et al. |
| 6,231,545 | B1 | 5/2001 | Kriesel et al. | 6,471,674 | B1 | 10/2002 | Emig et al. |
| 6,234,997 | B1 | 5/2001 | Kamen et al. | 6,475,180 | B2 | 11/2002 | Peterson et al. |
| 6,241,704 | B1 | 6/2001 | Peterson et al. | 6,475,196 | B1 | 11/2002 | Vachon |
| 6,248,067 | B1 | 6/2001 | Causey, III et al. | 6,485,263 | B1 | 11/2002 | Bryant et al. |
| 6,248,093 | B1 | 6/2001 | Moberg | 6,485,461 | B1 | 11/2002 | Mason et al. |
| 6,251,098 | B1 | 6/2001 | Rake et al. | 6,485,465 | B2 | 11/2002 | Moberg et al. |
| 6,253,804 | B1 | 7/2001 | Safabash | 6,495,366 | B1 | 12/2002 | Briggs |
| 6,254,586 | B1 | 7/2001 | Mann et al. | 6,495,532 | B1 | 12/2002 | Bathurst et al. |
| 6,259,587 | B1 | 7/2001 | Sheldon et al. | 6,500,150 | B1 | 12/2002 | Gross et al. |
| 6,261,272 | B1 | 7/2001 | Gross et al. | 6,503,062 | B1 | 1/2003 | Gray et al. |
| 6,261,280 | B1 | 7/2001 | Houben et al. | 6,503,184 | B1 | 1/2003 | Ni et al. |
| 6,267,564 | B1 | 7/2001 | Rapheal | 6,503,231 | B1 | 1/2003 | Prausnitz et al. |
| D446,854 | S | 8/2001 | Cheney, II et al. | 6,505,059 | B1 | 1/2003 | Kollias et al. |
| 6,270,478 | B1 | 8/2001 | Mern.o slashed.e | 6,512,939 | B1 | 1/2003 | Colvin et al. |
| 6,280,416 | B1 | 8/2001 | Van Antwerp et al. | 6,514,500 | B1 | 2/2003 | Bridon et al. |
| 6,283,943 | B1 | 9/2001 | Dy et al. | 6,520,326 | B2 | 2/2003 | McIvor et al. |
| 6,283,944 | B1 | 9/2001 | McMullen et al. | 6,520,747 | B2 | 2/2003 | Gray et al. |
| 6,284,725 | B1 | 9/2001 | Coolidge et al. | 6,520,936 | B1 | 2/2003 | Mann |
| 6,284,727 | B1 | 9/2001 | Kim et al. | 6,520,938 | B1 | 2/2003 | Funderburk et al. |
| 6,287,294 | B1 | 9/2001 | Lemelson | D471,352 | S | 3/2003 | Shetler et al. |
| 6,287,521 | B1 | 9/2001 | Quay et al. | 6,527,716 | B1 | 3/2003 | Eppstein |
| 6,293,925 | B1 | 9/2001 | Safabash et al. | 6,530,900 | B1 | 3/2003 | Daily et al. |
| 6,302,653 | B1 | 10/2001 | Bryant et al. | 6,537,268 | B1 | 3/2003 | Gibson et al. |
| 6,302,990 | B1 | 10/2001 | Nelson | 6,544,193 | B2 | 4/2003 | Abreu |
| 6,306,420 | B1 | 10/2001 | Cheikh et al. | 6,544,229 | B1 | 4/2003 | Danby et al. |
| 6,312,393 | B1 | 11/2001 | Abreu | 6,551,276 | B1 | 4/2003 | Mann et al. |

| Patent No. | Date | Inventor |
|---|---|---|
| 6,554,798 B1 | 4/2003 | Mann et al. |
| 6,554,800 B1 | 4/2003 | Nezhadian et al. |
| 6,555,986 B2 | 4/2003 | Moberg |
| 6,558,320 B1 | 5/2003 | Causey, III et al. |
| 6,558,343 B1 | 5/2003 | Neftel et al. |
| 6,558,345 B1 | 5/2003 | Houben et al. |
| 6,558,351 B1 | 5/2003 | Steil et al. |
| 6,560,471 B1 | 5/2003 | Heller et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,565,531 B1 | 5/2003 | Mori et al. |
| 6,565,534 B1 | 5/2003 | Winters |
| 6,565,535 B2 | 5/2003 | Zaias et al. |
| 6,565,885 B1 | 5/2003 | Tarara et al. |
| 6,571,128 B2 | 5/2003 | Lebel et al. |
| 6,572,586 B1 | 6/2003 | Wojcik |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,585,695 B1 | 7/2003 | Adair et al. |
| 6,586,401 B1 | 7/2003 | Thorn et al. |
| 6,589,936 B1 | 7/2003 | Thorn et al. |
| 6,591,876 B2 | 7/2003 | Safabash |
| 6,593,295 B2 | 7/2003 | Bridon et al. |
| 6,595,202 B2 | 7/2003 | Ganan-Calvo et al. |
| 6,595,756 B2 | 7/2003 | Gray et al. |
| 6,595,956 B1 | 7/2003 | Gross et al. |
| 6,604,908 B1 | 8/2003 | Bryant et al. |
| 6,607,509 B2 | 8/2003 | Bobroff et al. |
| 6,608,101 B1 | 8/2003 | Ni et al. |
| 6,610,288 B1 | 8/2003 | Edge et al. |
| 6,611,707 B1 | 8/2003 | Prausnitz et al. |
| 6,613,026 B1 | 9/2003 | Palasis et al. |
| 6,613,038 B2 | 9/2003 | Bonutti et al. |
| 6,616,627 B2 | 9/2003 | Willis et al. |
| 6,617,450 B1 | 9/2003 | Stocker et al. |
| 6,622,732 B2 | 9/2003 | Constantz |
| 6,629,954 B1 | 10/2003 | Heruth |
| 6,632,215 B1 | 10/2003 | Lemelson |
| 6,635,049 B1 | 10/2003 | Robinson et al. |
| 6,635,743 B1 | 10/2003 | Ebner et al. |
| 6,641,533 B2 | 11/2003 | Causey, III et al. |
| 6,641,562 B1 | 11/2003 | Peterson |
| 6,642,015 B2 | 11/2003 | Vachon et al. |
| 6,645,175 B2 | 11/2003 | Kriesel et al. |
| 6,648,821 B2 | 11/2003 | Lebel et al. |
| 6,651,656 B2 | 11/2003 | Demers et al. |
| 6,652,493 B1 | 11/2003 | Das |
| 6,652,510 B2 | 11/2003 | Lord et al. |
| 6,653,283 B1 | 11/2003 | Moses et al. |
| 6,656,148 B2 | 12/2003 | Das et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,982 B2 | 12/2003 | Douglas et al. |
| 6,660,509 B1 | 12/2003 | Herman et al. |
| 6,663,359 B2 | 12/2003 | Gray |
| 6,665,909 B2 | 12/2003 | Collins et al. |
| 6,666,845 B2 | 12/2003 | Hooper et al. |
| 6,669,663 B1 | 12/2003 | Thompson |
| 6,669,668 B1 | 12/2003 | Kleeman et al. |
| 6,669,669 B2 | 12/2003 | Flaherty et al. |
| 6,671,554 B2 | 12/2003 | Gibson et al. |
| 6,685,664 B2 | 2/2004 | Levin et al. |
| 6,687,546 B2 | 2/2004 | Lebel et al. |
| 6,689,073 B2 | 2/2004 | Quay |
| 6,689,100 B2 | 2/2004 | Connelly et al. |
| 6,689,108 B2 | 2/2004 | Lavi et al. |
| 6,689,607 B2 | 2/2004 | Ni et al. |
| 6,689,747 B2 | 2/2004 | Filvaroff et al. |
| 6,692,456 B1 | 2/2004 | Eppstein et al. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,699,219 B2 | 3/2004 | Emig et al. |
| 6,702,779 B2 | 3/2004 | Connelly et al. |
| 6,703,217 B2 | 3/2004 | Herman et al. |
| 6,709,417 B1 | 3/2004 | Houle et al. |
| 6,711,436 B1 | 3/2004 | Duhaylongsod |
| 6,716,190 B1 | 4/2004 | Glines et al. |
| 6,716,193 B1 | 4/2004 | Neftel |
| 6,721,582 B2 | 4/2004 | Trepagnier et al. |
| 6,723,072 B2 | 4/2004 | Flaherty et al. |
| 6,726,656 B2 | 4/2004 | Kamen et al. |
| 6,728,560 B2 | 4/2004 | Kollias et al. |
| 6,733,446 B2 | 5/2004 | Lebel et al. |
| 6,734,162 B2 | 5/2004 | Van Antwerp et al. |
| 6,734,186 B1 | 5/2004 | Maw et al. |
| 6,736,795 B2 | 5/2004 | Michel |
| 6,737,401 B2 | 5/2004 | Kim et al. |
| 6,740,059 B2 | 5/2004 | Flaherty |
| 6,740,072 B2 | 5/2004 | Starkweather et al. |
| 6,740,075 B2 | 5/2004 | Lebel et al. |
| 6,740,655 B2 | 5/2004 | Magee et al. |
| 6,749,403 B2 | 6/2004 | Bryant et al. |
| 6,749,587 B2 | 6/2004 | Flaherty |
| 6,750,311 B1 | 6/2004 | Van Antwerp et al. |
| 6,752,299 B2 | 6/2004 | Shetler et al. |
| 6,752,785 B2 | 6/2004 | Van Antwerp et al. |
| 6,752,787 B1 | 6/2004 | Causey, III et al. |
| 6,753,177 B1 | 6/2004 | Stocker et al. |
| 6,753,328 B2 | 6/2004 | Wands et al. |
| 6,755,811 B1 | 6/2004 | Constantz |
| 6,758,810 B2 | 7/2004 | Lebel et al. |
| 6,766,183 B2 | 7/2004 | Walsh et al. |
| 6,768,425 B2 | 7/2004 | Flaherty et al. |
| 6,770,067 B2 | 8/2004 | Lorenzen et al. |
| 6,770,729 B2 | 8/2004 | Van Antwerp |
| 6,774,120 B1 | 8/2004 | Ferber et al. |
| 6,784,274 B2 | 8/2004 | Van Antwerp et al. |
| 6,792,982 B2 | 9/2004 | Lincoln et al. |
| 6,796,956 B2 | 9/2004 | Hartlaub et al. |
| 6,796,957 B2 | 9/2004 | Carpenter et al. |
| 6,800,071 B1 | 10/2004 | McConnell et al. |
| 6,800,663 B2 | 10/2004 | Asgarzadeh et al. |
| 6,801,420 B2 | 10/2004 | Talbot et al. |
| 6,804,544 B2 | 10/2004 | Van Antwerp et al. |
| 6,805,687 B2 | 10/2004 | Dextradeur et al. |
| 6,805,693 B2 | 10/2004 | Gray et al. |
| 6,808,369 B2 | 10/2004 | Gray et al. |
| 6,808,506 B2 | 10/2004 | Lastovich et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,715 B2 | 11/2004 | Bonutti et al. |
| 6,817,990 B2 | 11/2004 | Yap et al. |
| 6,821,949 B2 | 11/2004 | Bridon et al. |
| 6,824,529 B2 | 11/2004 | Gross et al. |
| 6,827,702 B2 | 12/2004 | Lebel et al. |
| 6,830,558 B2 | 12/2004 | Flaherty et al. |
| 6,830,564 B2 | 12/2004 | Gray |
| 6,840,922 B2 | 1/2005 | Nielsen et al. |
| 6,843,782 B2 | 1/2005 | Gross et al. |
| 6,849,718 B2 | 2/2005 | Kaelin, Jr. et al. |
| 6,849,719 B2 | 2/2005 | Shi et al. |
| 6,902,544 B2 | 6/2005 | Ludin et al. |
| 6,936,029 B2 | 8/2005 | Mann et al. |
| 6,939,324 B2 | 9/2005 | Gonnelli et al. |
| 6,960,184 B2 | 11/2005 | Willis et al. |
| 6,979,316 B1 | 12/2005 | Rubin et al. |
| 7,011,234 B2 | 3/2006 | Stradella |
| 7,014,625 B2 | 3/2006 | Bengtsson |
| 7,022,107 B1 | 4/2006 | Christensen et al. |
| 7,108,686 B2 | 9/2006 | Burke et al. |
| 7,150,409 B2 | 12/2006 | Gonnelli et al. |
| 7,204,823 B2 | 4/2007 | Estes et al. |
| 7,250,037 B2 | 7/2007 | Shermer et al. |
| 7,337,922 B2 | 3/2008 | Rake et al. |
| 7,367,968 B2 | 5/2008 | Rosenberg et al. |
| 7,481,792 B2 | 1/2009 | Gonnelli et al. |
| 7,530,968 B2 | 5/2009 | Gonnelli |
| 7,534,226 B2 | 5/2009 | Mernoe et al. |
| 7,678,079 B2 | 3/2010 | Shermer et al. |
| 2001/0005781 A1 | 6/2001 | Bergens et al. |

| | | | | | | |
|---|---|---|---|---|---|---|
| 2001/0010238 A1 | 8/2001 | Bynum | | 2004/0209801 A1 | 10/2004 | Brand et al. |
| 2001/0016710 A1 | 8/2001 | Nason et al. | | 2004/0220456 A1 | 11/2004 | Eppstein |
| 2001/0027287 A1 | 10/2001 | Shmulewitz et al. | | 2004/0220525 A1 | 11/2004 | Willis et al. |
| 2001/0031944 A1 | 10/2001 | Peterson et al. | | 2004/0225281 A1 | 11/2004 | Lorenzen et al. |
| 2001/0037083 A1 | 11/2001 | Hartlaub et al. | | 2004/0247445 A1 | 12/2004 | Nelson et al. |
| 2001/0053891 A1 | 12/2001 | Ackley | | 2004/0249363 A1 | 12/2004 | Burke et al. |
| 2001/0056259 A1 | 12/2001 | Skinkle et al. | | 2004/0250382 A1 | 12/2004 | Collins et al. |
| 2002/0004015 A1 | 1/2002 | Carlisle et al. | | 2004/0254525 A1 | 12/2004 | Uber et al. |
| 2002/0019612 A1 | 2/2002 | Watanabe et al. | | 2004/0260234 A1 | 12/2004 | Srinivasan et al. |
| 2002/0040208 A1 | 4/2002 | Flaherty et al. | | 2004/0266678 A1 | 12/2004 | Beeley et al. |
| 2002/0045867 A1 | 4/2002 | Nielsen et al. | | 2004/0267201 A1 | 12/2004 | Agerup |
| 2002/0055460 A1 | 5/2002 | Coolidge et al. | | 2005/0008661 A1 | 1/2005 | Fereira et al. |
| 2002/0061838 A1 | 5/2002 | Holmquist et al. | | 2005/0024175 A1 | 2/2005 | Gray et al. |
| 2002/0072733 A1 | 6/2002 | Flaherty | | 2005/0033232 A1 | 2/2005 | Kriesel |
| 2002/0077599 A1 | 6/2002 | Wojcik | | 2005/0038387 A1 | 2/2005 | Kriesel et al. |
| 2002/0091358 A1 | 7/2002 | Klitmose | | 2005/0054988 A1 | 3/2005 | Rosenberg et al. |
| 2002/0095124 A1 | 7/2002 | Palasis et al. | | 2005/0065472 A1 | 3/2005 | Cindrich et al. |
| 2002/0123716 A1 | 9/2002 | VanDiver et al. | | 2005/0070875 A1 | 3/2005 | Kulessa |
| 2002/0123740 A1 | 9/2002 | Flaherty et al. | | 2005/0112188 A1 | 5/2005 | Eliaz et al. |
| 2002/0128594 A1 | 9/2002 | Das et al. | | 2005/0119618 A1 | 6/2005 | Gonnelli |
| 2002/0138049 A1 | 9/2002 | Allen et al. | | 2005/0137530 A1 | 6/2005 | Campbell et al. |
| 2002/0147131 A1 | 10/2002 | Coolidge et al. | | 2005/0137578 A1 | 6/2005 | Heruth et al. |
| 2002/0151842 A1 | 10/2002 | Gonnelli et al. | | 2005/0171477 A1 | 8/2005 | Rubin et al. |
| 2002/0151846 A1 | 10/2002 | Christenson et al. | | 2005/0171512 A1 | 8/2005 | Flaherty |
| 2002/0156418 A1 | 10/2002 | Gonnelli et al. | | 2005/0177109 A1 | 8/2005 | Azzolini |
| 2002/0156464 A1 | 10/2002 | Blischak et al. | | 2005/0215850 A1 | 9/2005 | Klein et al. |
| 2002/0177809 A1 | 11/2002 | Kriesel et al. | | 2005/0245904 A1 | 11/2005 | Estes et al. |
| 2002/0183693 A1 | 12/2002 | Peterson et al. | | 2005/0273083 A1 | 12/2005 | Lebel et al. |
| 2002/0188259 A1 | 12/2002 | Hickle et al. | | 2005/0277912 A1* | 12/2005 | John .................... 604/890.1 |
| 2002/0198493 A1 | 12/2002 | Diaz et al. | | 2005/0278073 A1 | 12/2005 | Roth |
| 2002/0198494 A1 | 12/2002 | Diaz et al. | | 2006/0030838 A1 | 2/2006 | Gonnelli |
| 2003/0009133 A1 | 1/2003 | Ramey | | 2006/0069382 A1 | 3/2006 | Pedersen |
| 2003/0022823 A1 | 1/2003 | Efendic | | 2006/0079862 A1 | 4/2006 | Genosar |
| 2003/0024508 A1 | 2/2003 | Hellar et al. | | 2006/0100578 A1 | 5/2006 | Lieberman |
| 2003/0050237 A1 | 3/2003 | Kim et al. | | 2006/0122628 A1 | 6/2006 | Solar et al. |
| 2003/0050623 A1 | 3/2003 | Lord et al. | | 2006/0150747 A1 | 7/2006 | Malle |
| 2003/0073626 A1 | 4/2003 | Hathaway et al. | | 2006/0184119 A1 | 8/2006 | Remde et al. |
| 2003/0100888 A1 | 5/2003 | Spinello | | 2006/0184154 A1 | 8/2006 | Moberg et al. |
| 2003/0125669 A1 | 7/2003 | Safabash et al. | | 2006/0189939 A1 | 8/2006 | Gonnelli et al. |
| 2003/0130619 A1 | 7/2003 | Safabash et al. | | 2006/0200112 A1 | 9/2006 | Paul |
| 2003/0130647 A1 | 7/2003 | Gray et al. | | 2006/0264831 A1 | 11/2006 | Skwarek et al. |
| 2003/0135158 A1 | 7/2003 | Gonnelli | | 2006/0264835 A1 | 11/2006 | Nielsen et al. |
| 2003/0135160 A1 | 7/2003 | Gray et al. | | 2007/0016170 A1 | 1/2007 | Kovelman |
| 2003/0158520 A1 | 8/2003 | Safabash et al. | | 2007/0060894 A1 | 3/2007 | Dai et al. |
| 2003/0167039 A1 | 9/2003 | Moberg | | 2007/0073236 A1 | 3/2007 | Mernoe et al. |
| 2003/0195157 A1 | 10/2003 | Natarajan et al. | | 2007/0100283 A1 | 5/2007 | Causey, III et al. |
| 2003/0199445 A1 | 10/2003 | Knudsen et al. | | 2007/0149925 A1 | 6/2007 | Edwards et al. |
| 2003/0199823 A1 | 10/2003 | Bobroff et al. | | 2007/0167912 A1 | 7/2007 | Causey et al. |
| 2003/0212000 A1 | 11/2003 | Van Antwerp | | 2007/0173761 A1 | 7/2007 | Kanderian, Jr. et al. |
| 2003/0216714 A1 | 11/2003 | Gill | | 2007/0179444 A1 | 8/2007 | Causey et al. |
| 2003/0220610 A1 | 11/2003 | Lastovich et al. | | 2007/0239114 A1 | 10/2007 | Edwards et al. |
| 2003/0225373 A1 | 12/2003 | Bobroff et al. | | 2007/0287958 A1 | 12/2007 | McKenzie et al. |
| 2003/0229309 A1 | 12/2003 | Babkes et al. | | 2007/0287985 A1 | 12/2007 | Estes et al. |
| 2003/0233069 A1 | 12/2003 | Gillespie et al. | | 2008/0058719 A1 | 3/2008 | Edwards et al. |
| 2004/0002682 A1 | 1/2004 | Kovelman et al. | | 2008/0091176 A1 | 4/2008 | Alessi et al. |
| 2004/0029784 A1 | 2/2004 | Hathaway | | 2008/0106431 A1 | 5/2008 | Blomquist |
| 2004/0064086 A1 | 4/2004 | Gottlieb et al. | | 2008/0125701 A1 | 5/2008 | Moberg et al. |
| 2004/0064096 A1 | 4/2004 | Flaherty et al. | | 2008/0139910 A1 | 6/2008 | Mastrototaro et al. |
| 2004/0064097 A1 | 4/2004 | Peterson | | 2008/0183060 A1 | 7/2008 | Steil et al. |
| 2004/0073161 A1 | 4/2004 | Tachibana | | 2008/0215006 A1 | 9/2008 | Thorkild |
| 2004/0077000 A1 | 4/2004 | Stocker et al. | | 2008/0249468 A1 | 10/2008 | Edwards et al. |
| 2004/0085215 A1 | 5/2004 | Moberg et al. | | 2008/0306436 A1 | 12/2008 | Edwards et al. |
| 2004/0091374 A1 | 5/2004 | Gray | | 2008/0312512 A1 | 12/2008 | Brukalo et al. |
| 2004/0092873 A1 | 5/2004 | Moberg | | 2008/0319383 A1 | 12/2008 | Byland et al. |
| 2004/0092893 A1 | 5/2004 | Haider et al. | | 2009/0054867 A1 | 2/2009 | Gravesen et al. |
| 2004/0094823 A1 | 5/2004 | Matsuno | | 2009/0062747 A1 | 3/2009 | Saul |
| 2004/0115067 A1 | 6/2004 | Rush et al. | | 2009/0088689 A1 | 4/2009 | Carter |
| 2004/0116905 A1 | 6/2004 | Pedersen et al. | | 2009/0088692 A1 | 4/2009 | Adams et al. |
| 2004/0126372 A1 | 7/2004 | Banerjee et al. | | 2009/0093772 A1 | 4/2009 | Genosar et al. |
| 2004/0126373 A1 | 7/2004 | Banerjee et al. | | 2009/0182277 A1 | 7/2009 | Carter |
| 2004/0133163 A1 | 7/2004 | Schiffmann | | 2009/0202608 A1 | 8/2009 | Allessi et al. |
| 2004/0143216 A1 | 7/2004 | Douglass et al. | | 2009/0220358 A1 | 9/2009 | Krivsky et al. |
| 2004/0143217 A1 | 7/2004 | Michel | | 2009/0240232 A1 | 9/2009 | Gonnelli et al. |
| 2004/0143218 A1 | 7/2004 | Das | | 2009/0247982 A1 | 10/2009 | Krulevitch et al. |
| 2004/0153032 A1 | 8/2004 | Garribotto et al. | | 2009/0281528 A1 | 11/2009 | Grovender et al. |
| 2004/0155079 A1 | 8/2004 | Shetler et al. | | | | |
| 2004/0167464 A1 | 8/2004 | Ireland et al. | | | FOREIGN PATENT DOCUMENTS | |
| 2004/0167470 A1 | 8/2004 | Emig et al. | | EP | 0209677 A1 | 1/1987 |
| 2004/0176725 A1 | 9/2004 | Stutz et al. | | EP | 0401179 A1 | 12/1990 |

| | | | |
|---|---|---|---|
| EP | 0513879 | A2 | 11/1992 |
| EP | 0098592 | A2 | 1/1994 |
| EP | 0638324 | A1 | 2/1995 |
| EP | 0937475 | A2 | 8/1999 |
| EP | 0902696 | B1 | 3/2002 |
| EP | 1173197 | B1 | 12/2004 |
| EP | 1512410 | | 3/2005 |
| EP | 1210136 | B1 | 1/2006 |
| GB | 2054381 | | 2/1981 |
| JP | 62-079067 | | 4/1987 |
| JP | 62270167 | | 11/1987 |
| JP | 10-506827 | | 7/1998 |
| JP | 2002-355317 | | 12/2002 |
| JP | 06-507828 | | 3/2006 |
| JP | 2006-524555 | | 11/2006 |
| NL | 7310455 | A | 2/1974 |
| RU | 2248223 | C2 | 3/2005 |
| SU | 1055518 | | 11/1983 |
| WO | 8503232 | A1 | 1/1985 |
| WO | 9728835 | | 8/1997 |
| WO | 9808871 | A1 | 3/1998 |
| WO | 9810129 | A1 | 12/1998 |
| WO | 9947161 | A1 | 9/1999 |
| WO | 9948546 | A | 9/1999 |
| WO | 0066138 | A2 | 11/2000 |
| WO | 0066142 | A2 | 11/2000 |
| WO | 0100223 | A2 | 1/2001 |
| WO | 0187322 | A2 | 11/2001 |
| WO | 0285406 | A1 | 10/2002 |
| WO | 03008023 | A1 | 1/2003 |
| WO | 03050846 | A3 | 6/2003 |
| WO | 03061362 | A2 | 7/2003 |
| WO | 03080160 | A1 | 10/2003 |
| WO | 2004037195 | A2 | 5/2004 |
| WO | 2004089335 | A2 | 10/2004 |
| WO | 2004/094823 | A2 | 11/2004 |
| WO | 2004094823 | A2 | 11/2004 |
| WO | 2005046716 | A1 | 5/2005 |
| WO | 2005048952 | A2 | 6/2005 |
| WO | 2005060986 | A1 | 7/2005 |
| WO | 2007051139 | A2 | 5/2007 |
| WO | 2007129317 | A1 | 11/2007 |
| WO | 2008036509 | A3 | 3/2008 |
| WO | 2008139458 | A3 | 11/2008 |
| WO | 2009013735 | A1 | 1/2009 |
| WO | 2009016637 | A1 | 2/2009 |
| WO | 2009081403 | A2 | 7/2009 |
| WO | 2009125398 | A2 | 10/2009 |

OTHER PUBLICATIONS

Supplementary European Search Report for European Patent Application No. EP 07 75 9578 dated Dec. 7, 2011.

Banks et al., Brain uptake of the glucagon-like peptide-1 antagonist exendin(9-39) after intranasal administration. J Pharmacol Exp Ther. 309(2): 469-75, 2004.

Capaldi, Treatments and devices for future diabetes management. Nurs Times. 101(18): 30-2, 2005.

Choi et al., Control of blood glucose by novel GLP-1 delivery using biodegradable triblock copolymer of PLGA-PEG-PLGA in types 2 diabetic rats. Pharm Res. 21(5); 827-31, 2004.

Donahey et al., Intraventricular GLP-1 reduces short-but not long-term food intake or body weight in lean and obese rats. Brain Res. 779(1-2): 75-83, 1998.

Drucker, Development of glucagon-like peptide-1 based pharmaceuticals as therapeutic agents for the treatment of diabetes. Curr Pharm Des. 7(14): 1399-412, 2001.

Gappa et al., The effect of zinc-crystallized glucagon-like peptide-1 on insulin secretion of macroencapsulated pancreatic islets. Tissue Eng. 7(1): 35-44, 2001.

Haak, New developments in the treatment of type 1 diabetes mellitus. Exp Clin Endocrinol Diabetes. 107 Suppl 3: S108-13, 1999.

Holst et al., On the treatment of diabetes mellitus with glucagon-like peptide-1. Ann N Y Acad Sci. 865: 336-43, 1998.

Hui et al., The short half-life of glucagon-like peptide-1 in plasma does not reflect its long-lasting beneficial effects. Eur J Endocrinol. 146(6): 863-9, 2002.

Joseph et al. Oral delivery of glucagon-like peptide-1 in a modified polymer preparation normalizes basal glycaemia in diabeetic db/db mice. Diabetologia. 43(10): 1319-28, 2000.

Toft-Nielson et al., Continuous subcutaneous infusion of glucagon-like peptide 1 lowers plasma glucose and reduces appetite in type 2 diabetic patients. Diabetes Care. 22(7): 1137-43, 1999.

Wang et al., Glucagon-like peptide-1 can reverse the age-related decline in glucose tolerance in rats. J Clin Invest. 99 (12): 2883-9, 1997.

Office action from U.S. Appl. No. 11/175,990 dated Nov. 10, 2009.
Office action from U.S. Appl. No. 11/175,990 dated Jan. 19, 2007.
Office action from U.S. Appl. No. 11/175,990 dated Oct. 2, 2007.
Office action from U.S. Appl. No. 11/175,990 dated Jan. 29, 2009.
Office action from U.S. Appl. No. 10/831,354 dated Sep. 18, 2006.
Office action from U.S. Appl. No. 10/831,354 dated May 4, 2007.
Office action from U.S. Appl. No. 10/831,354 dated Jul. 31, 2008.
Notice of Allowance from U.S. Appl. No. 10/831,354 dated Mar. 23, 2009.

Singapore Written Opinion from Singapore Pat. App. No. 2008070302-5 dated Jan. 6, 2010.

Gonnelli, Robert R. Barnell International Needle-Free Injection Systems presentation materials, Mar. 25, 2004, BioValve Technologies, Inc.(10 pages).

International Search Report and Written Opinion mailed Dec. 10, 2010 in connection with International Application No. PCT/US10/52352.

English Translation of First Office Action issued in connection with Chinese Application No. 200780020245.9.

First EPO Examination Report issued in connection with European Application No. 01988242.2.

Examiner's First Report on Australian Patent Application No. 2011201473 dated Feb. 14, 2012.

Office Action for U.S. Appl. No. 12/336,395 dated Sep. 21, 2011.

Decision of Grant for Russian Patent Application No. 2008143015 dated Jul. 6, 2011.

\* cited by examiner

MULTI-CARTRIDGE FLUID DELIVERY DEVICE

CROSS-REFERENCE TO RELATED APPLICATIONS

This application is a continuation of U.S. application Ser. No. 12/295,173, filed Mar. 28, 2007, which is a U.S. National Stage Entry of International Application No. PCT/US2007/065363, filed Mar. 28, 2007, which claim the benefit under 35 U.S.C. §119(e) of U.S. Provisional Application Ser. No. 60/787,616, filed Mar. 30, 2006, the disclosures of which are hereby incorporated by reference herein in their entirety.

In addition, cross-reference is made to U.S. Pat. No. 6,939,324 titled FLUID DELIVERY AND MEASUREMENT SYSTEMS AND METHODS; U.S. Patent Application Publication No. US 2005/0119618 titled HYDRAULICALLY ACTUATED PUMP FOR LONG DURATION MEDICAMENT ADMINISTRATION; and U.S. application Ser. No. 11/219,944 titled FLUID DELIVERY AND MEASUREMENT SYSTEMS AND METHODS, the disclosure of each of which is hereby incorporated by reference herein.

FIELD OF THE DISCLOSURE

The present disclosure relates generally to fluid delivery devices and particularly to fluid delivery devices capable of delivering one or more medicaments to a patient to provide a sustained, basal delivery and/or a bolus delivery of each medicament.

BACKGROUND

Fluid delivery devices, such as ambulatory infusion pumps, for example, have been developed for delivering liquid medicaments to a patient. Many such pumps or drug delivery devices are able to provide both steady state delivery ("basal delivery") and instantaneous bursts of a predetermined amount of drug ("bolus delivery") as required. In many instances, it is beneficial to provide a basal delivery of a drug which may be supplemented by a bolus delivery as well. For example, insulin for diabetes treatment as well as patient controlled analgesia for chronic pain treatment may be administered both at a continuous basal rate of delivery as well as via bolus amounts of delivery. Many such drug delivery devices are compact and able to be fixed to the user or patient during use and subsequently disposed of when the treatment is finished.

Many attempts have been made to provide continuous or near continuous basal delivery of such medicaments using various pump systems. The accuracy of the basal delivery rate often varies when the volume of the drug being delivered is small. Many fluid delivery devices include a reservoir to contain the liquid medicament and use various mechanical, gas, or electromechanical pumping or metering technologies to deliver the medicament to the patient via a needle or other catheter inserted transcutaneously, or through the skin of the patient.

SUMMARY

The present invention comprises one or more of the features recited in the appended claims or the following features or combinations thereof:

According to one aspect of the disclosure, a fluid delivery device for administering a first medicament and a second medicament is provided. The fluid delivery device may function to administer a basal delivery of the first medicament and/or a basal delivery of the second medicament. Further, the fluid delivery device may function to administer a bolus delivery of the first medicament and/or a bolus delivery of the second medicament. In other words, any combination of basal and/or bolus deliveries of each of the first and second medicaments is contemplated.

Various configurations of basal drive mechanisms of the fluid delivery device may provide the basal delivery of the first and/or second medicament. For example, one basal drive mechanism may provide the basal delivery of only the first medicament, only the second medicament, or both the first and second medicaments. In instances where the basal drive mechanism provides the basal delivery of only one of the first and second medicaments, a second basal drive mechanism of the fluid delivery device may provide the basal delivery of the other medicament.

Similarly, various configurations of bolus drive mechanisms of the fluid delivery device may provide the bolus delivery of the first and/or second medicament. For example, one bolus drive mechanism may provide the bolus delivery of only the first medicament, only the second medicament, or both the first and second medicaments. In instances where the bolus drive mechanism provides the bolus delivery of only one of the first and second medicaments, a second bolus drive mechanism of the fluid delivery device may provide the bolus delivery of the other medicament.

According to another aspect of the present disclosure, the fluid delivery device may include one or more needles in fluid communication with the first and second reservoirs containing the first and second medicaments. For example, a first needle may be in fluid communication with the reservoir containing the first medicament while a second needle may be in fluid communication with reservoir containing the second medicament. Such needles may be spaced-apart from each other or positioned on opposite ends of the fluid delivery device to substantially prevent any mixing of the first and second medicaments during delivery. Further, one needle may include a delivery arm (for subcutaneous insertion into the patient's skin) which is longer than a delivery arm of the other needle. In such a case, one of the first and second medicaments will be delivered to a subcutaneous depth greater than the other one of the first and second medicaments. Delivering the medicaments to a different depth may also substantially prevent any mixing of the first and second medicaments.

According to still another aspect of the present disclosure, a single needle may be provided which is in fluid communication with each reservoir of the first and second medicaments. Such a needle may be "Y-shaped" and include a first uptake arm for fluid communication with the reservoir containing first medicament and a second uptake arm for fluid communication with the reservoir containing the second medicament. Each of the first and second uptake arms of the needle may be in fluid communication with a delivery arm of the needle such that the first and second medicaments may mix with each other within the delivery arm of the needle prior to being delivered into the patient.

Illustratively, a fluid delivery device of the present disclosure may include an exterior housing, a first reservoir within the housing configured to contain the first medicament, and a second reservoir within the housing configured to contain the second medicament. The fluid delivery device may further include a needle having a first end configured for fluid communication with the first reservoir and a second end configured to extend exteriorly from the housing. Alternatively, the needle may include a third end configured for fluid communication with the second reservoir containing the second medicament. The fluid delivery device may further include a second needle having a first end configured for fluid communication with the second reservoir and a second end configured to extend exteriorly from the housing. The first needle may be positioned at a first end of the housing while the second needle may be positioned at a second end of the housing. Further, a delivery arm of the first needle may be longer than a delivery arm of the second needle.

Further illustratively, the fluid delivery device may include a basal drive mechanism for providing a basal delivery of the first medicament. The same basal drive mechanism may also provide a basal delivery of the second medicament. Alternatively, a second basal drive mechanism may provide the basal delivery of the second medicament. In either case, the basal drive mechanism may include a coil spring, a basal drive piston, and a hydraulic fluid reservoir. Further, the fluid delivery device may include a first pump chamber associated with the first medicament in fluid communication with the hydraulic fluid reservoir of the first basal drive mechanism via a first flow restrictor. Similarly, a second pump chamber associated with the second medicament may be in fluid communication with the hydraulic fluid reservoir of the second basal drive mechanism via a second flow restrictor.

Further illustratively, a first delivery piston of the fluid delivery device may be positioned within the first fluid reservoir to exert a force on the first medicament within the first fluid reservoir. Similarly, a second delivery piston may be positioned within the second fluid reservoir to exert a force on the second medicament within the second fluid reservoir.

The fluid delivery device may further include a bolus drive mechanism for providing a bolus delivery of the first medicament. The same bolus drive mechanism may also provide a bolus delivery of the second medicament. Alternatively, a second bolus drive mechanism may provide the bolus delivery of the second medicament. In either case, the bolus drive mechanism may include a ratchet and a bolus piston coupled to the ratchet. A pump chamber of the fluid delivery device is associated with the first fluid reservoir and the bolus piston is positioned within a bolus fluid reservoir in fluid communication with the pump chamber.

According to another aspect of the present disclosure, a method of administering first and second medicaments from an fluid delivery device includes delivering a first basal delivery of the first medicament, and delivering a second basal delivery of the second medicament. The first basal delivery may be approximately equal to the second basal delivery. Alternatively, the first basal delivery may be greater than the second basal delivery.

Illustratively, delivering the first medicament may include actuating a first basal drive mechanism and delivering the second medicament may similarly include actuating the first basal drive mechanism. Alternatively, delivering the second medicament may include actuating a second basal drive mechanism different from the first basal drive mechanism.

The method may further include delivering a first bolus delivery of the first medicament and delivering a second bolus delivery of the second medicament. The first bolus delivery may be the same as the second bolus delivery. Alternatively, the first bolus delivery may be greater than the second bolus delivery.

Illustratively, delivering the first bolus delivery may include actuating a first bolus drive mechanism and delivering the second bolus delivery may include actuating the first bolus drive mechanism. Alternatively, delivering the second bolus delivery may include actuating a second bolus drive mechanism different from the first bolus drive mechanism.

According to still another aspect of the present disclosure, another method of administering first and second medicaments from a fluid delivery device includes (i) forcing hydraulic fluid from a hydraulic fluid reservoir into a first pump chamber to exert a force on a first movable barrier, (ii) forcing hydraulic fluid from the hydraulic fluid reservoir into a second pump chamber to exert a force on a second movable barrier, (iii) exerting a force on a first piston to expel at least a portion of the first medicament through an aperture of the first fluid reservoir, and (iv) exerting a force on a second piston to expel at least a portion of the second medicament through an aperture of the second fluid reservoir.

Illustratively, forcing the hydraulic fluid from the hydraulic fluid reservoir may include applying a spring force to a piston within the hydraulic fluid reservoir. Forcing the hydraulic fluid from the hydraulic fluid reservoir may further include forcing hydraulic fluid from the hydraulic fluid reservoir through a flow restrictor and into the first and second pump chambers.

The fluid delivery devices described herein may be used to delivery a wide variety of drugs, pharmaceutical agents, and medicaments, and other components useful for treating diseases and disease states. In one embodiment, the delivery devices described herein include or are configured or adapted to include pre-selected medicaments in the corresponding reservoirs. In one aspect, the pre-selected medicaments are used to treat diabetes and/or diabetic conditions. In another aspect, the pre-selected medicaments are used to treat bacterial infections and/or other diseases associated with pathogenic cell populations. In another aspect, the pre-selected medicaments are used to treat diseases associated with neurotransmitter dysfunction, including but not limited to diseases that are treatable with dopamine and/or compounds that function as dopamine agonists and/or dopamine antagonists.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

Figure 1:
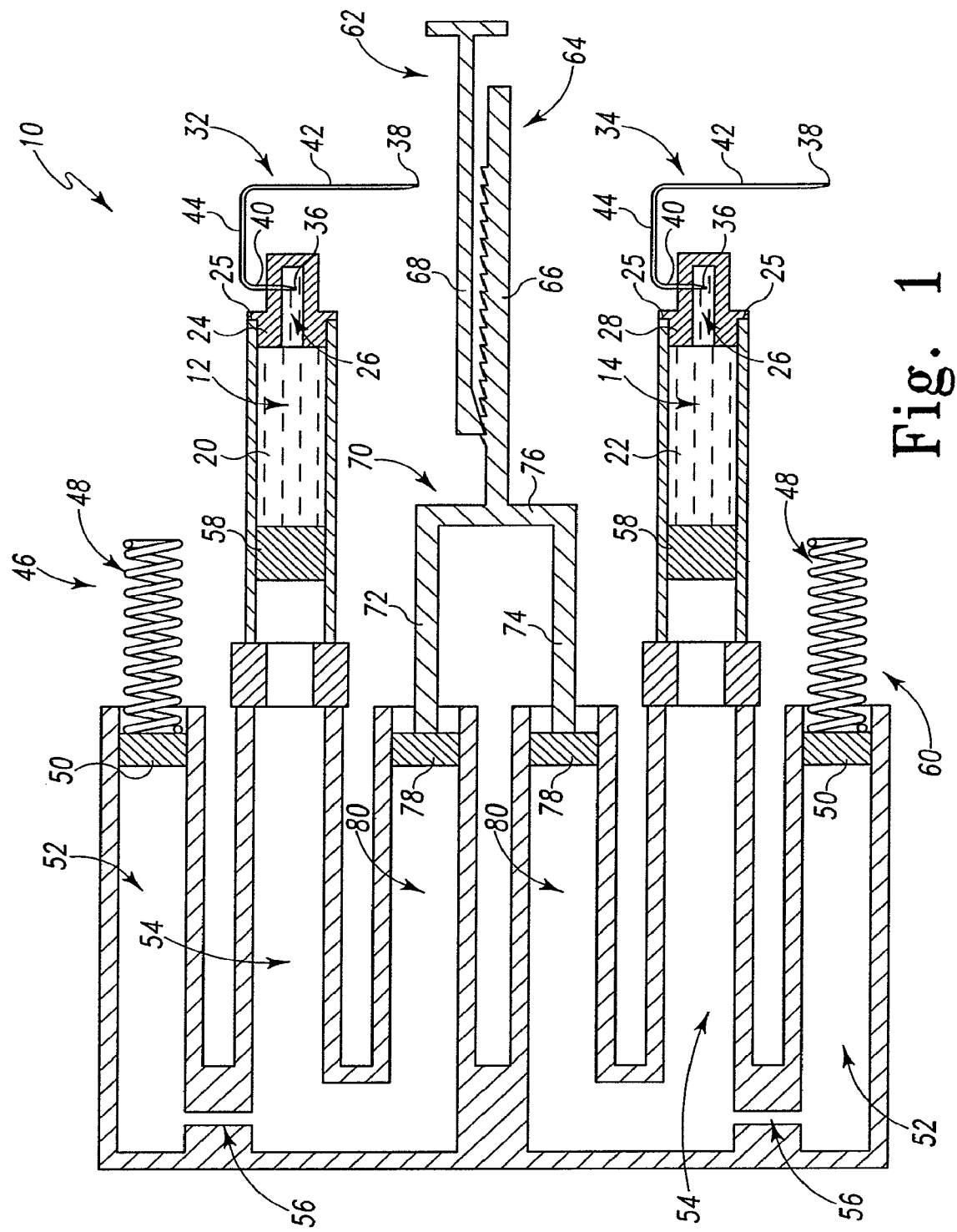
FIGS. 1-5b are schematics showing dual-cartridge drug delivery devices of the present disclosure which provide a basal delivery of both first and second medicaments and which provide a bolus delivery of both first and second medicaments.

Looking first to FIGS. 1-5b, various fluid or drug delivery devices 10, 110, 210, 310, 410, and 450 are provided. Each of these drug delivery devices 10, 110, 210, 310, 410, and 450 is capable of delivering a first medicament 20 at both a sustained steady state or basal delivery or infusion as well as an instantaneous amount of the first medicament 20 to provide a short term pulsatile or bolus delivery or infusion. Further, each of the drug delivery devices 10, 110, 210, 310, 410, and 450 is able to provide both a basal delivery of a second medicament 22 and a bolus delivery of the second medicament 22. The means by which each device delivers the first and second medicaments is discussed below.

It should be appreciated that the fluid delivery devices described herein each include an outer or exterior housing (not shown). The structures shown in FIGS. 1-17, therefore, are generally contained within such a housing. Illustratively, the housing may include various buttons or actuators engagable by a user or patient which activate the basal and bolus drive mechanisms described herein. Further, as is discussed in greater detail below, the needles 32, 34 of each fluid delivery device shown in FIGS. 1-17 are movable between a first, un-activated configuration (not shown) whereby the entirety of the needle is either contained within the outer housing and/or within an external button of the outer housing, and a second activated configuration. In the second activated configuration (shown in FIGS. 1-17), the needle is lowered such that one portion of the needle is in fluid communication with a reservoir containing one of the first and second medicaments 20, 22 and a second portion of the needle is positioned outside of the outer housing of the device for subcutaneous insertion into a patient, for example. Illustratively, the needle is configured for generally simultaneous insertion into one of the fluid reservoirs (or the stopper associated with each reservoir) and the patient. In other words, movement of the needle from the un-activated position to the activated position will generally simultaneously place the first end of the needle into fluid communication with the associated fluid reservoir while placing the second end of the needle into the patient.

Looking now to FIG. 1, the drug delivery device 10 includes a first drug reservoir or cartridge 12 and a second drug reservoir or cartridge 14. As such, the drug delivery device 10 (as well as other drug delivery devices described herein) may be considered a dual-cartridge device. Illustratively, the first medicament 20 is contained within the first reservoir 12 while the second medicament 22 is contained within the second reservoir 14. A first septum or stopper 24 is received in part within the inner chamber of the first reservoir 12 such that a portion of the first stopper 24 protrudes from a proximal end 25 of the first reservoir 12. The first stopper 24 includes a hollow chamber 26 in fluid communication with the first reservoir 12. Similarly, a second stopper 28 is received in part within the inner chamber of the second reservoir 14 such that a portion of the second stopper 28 protrudes from the proximal end 25 of the second reservoir 14. The second stopper 28 similarly includes the hollow chamber 26 in fluid communication with the second reservoir 14. Illustratively, the first and second stoppers 24, 28 may each be made from rubber. It is within the scope of this disclosure, however, for the first and second stoppers 24, 28 to be made from other suitable materials as well.

First and second needles 32, 34 of the drug delivery device 10 each include a first end 36 and a second end 38. The first end 36 of each needle 32, 34 is received through an outer wall of the respective first and second stoppers 24, 28 for positioning within the hollow chamber 26 of each stopper 24, 28. The second end 38 of each needle 32, 34 is provided for subcutaneous insertion into a patient in order to deliver the first and second medicaments 20, 22 to the patient. Illustratively, the first and second needles 32, 34 are shown to define a "J-shape" such that each needle 32, 34 includes an uptake arm 40 and a delivery arm 42 which are generally parallel to each other and a transverse arm 44 connecting the uptake and delivery arms 40, 42 together. Each arm 40, 42, 44 of each needle 32, 34 is cannulated to provide a generally continuous J-shaped passageway to allow the respective first and second medicaments 20, 22 to travel from the first end 36 of each needle 32, 34 to the second end 38 of each needle 32, 34.

As shown in FIG. 1, the arms 40, 42 of each needle 32, 34 have different lengths. It is within the scope of this disclosure, however, to include needles 32, 34 having arms 40, 42, 44 of varying or same lengths. It is also within the scope of this disclosure to include other needle designs where one end of the needle is positioned or able to be positioned within the hollow chamber 26 of one of the stoppers 24, 28 and where the other end of the needle is able to be subcutaneously inserted into a patient. Further, it is within the scope of this disclosure to include other infusion devices for delivering the medicaments 20, 22 from their respective reservoirs 12, 14 to the patient. For example, a lumen and a needle set, a catheter-cannula set, and/or a microneedle or microneedle array attached by one or more lumens may be used in place of the needles 32, 34. Further each of the fluid reservoirs 12, 14 may include an aperture through which the medicaments 20, 22 within each chamber are expelled. One of ordinary skill in the art will appreciate that many devices may be used to convey medicaments into a body. Accordingly, the present disclosure is not limited to the types of infusion or injection devices shown herein.

Looking again to FIG. 1, the drug delivery device 10 includes a first basal drive mechanism 46 which provides a basal delivery of the first medicament 20 to the patient. The first basal drive mechanism 46 includes a coil spring 48 secured to a basal drive piston 50. The basal drive piston 50 is positioned in the inner chamber of a basal fluid reservoir 52. The basal drive piston 50 is movable relative to the walls of the fluid reservoir 52. A pump chamber 54 is in fluid communication with the basal fluid reservoir 52 through a connective passageway or flow restrictor 56. The spring 48 exerts a generally constant force onto the basal drive piston 50 to assert pressure on the hydraulic fluid within the basal fluid chamber 52.

A driven or delivery piston 58 of the drug delivery device 10 is positioned within the inner chamber of the reservoir 12 and operates as a partition or movable barrier between the first medicament 20 contained within the first drug reservoir 12 and the hydraulic fluid contained within the pump chamber 56. Illustratively, the hydraulic fluid contained within the pump chamber 54 and the basal fluid reservoir 52 is an oil (not shown), or particularly a silicone oil, for example. However, these chambers may be filled with other non-compressible fluids as well such as those disclosed in U.S. Patent Application Publication US 2005/0119618, the disclosure of which is hereby incorporated by reference herein.

In operation, the coil spring 48 of the first basal drive mechanism 46 slowly expands to exert a bias on the basal drive piston 50 thereby exerting a force on the hydraulic fluid within the basal fluid reservoir 52 and the pump chamber 54. Such an increase in fluid pressure within the pump chamber 54 urges the delivery piston 58 to the right (as viewed in the orientation of FIG. 1). Such movement of the piston 50 causes a quantity of the first medicament 20 within the reservoir 12 to be forced through the needle 32 and delivered to a patient. The operation of such a basal drive mechanism is discussed in greater detail within U.S. Patent Application Publication No. US 2005/0119618.

The drug delivery device 10 further includes a second basal drive mechanism 60 which provides a basal delivery of the second medicament 22 to the patient. The second basal drive mechanism 60 is the same as or similar to the first basal drive mechanism 46. As such, like reference numerals have been used to denote like components. For example, the second basal drive mechanism 60 includes the coil spring 48 secured to the basal drive piston 50. The basal fluid reservoir 52 of the second basal system is in fluid communication with the pump chamber 54 through the connective passageway or flow restrictor 56. Similarly, the fluid reservoir 52, pump reservoir 54, and flow restrictor 56 associated with the second medicament are each filled with an oil such as a silicone oil, for example. Further, the second basal drive mechanism 60 operates the same as or similarly to the first basal drive mechanism 46 to force the second medicament 22 from within the second reservoir 14 through the needle 34 and into a patient.

As discussed above, the fluid delivery device 10 includes two separate basal drive mechanisms 46, 60 to provide a basal delivery of each of the first and second medicaments 20, 22. In operation, a single button or actuator may be activated by a user to actuate both of the first and second drive mechanisms 46, 60 at one time. Of course, separate actuators may be used to independently actuate each of the drive mechanisms 46, 60 as well. Illustratively, such button(s) or actuator(s) may be located on or within the outer housing (not shown) of the fluid delivery device 10 to be activated by a user or patient.

Looking still to FIG. 1, a single bolus drive mechanism 62 is used to provide a bolus delivery of each of the first and second medicaments 20, 22. The bolus drive mechanism 62 includes a ratchet 64 having a toothed rack 66 and a pawl 68 engaged with the teeth of the toothed rack 66. The toothed rack 66 is coupled to a dual-head piston assembly 70 including first and second arms 72, 74 spaced-apart from each other by a transverse arm 76 coupled to both the first and second arms 72, 74. Illustratively, the toothed rack 66 of the ratchet 64 is coupled to the transverse arm 76. A bolus drive piston 78 is coupled to each of the first and second arms 72, 74 of the dual-head piston assembly 70. Each of the pistons 78 is positioned within an interior chamber of one or a pair of bolus delivery reservoirs 80. The bolus delivery reservoirs 80 are in fluid communication with their respective pump chambers 54.

In operation, a force applied to the toothed rack 66 advances the dual-head piston assembly 70 to force fluid from each bolus fluid reservoir 80 into the respective pump chamber 54 to move the respective driven piston 58 thereby causing bolus delivery of both the first and second medicaments 20, 22 from the respective first and second drug reservoirs 12, 14. A bolus actuator button may be coupled to the toothed rack 66 such that when a user depresses the bolus actuator button, the toothed rack 66 is advanced a pre-determined distance. Alternatively, such a bolus actuator button may be coupled to the pawl 68 such that when a user depresses the bolus actuator button, the pawl 68 is advanced a predetermined distance and forces the toothed rack 66 to advance the same predetermined distance as well. With such an arrangement, a secondary mechanism may be used to retract the pawl 68 relative to the toothed rack 66 to an activated position such that the pawl 68 may be advanced again to provide another bolus delivery. In either case, the pawl 68 of the ratchet 64 prevents the toothed rack 66 from moving backward after having been advanced. Further, the pawl 68 of the ratchet 64 prevents the toothed rack 66 from moving backward due to any increased fluid pressure caused by fluid moving from the basal fluid reservoirs 52 into the pump chambers 54, for example.

As described above, the fluid delivery device 10 includes two separate fluid reservoirs 12, 14 containing two different medicaments 20, 22 therein. Illustratively, separate needles 32, 34 are provided to deliver each medicament 20, 22 to a patient. However, it is within the scope of this disclosure to include a single needle for delivering each of the first and second medicaments 20, 22. Such embodiments are discussed in greater detail below.

Figure 2:
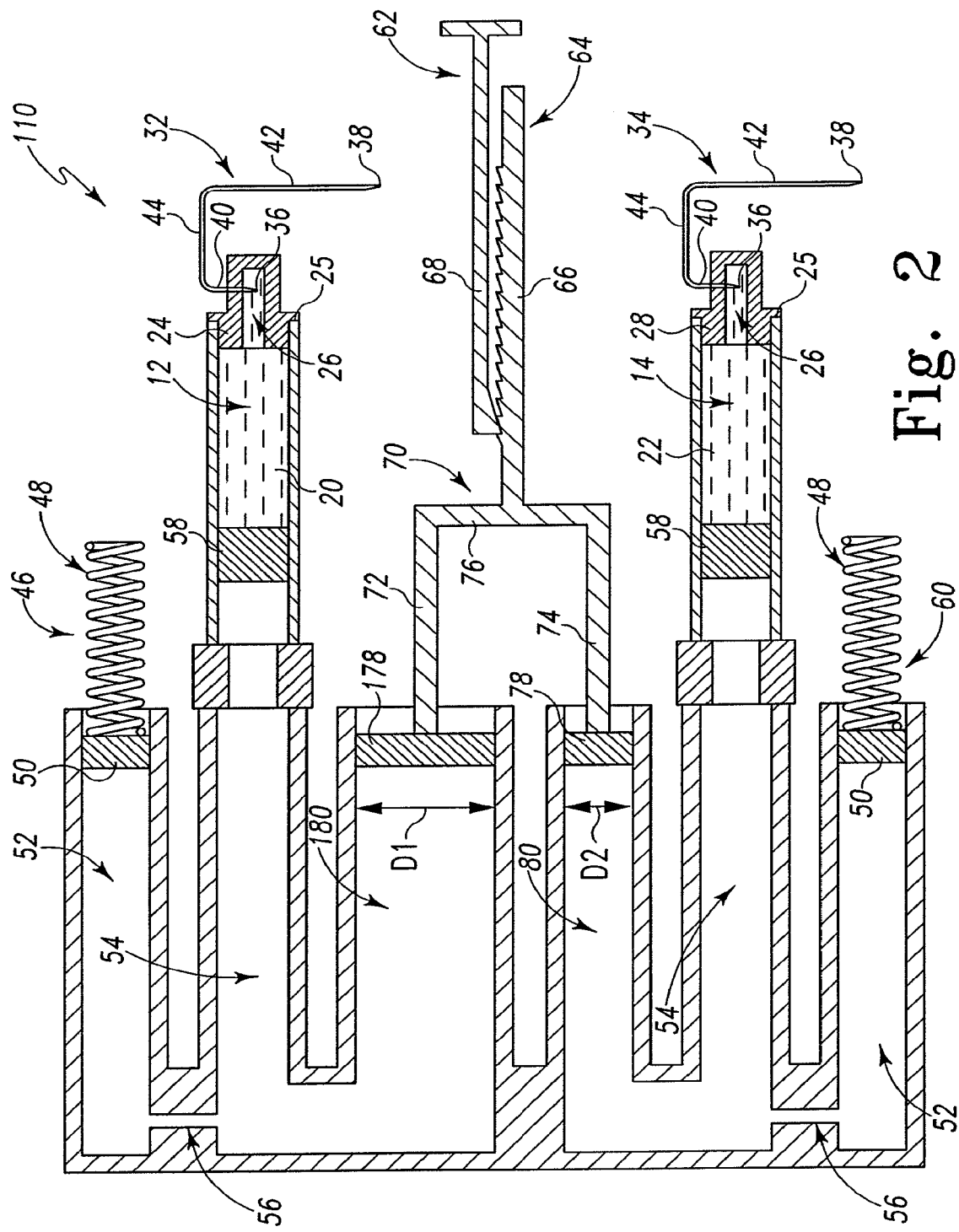

Looking now to FIG. 2, a fluid delivery device 110 is similar to the fluid delivery device 10 described above. As such, the same reference numerals have been used to denote the same or similar components. The fluid delivery device 110 includes a first bolus piston 178 positioned within a first bolus reservoir 180. The bolus piston 178 is larger than the bolus piston 78. Specifically, the first bolus piston 178 has a diameter D1 that is greater than the diameter D2 of the second bolus piston 78. As such, the bolus piston 178 has a greater surface area than the second bolus piston 78. The disparity in size between the first and second bolus pistons 78, 178 produces a different bolus delivery (e.g. quantity or amount of medicament being delivered) of each of the first and second medicaments 20, 22 in response to movement of the dual head piston assembly 70.

In other words, the concerted movement of the pistons 78, 178 operates to displace a different amount of fluid from the respective bolus reservoirs 80, 180 to act on the driven piston 58 associated with each of the first and second reservoirs 12, 14. This causes a greater pressure to be exerted on the piston 58 associated with the reservoir 12 relative to the pressure associated with the reservoir 14. This in turn causes a larger bolus delivery of the first medicament 20 to be delivered relative to the bolus delivery of the second medicament 22. Therefore, an incremental movement of the dual-head piston assembly 70 of the bolus drive mechanism 62 will cause a greater amount of the first medicament 20 to be delivered to the patient than the second medicament 22.

In many instances, for example, it may be preferable to deliver a first amount of a first medicament with a second amount of a second medicament. Varying the size of the bolus drive piston, therefore, allows the ratio of the two medicaments delivered in a bolus delivery to be varied. In other words, it is within the scope of this disclosure to vary the size of the bolus pistons of the fluid delivery devices described herein in order to achieve any desired bolus delivery ratio between the two medicaments being delivered to a patient.

As is discussed in greater detail below, the size of other components associated with the fluid delivery device (e.g., drive pistons, flow restrictors, etc.) may also be varied in order to basally deliver the first medicament at a different rate than the second medicament. Again, any of these dimensions may be configured in order to produce a desired ratio between the basal delivery rates of the first and second medicaments.

Figure 3:
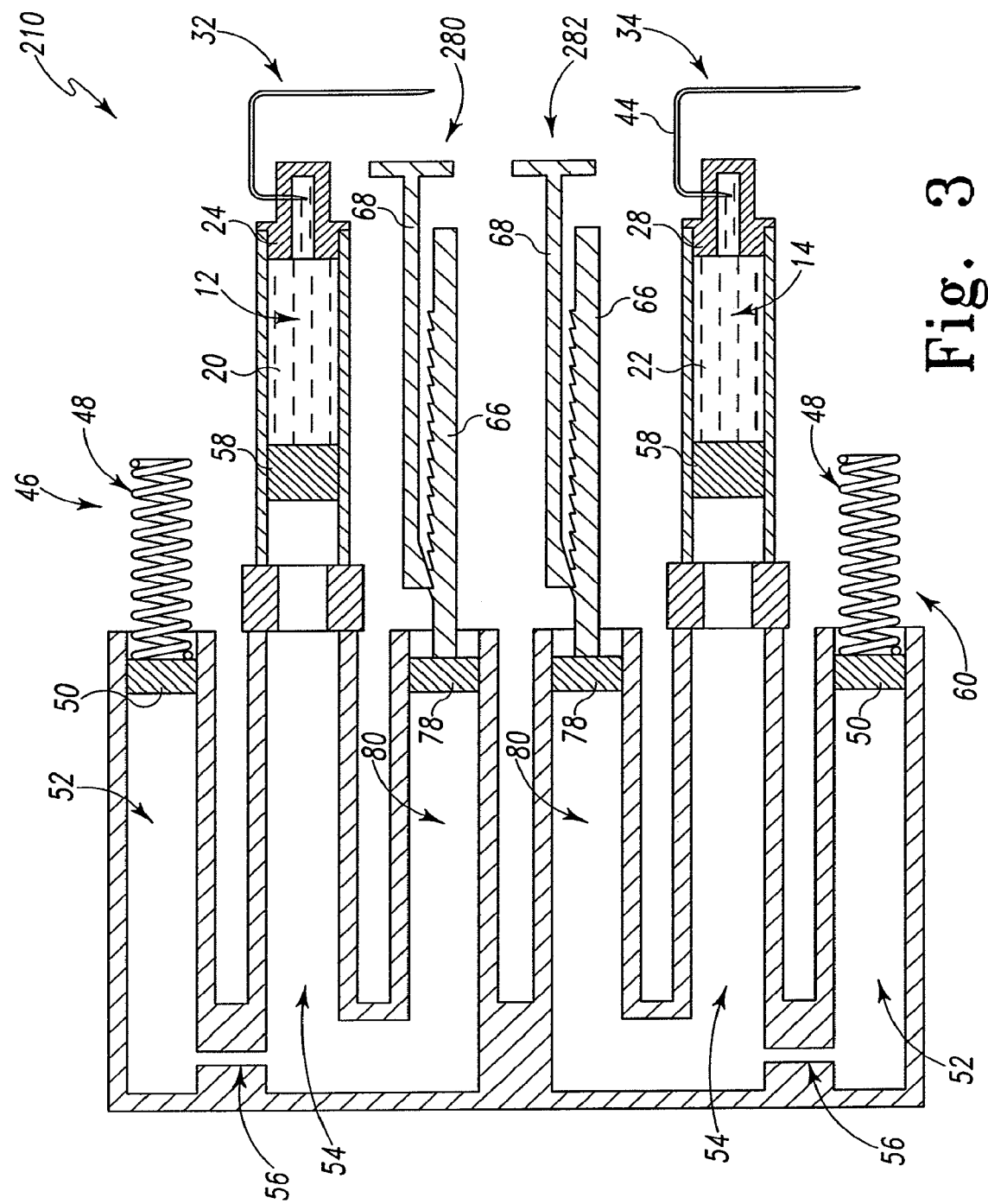

Looking now to FIG. 3, another fluid delivery device 210 is provided. Again, the fluid delivery device 210 is similar to devices 10, 110 described above. As such, like reference numerals have been used to denote like components. The fluid delivery device 210 includes a first bolus drive mechanism 280 and a second bolus drive mechanism 282. Each of the first and second bolus drive mechanisms 280, 282 includes a ratchet 64 having a toothed rack 66 and a pawl 68 engaged with the teeth of the toothed rack 66. Each bolus drive mechanism 280, 282 further includes a piston 78 coupled to one end of each toothed rack 66 and positioned within an inner chamber of the respective bolus fluid reservoirs 80. As such, the bolus delivery feature of each medicament 20, 22 is operated independently by separate bolus drive mechanisms 280, 282.

In operation, the bolus drive mechanisms 280, 282 may, therefore, be actuated independently to separately advance each of the toothed racks 66 of the separate bolus drive mechanisms 280, 282 enabling a user to provide one bolus delivery of one of the medicaments 20, 22 without providing a bolus delivery of the other medicament 20, 22. For example, actuation by a user of the first bolus drive mechanism 280 provides a bolus delivery of only the first medicament 20 while actuation of the second bolus drive mechanism 282 provides a bolus delivery of only the second medicament 22. Of course, the bolus drive mechanisms 280, 282 may also be actuated by a single actuator (not shown) which is able to advance each of the toothed racks 186 at the same time.

Figure 4:
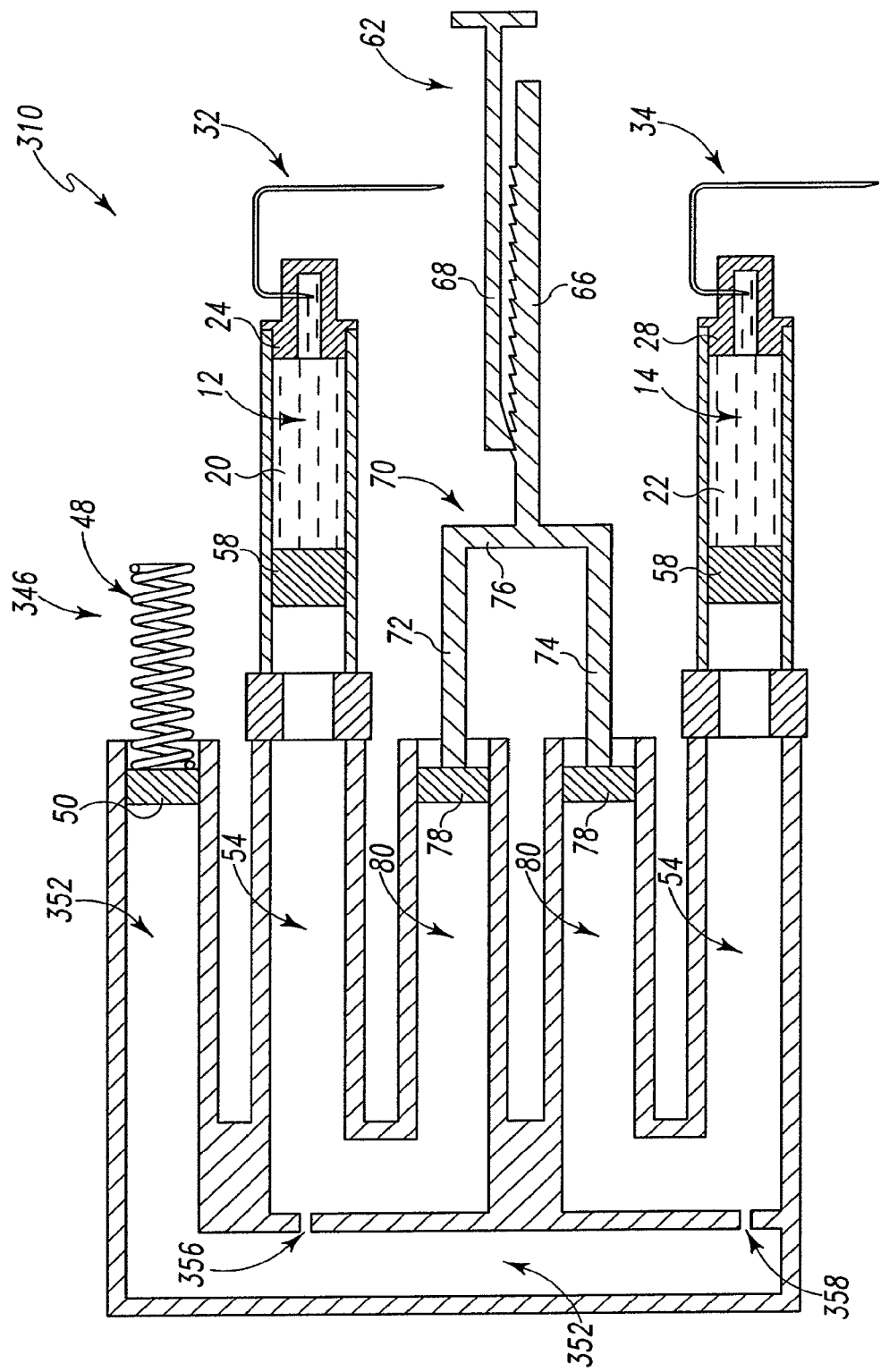

Looking now to FIG. 4, the fluid delivery device 310 is provided. The delivery device 310 is similar to the delivery devices 10, 110, and 210 described above. As such, like reference numerals have been used to denote like components. The fluid delivery device 310 includes a single basal drive mechanism 346 having the coiled spring 48 and the basal drive piston 50. A basal fluid reservoir 352 is in fluid communication with both the respective pump chambers 54 associated with each of the first and second drug reservoirs 12, 14. Illustratively, a first flow restrictor 356 is positioned between the fluid reservoir 352 and the pump chamber 54 associated with the first reservoir 12. A second flow restrictor 358 is positioned between the fluid reservoir 352 and the pump chamber 54 associated with the second reservoir 14. Illustratively, the first flow restrictor 356 is positioned upstream of the second flow restrictor 358. It is within the scope of this disclosure, however, to provide a similar fluid delivery device wherein the flow restrictor associated with the second medicament is positioned upstream from the flow restrictor associated with the first medicament or alternatively where the two flow restrictors are in parallel with each other. In other words, the position or location of the flow restrictor associated with each of the first and second basal drive mechanisms may be altered as desired.

The single basal drive mechanism 346 of the fluid delivery device 310 drives the basal delivery for both the first and second medicaments 20, 22. Thus, actuation of the drive mechanism 346 to permit the coil spring 48 to advance the basal drive piston 50 will cause both of the driven pistons 58 to advance as well. Illustratively, the size (including diameter, or width, and length) of each of the flow restrictors 356, 358, the pump chambers 54, the pistons 58, and the drug reservoirs 12, 14 are shown to be generally the same. As such, the rate of basal delivery of the first and second medicaments 20, 22 will generally be the same or similar. However, it should be appreciated that varying one or more of the dimensions of one or more of the aforementioned components associated with either medicament 20, 22 will provide a fluid delivery device which is capable of delivering the first medicament 20 at a first basal delivery rate while the second medicament 22 is delivered at a second basal delivery rate different from the first basal delivery rate. In such a scenario, these differing basal delivery rates are provided with the use of a single basal drive mechanism.

According to another aspect of the present disclosure, a fluid delivery device (not shown) similar to the fluid delivery device 310 of FIG. 4 may similarly include a single basal drive mechanism for providing a basal delivery of each of the first and second medicaments 20, 22. However, such a fluid delivery device may include a basal fluid reservoir in communication with a single pump chamber via a single flow restrictor. A tail end of a generally Y-shaped piston (not shown) may be received within the single pump chamber while each spaced-apart arm of the Y-shaped piston may be received within the fluid reservoir 12, 14 containing the respective medicaments 20, 22.

As such, the drive mechanism operates to expel hydraulic fluid, such as silicone oil, for example, from the basal fluid reservoir, through the flow restrictor, and into the pump chamber to act upon the tail end of the Y-shaped piston. This force on the Y-shaped piston causes the piston to thereby expel the first and second medicaments 20, 22 from the reservoirs 12, 14. In such a fluid delivery system, a single bolus drive mechanism may also actuate bolus delivery of each of the first and second medicaments. Further, piston arms having a different size or different cross-sectional surface area relative to one another provides for a different basal delivery and a different bolus delivery between the two medicaments 20, 22.

Illustratively, the fluid delivery device 310 shown in FIG. 4 includes the single bolus drive mechanism 62 similar to that shown in FIGS. 1 and 2 for providing bolus delivery of both the first and second medicaments 20, 22. However, a fluid delivery device, such as the fluid delivery device 410 shown in FIG. 5a, may be provided which includes the single basal drive mechanism 346 shown in FIG. 4 and separate bolus drive mechanisms 280, 282 similar to those shown in FIG. 3.

Figure 5A:
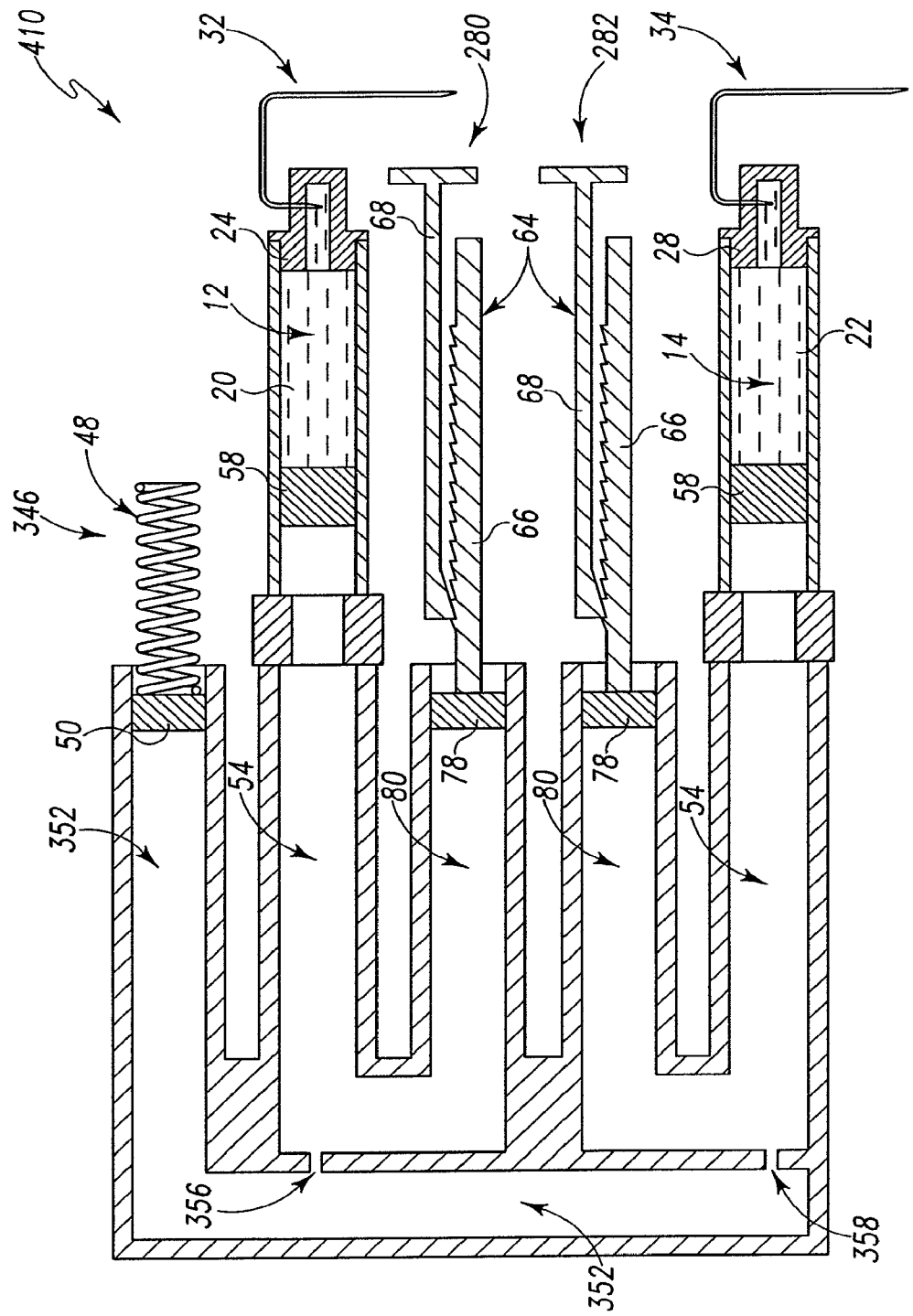
Figure 5B:
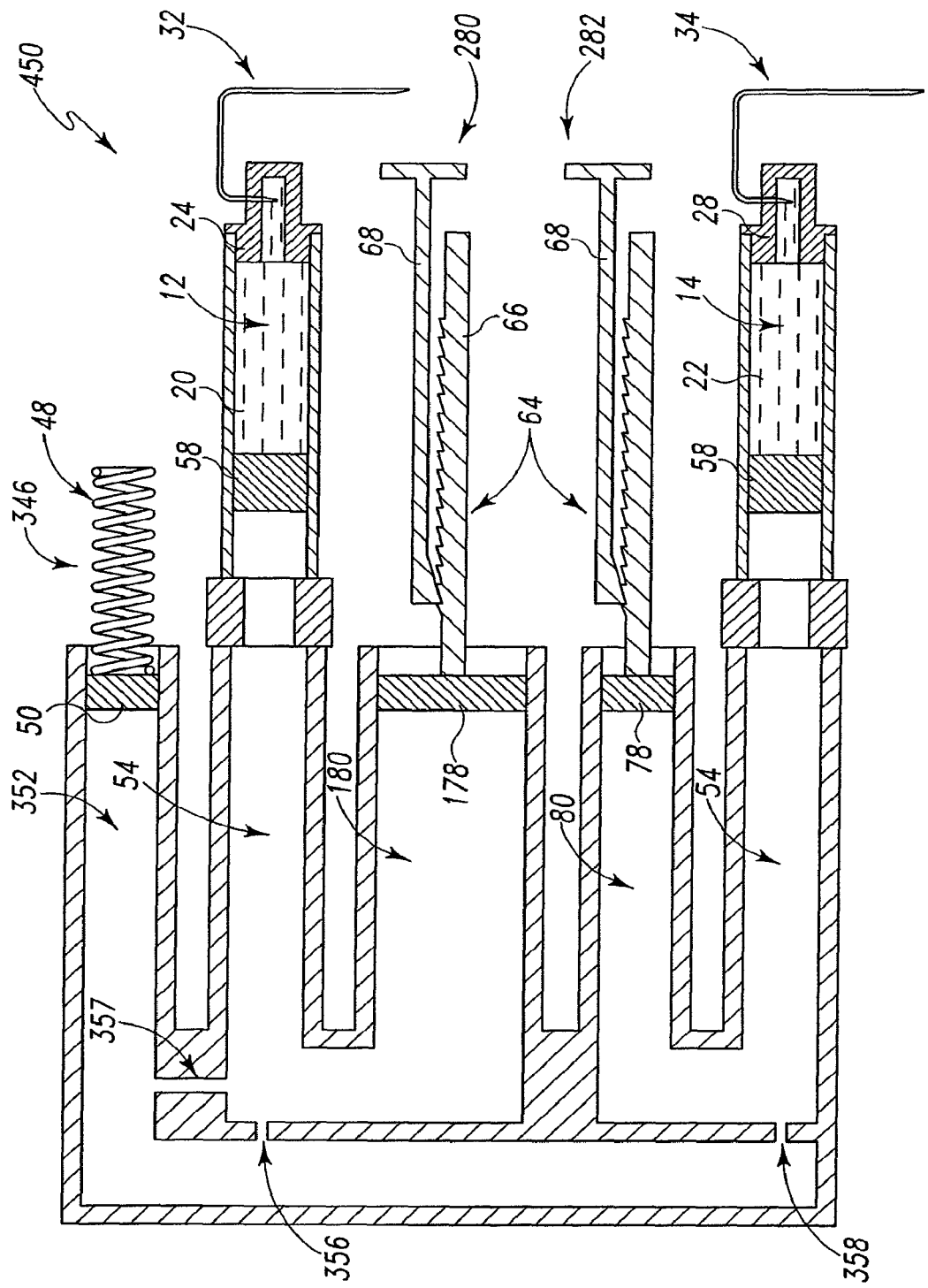

Further, a fluid delivery device 450, shown in FIG. 5b, is similar to the fluid delivery device 410 shown in FIG. 5a. For example, the device 450 similarly includes a single basal drive mechanism 346 and provides a basal delivery of each of the first and second medicaments 20, 22 while two separate bolus drive mechanisms 280, 282 provide a bolus delivery of each of the first and second medicaments 20, 22. Illustratively, however, two flow restrictors 356, 357 fluidly connect the basal fluid reservoir 352 with the pump chamber 54 associated with the first reservoir 12. A single flow restrictor 358 is provided between the basal fluid reservoir 352 and the pump chamber 54 associated with the second reservoir 14. The dual flow restrictors 356, 357 allow additional hydraulic fluid (not shown) from the basal fluid reservoir 352 to enter the pump chamber 54 associated with the first reservoir 12. As such, a greater pressure is exerted on the drive piston 58 associated with the first reservoir 12 than that which is exerted on the drive piston 58 associated with the second reservoir 14. This in turn causes a larger basal delivery (i.e., a greater rate of delivery) of the first medicament 20 to be delivered relative to the basal delivery of the second medicament 22. Other systems may be provided including any number of flow restrictors connecting the fluid reservoir 352 with either one of the pump chambers 54.

As discussed above, each of the fluid delivery devices 10, 110, 210, 310, 410, and 450 are able to provide both a basal delivery and a bolus delivery of the first medicament 20 as well as both a basal delivery and a bolus delivery of the second medicament 22. This function may be accomplished through various combinations of various features of these devices 10, 110, 210, 310, 410, and 450. For example, the fluid delivery device 10 includes two separate basal drive mechanisms and a single bolus drive mechanism able to provide a bolus delivery of each of the first and second medicaments 20, 22. The fluid delivery device 210 of FIG. 3, on the other hand, includes two separate basal drive mechanisms and two separate bolus drive mechanisms. The fluid delivery device 310 of FIG. 4 includes only one basal delivery mechanism and one bolus delivery mechanism while the fluid delivery devices of FIGS. 5a and 5b include a single basal delivery mechanism and two separate bolus delivery mechanisms.

As noted above, the fluid delivery device 110 of FIG. 2 illustrates a size difference between the surface area of the bolus drive pistons 178, 78 associated with each of the first and second reservoirs 12, 13 in order to provide a different bolus delivery of each of the first and second medicaments 20, 22 using the single bolus drive mechanism 62. As was mentioned previously, the dimension(s) of many other components of the various fluid delivery devices 10, 110, 210, 310, 410 and 450 may be varied in order to provide a device wherein the basal and/or bolus deliveries of the first and second medicaments 20, 22 are different from each other.

Figure 6:
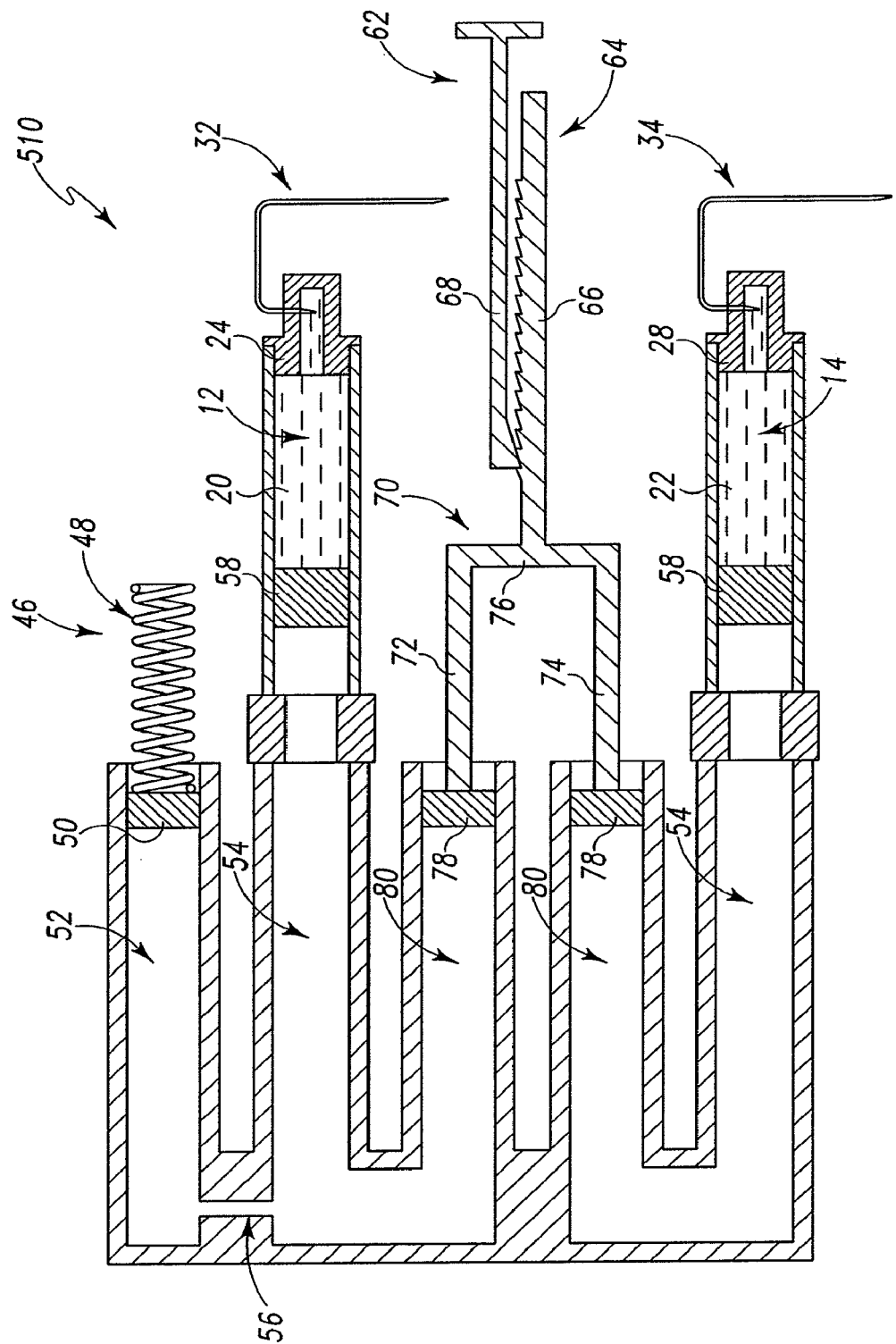
FIGS. 6-7 are schematics showing additional drug delivery devices of the present disclosure which provide a basal delivery of the first medicament only and a bolus delivery of the first and second medicaments.
Figure 7:
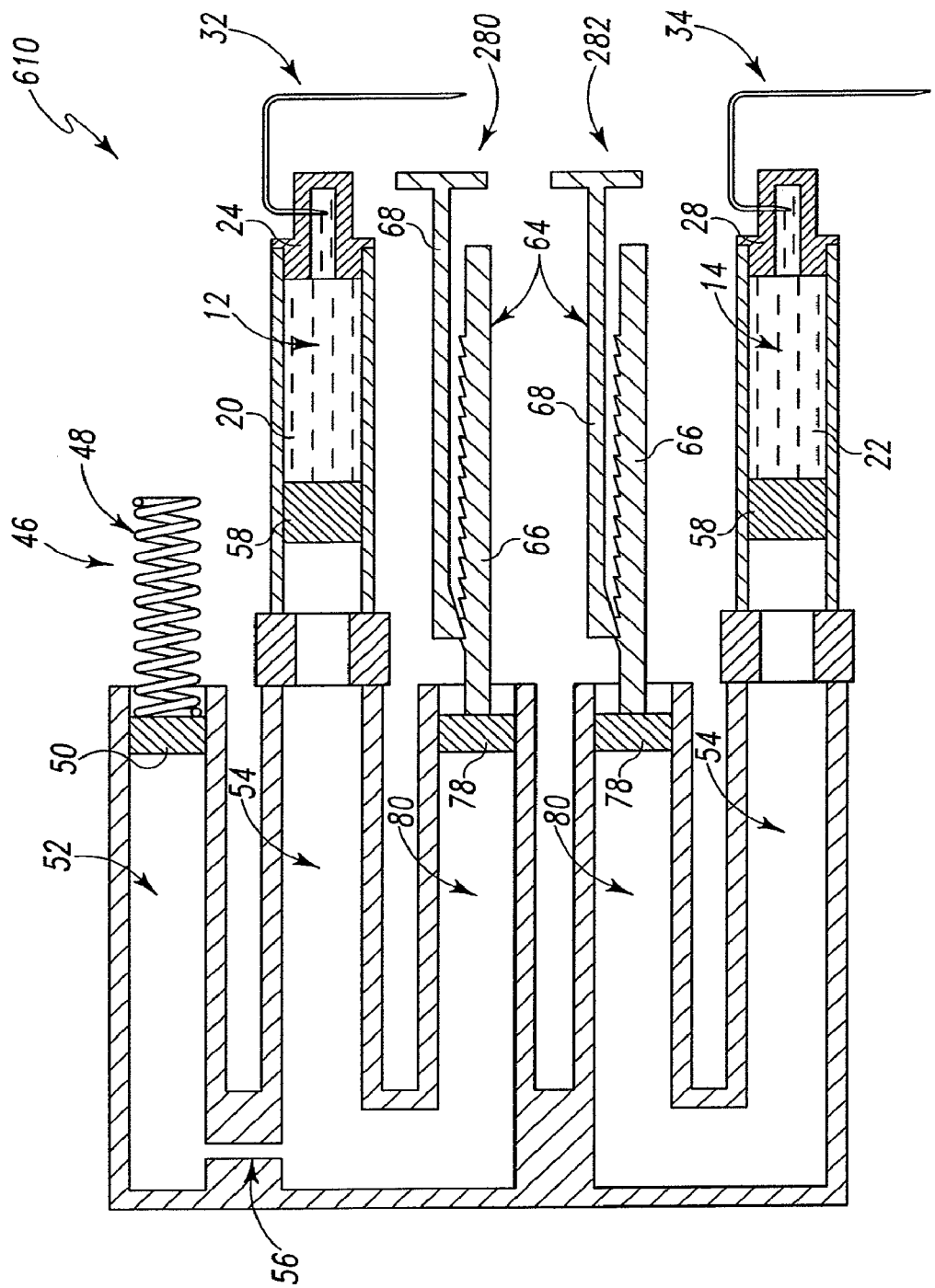

Looking now to FIGS. 6 and 7, fluid delivery devices 510 and 610 are provided. The fluid delivery devices 510, 610 are similar in nature to the fluid delivery devices described above in FIGS. 1-5b. As such, like reference numerals have been used to denote like components. Each of the fluid delivery devices 510 and 610 provides a basal delivery of only one medicament, illustratively, the first medicament 20. In other words, neither of the fluid delivery devices 510, 610 shown in FIGS. 6 and 7 provides a basal delivery of the second medicament 22. However, a bolus delivery of each medicament 20, 22 is provided. This arrangement may be beneficial for the use of various combinations of first and second medicaments where a basal delivery is necessary for only one medicament, but where a bolus delivery of each medicament is desired. Of course, the fluid delivery devices 510, 610 may instead be configured to provide a basal delivery of only the second medicament 22.

Looking first to FIG. 6, the fluid delivery device 510 includes one basal drive mechanism 46 for providing a basal delivery of the first medicament 20. The fluid delivery device 510 further includes one bolus drive mechanism 62 for providing a bolus delivery of each of the first and the second medicaments 20, 22. The fluid delivery device 610 of FIG. 7 includes one basal drive mechanism 46 for providing a basal delivery of the first medicament 20. The fluid delivery device 610 further includes the first bolus drive mechanism 280 for providing a bolus delivery of the first medicament 20 and the second bolus drive mechanism 282 for providing a bolus delivery of the second medicament 22. Of course, the dimension(s) of many of the components of the fluid delivery devices 510, 610 may be varied in order to provide a device wherein the bolus delivery of the first and second medicaments 20, 22 are different from each other.

Figure 8:
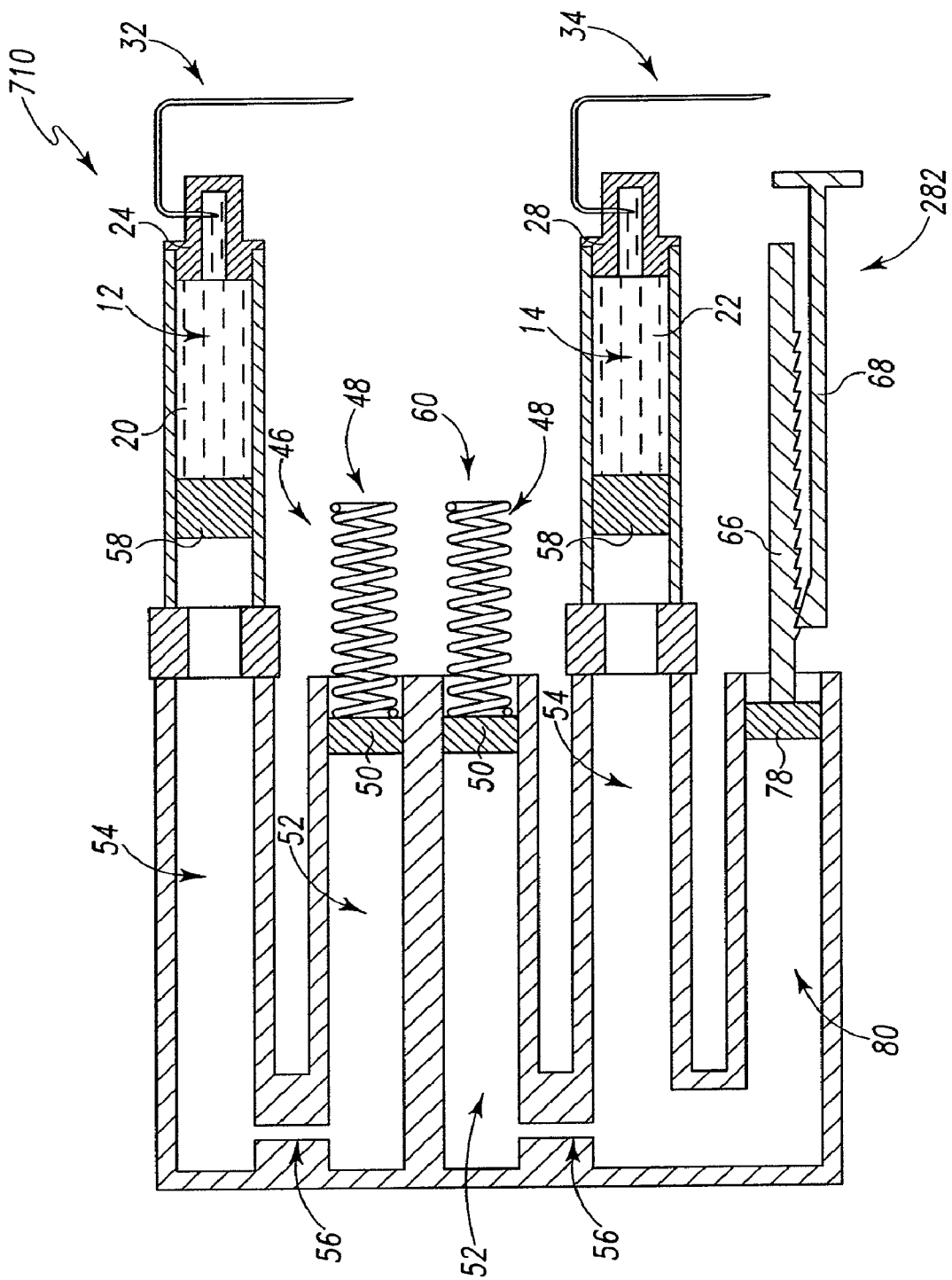
FIGS. 8-9 are schematics further showing additional drug delivery devices of the present disclosure which provide a basal delivery of the first and second medicaments while providing a bolus delivery of only the second medicament.
Figure 9:
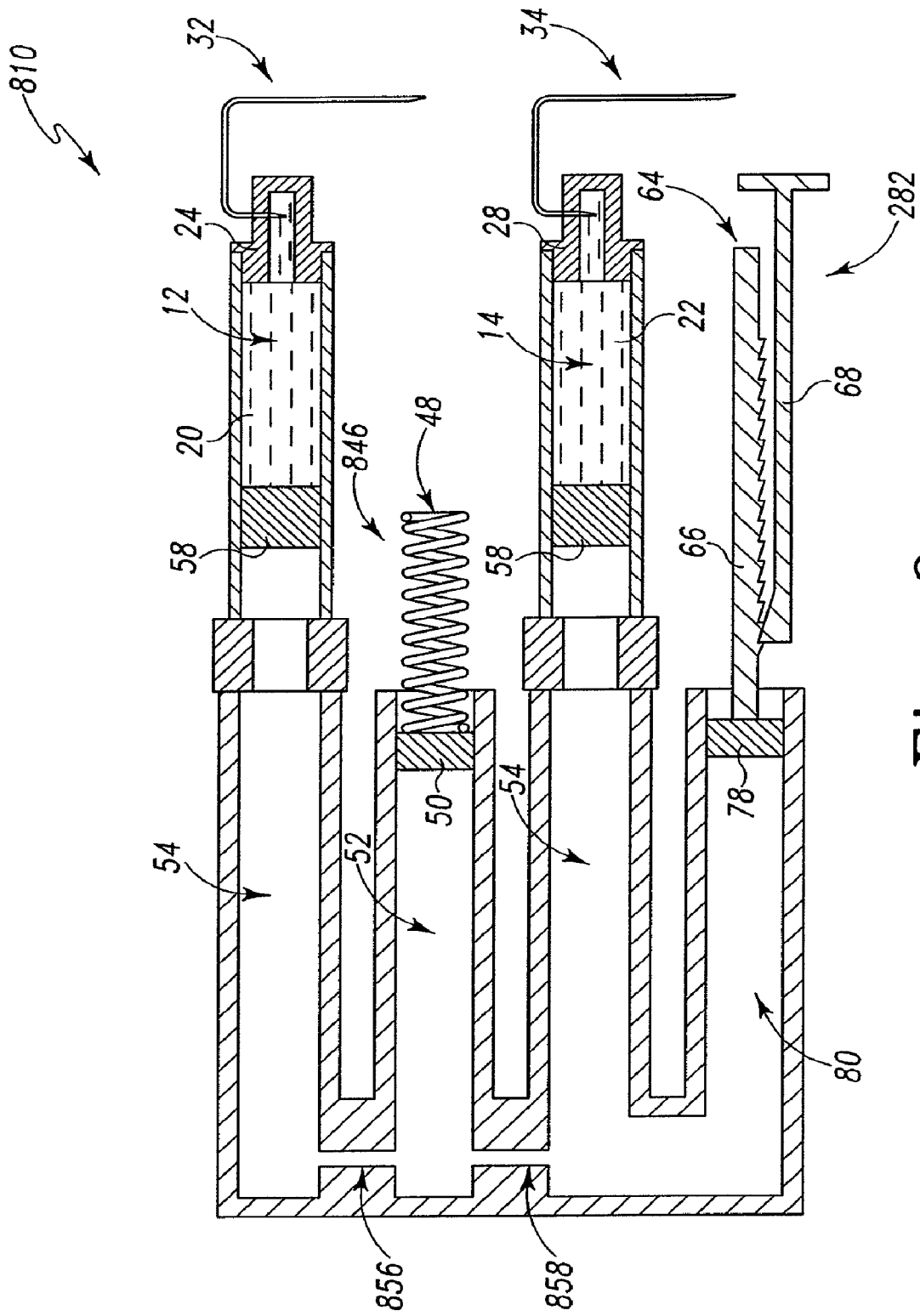

Looking now to FIGS. 8 and 9, fluid delivery devices 710 and 810 are provided. Each of these fluid delivery devices 710, 810 are similar to the fluid delivery devices described above. As such, like reference numerals are used to denote like components. The fluid delivery devices 710, 810 shown in FIGS. 8 and 9 each provide a basal delivery of the first and second medicaments 20, 22 while providing a bolus delivery of only the second medicament 22. No bolus delivery function is provided for the first medicament 20. Of course, the fluid delivery devices 710, 810 may be modified to provide a bolus delivery of the first medicament 20 only. Such an arrangement may be beneficial where it is desired to basally deliver two different medicaments to a patient while providing a bolus delivery of only one of the two medicaments.

Looking first to FIG. 8, the fluid delivery device 710 includes the first basal drive mechanism 46 to provide basal delivery of the first medicament 20 and the second basal drive mechanism 60 to provide basal delivery of the second medicament 22. The single bolus delivery mechanism 282 provides the bolus delivery of the second medicament 22. Illustratively, the bolus fluid reservoir 80 is in fluid communication with the pump chamber 54 associated with the second reservoir 14. As such, advancement of the toothed gear 66 of the bolus drive mechanism 282 to advance the bolus drive piston 78 exerts a pressure on the driven piston 58 to advance the driven piston 58 and to deliver a bolus amount of the second medicament 22 through the needle 34.

Similar to the fluid delivery device 710, the fluid delivery device 810 shown in FIG. 9 provides a basal delivery of the first and second medicaments 20, 22 while providing a bolus delivery of only the second medicament 22. The basal delivery of both of the first and second medicaments 20, 22 is provided through the use of a single basal drive mechanism 846. A first flow restrictor 856 fluidly connects the basal fluid reservoir 52 and the pump chamber 54 associated with first drug reservoir 12 while a second flow restrictor 858 fluidly connects the basal fluid reservoir 52 and the pump chamber 54 associated with the second drug reservoir 14.

Further illustratively, the basal drive mechanism 846 is positioned between the pump chambers 54 and the first and second drug reservoirs 12, 14 containing the first and second medicaments 20, 22. As such, neither flow restrictor 856, 858 is positioned upstream or downstream from the other. While the single basal drive mechanism 846 is provided, it is also within the scope of this disclosure for the fluid delivery device 810 to include the single basal drive mechanism 346 shown in FIGS. 4 and 5, for example. The bolus drive mechanism 282 of the fluid delivery device 810 provides a bolus delivery of only the second medicament 22. Of course, the dimension(s) of many of the components of the fluid delivery devices 710, 810 may be varied in order to provide a device wherein the basal delivery of the first and second medicaments 20, 22 are different from each other.

Figure 10:
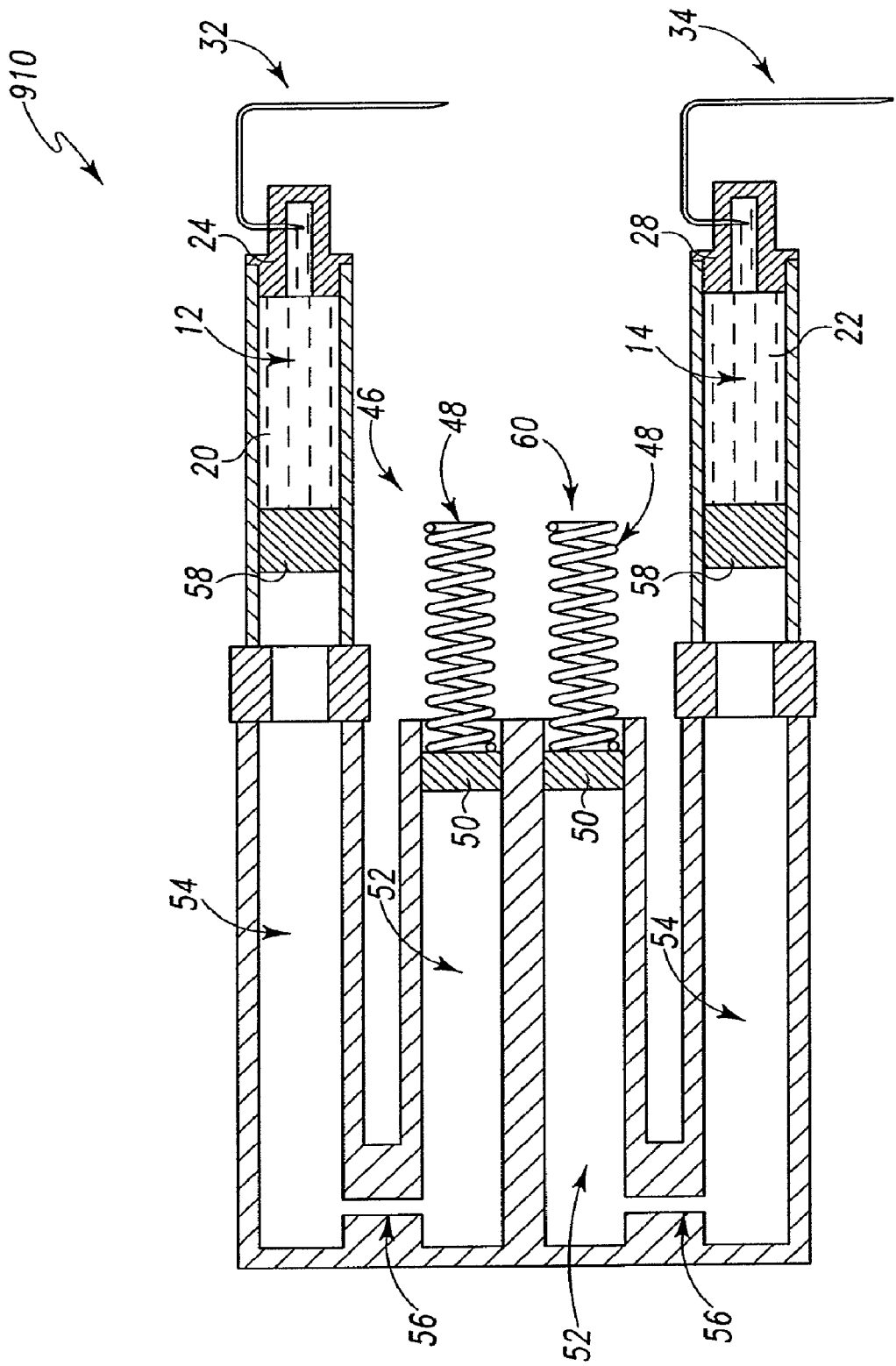
FIGS. 10-11 are schematics showing further drug delivery devices of the present disclosure which provide a basal delivery of the first and second medicaments while providing no bolus delivery for either of the first or second medicaments.
Figure 11:
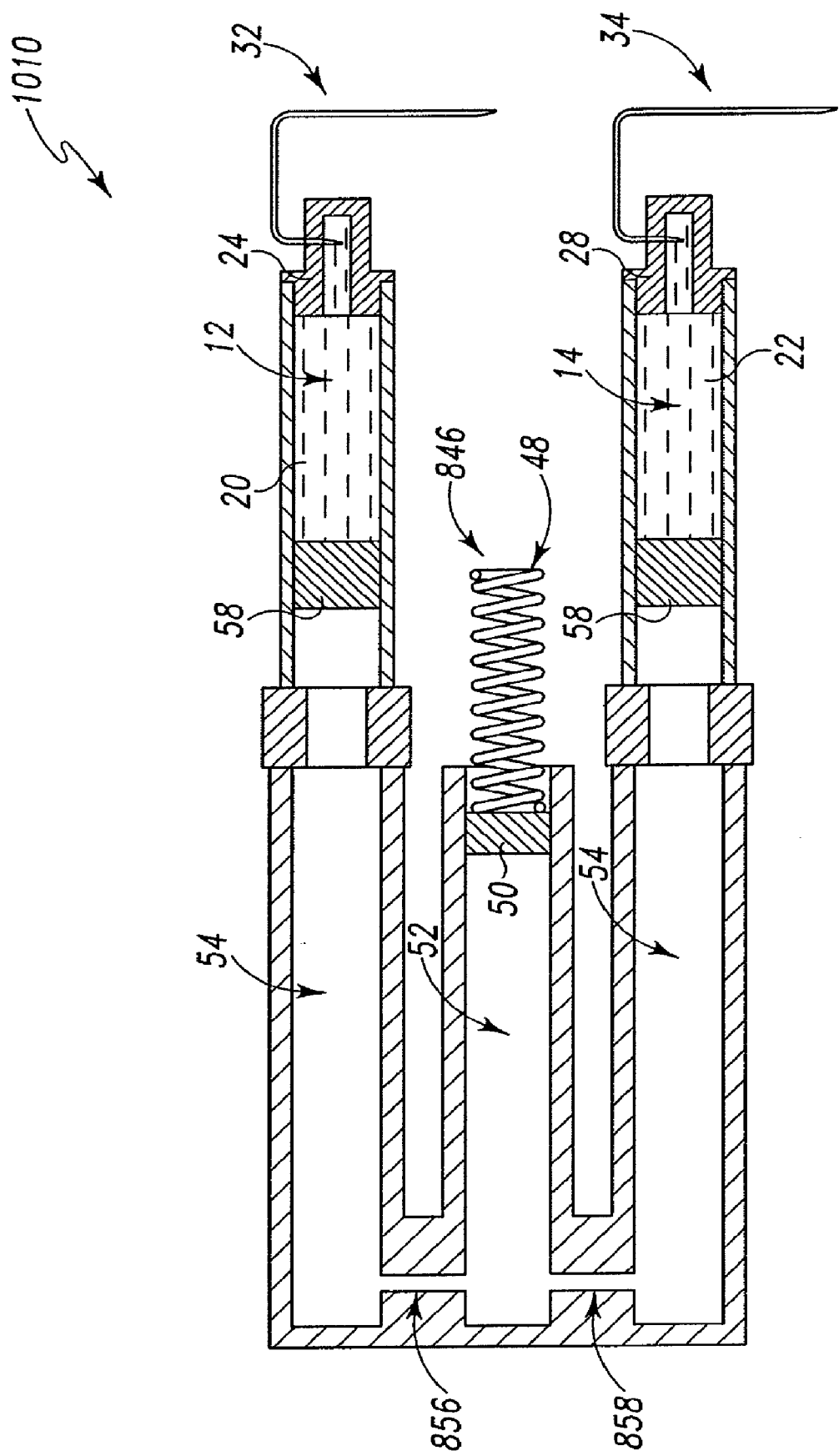

Looking now to FIGS. 10 and 11, fluid delivery devices 910, 1010 of the present disclosure are provided. Devices 910, 1010 are similar to the fluid delivery devices discussed above. As such, like reference numerals are used to denote like components. Each of the fluid delivery devices 910, 1010 provides only a basal delivery of both the first and second medicaments 20, 22. Therefore, looking first to FIG. 10, the fluid delivery device 910 includes the first and second basal drive mechanisms 46, 60 associated with the respective first and second drug reservoirs 12, 14 to provide independent basal delivery of each of the first and second medicaments 20, 22. No bolus function is provided for either the first or second medicaments 20, 22. Illustratively, the fluid delivery device 910 shown in FIG. 10 provides the basal delivery of the first and second medicaments 20, 22 using two separate basal drive mechanisms 46, 60. However, a single basal drive mechanism 846 may be used to provide the basal delivery of the first and second medicaments 20, 22, as shown by the fluid delivery device 1010 in FIG. 11, for example. Again, no bolus delivery function is provided for the device 1010 of FIG. 11. Of course, the dimension(s) of many of the components of the fluid delivery devices 910, 1010 may be varied in order to provide a device wherein the basal delivery of the first medicament 20 is different from the basal delivery of the second medicaments 22.

Figure 12:
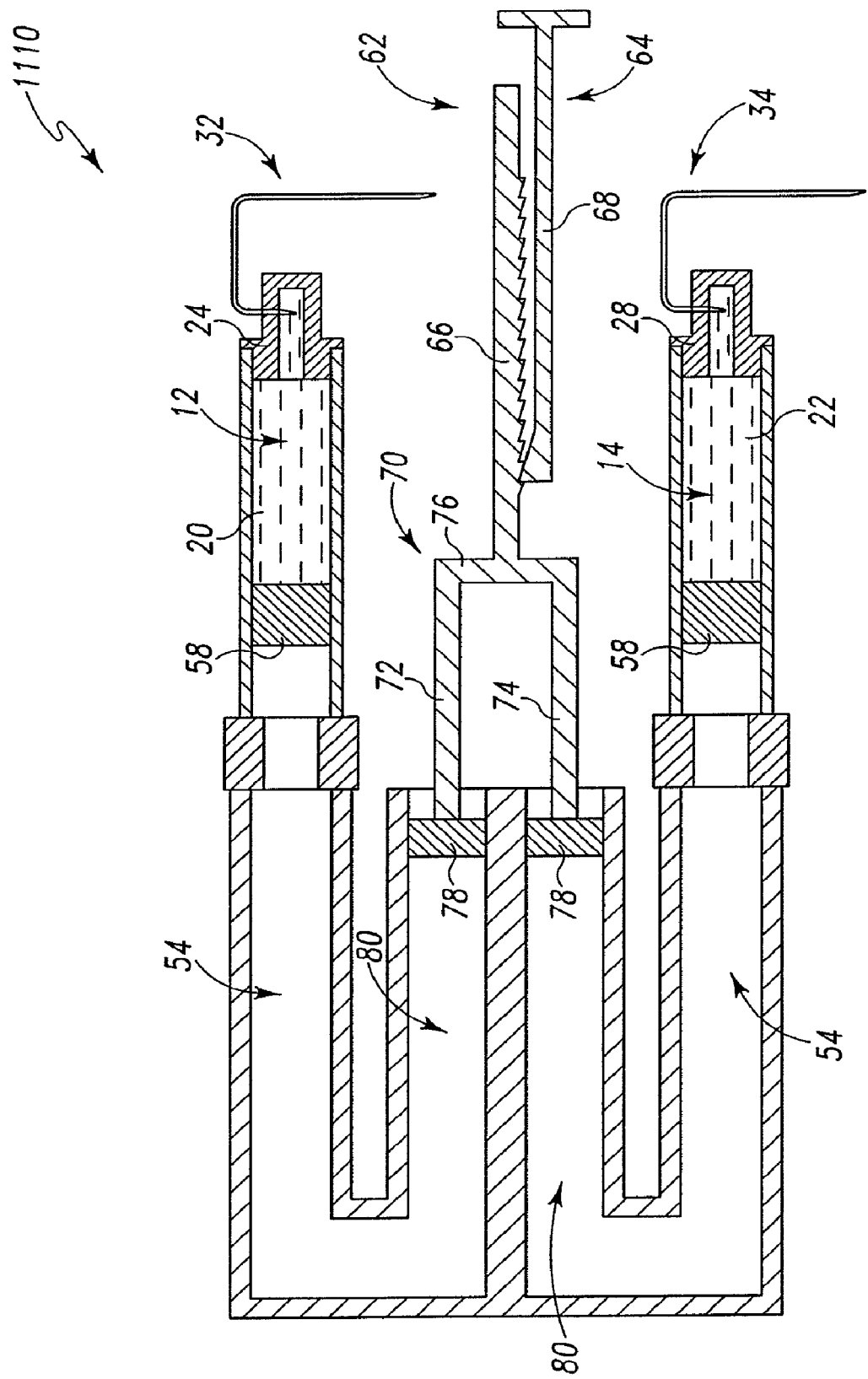
FIGS. 12-13 are schematics showing additional drug delivery devices of the present disclosure which provide a bolus delivery of the first and second medicaments while providing no basal delivery for either of the first or second medicaments.
Figure 13:
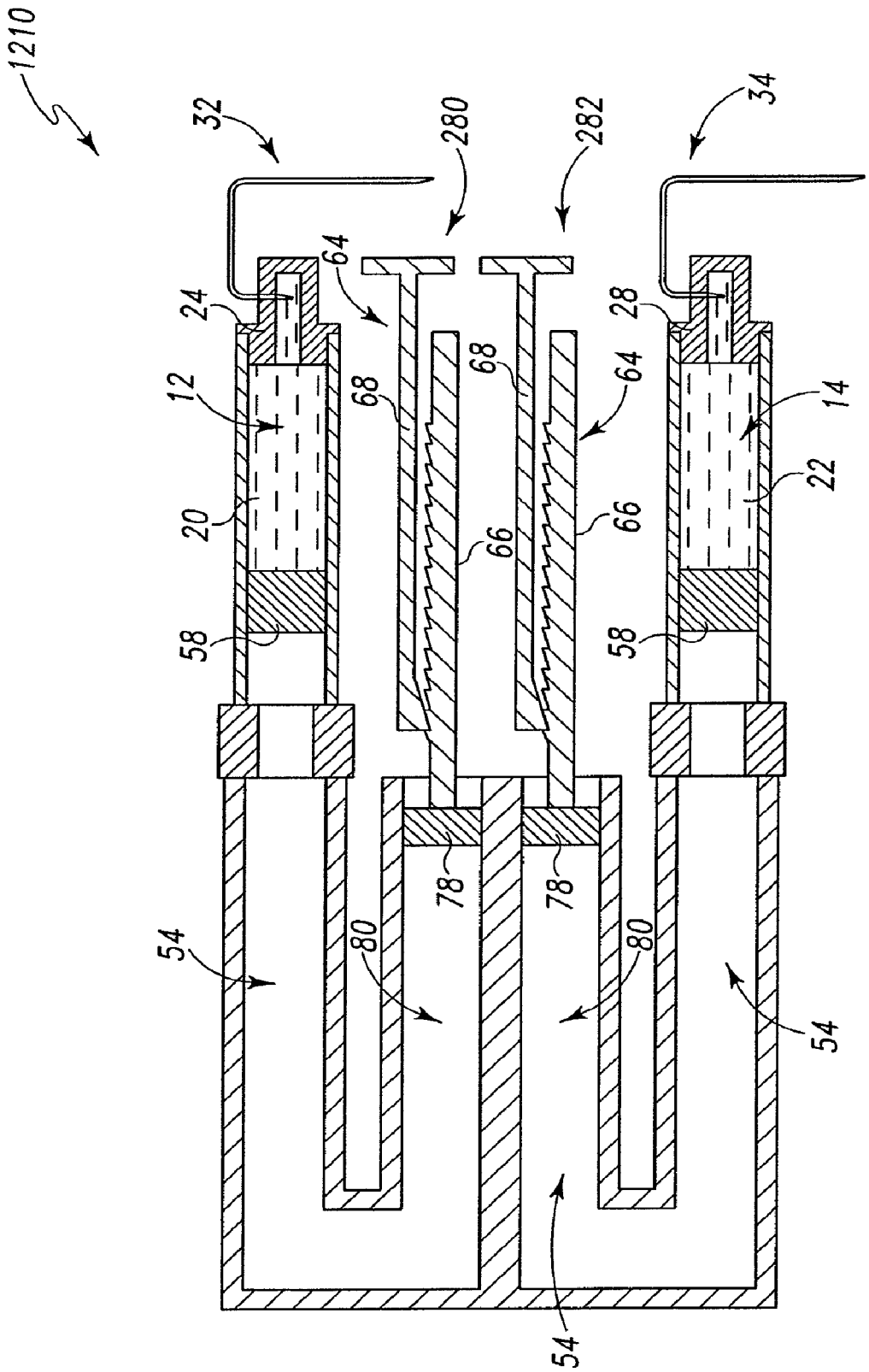

Looking now to FIGS. 12 and 13, fluid delivery devices 1110, 1210 of the present disclosure are provided. The devices 1110, 1210 are similar to the fluid delivery devices discussed above. As such, like reference numerals are used to denote like components. Each of the fluid delivery devices 1110, 1210 provides only a bolus delivery of both the first and second medicaments 20, 22 and does not provide a basal delivery of either of the first and second medicaments 20, 22. Therefore, looking first to FIG. 12, the fluid delivery device 1110 includes one bolus drive mechanism 62 associated with each of the respective first and second drug reservoirs 12, 14 to provide bolus delivery of each of the first and second medicaments 20, 22. No basal delivery function is provided for either of the first or second medicaments 20, 22. Looking now to FIG. 13, the fluid delivery device 1210 includes first and second bolus drive mechanisms 280, 282 associated with the respective first and second drug reservoirs 12, 14 to provide separate bolus delivery of each of the first and second medicaments 20, 22. Again, no basal delivery function is provided for either the first or second medicaments 20, 22. Of course, the dimension(s) of many of the components of the fluid delivery devices 1110, 1210 may be varied in order to provide a device wherein the bolus delivery of the first medicament 20 is different from the bolus delivery of the second medicaments 22. For example, the size or diameter of one or both of the bolus pistons 78 may be varied such as that shown in the fluid delivery device 450 of FIG. 5b.

Figure 14:
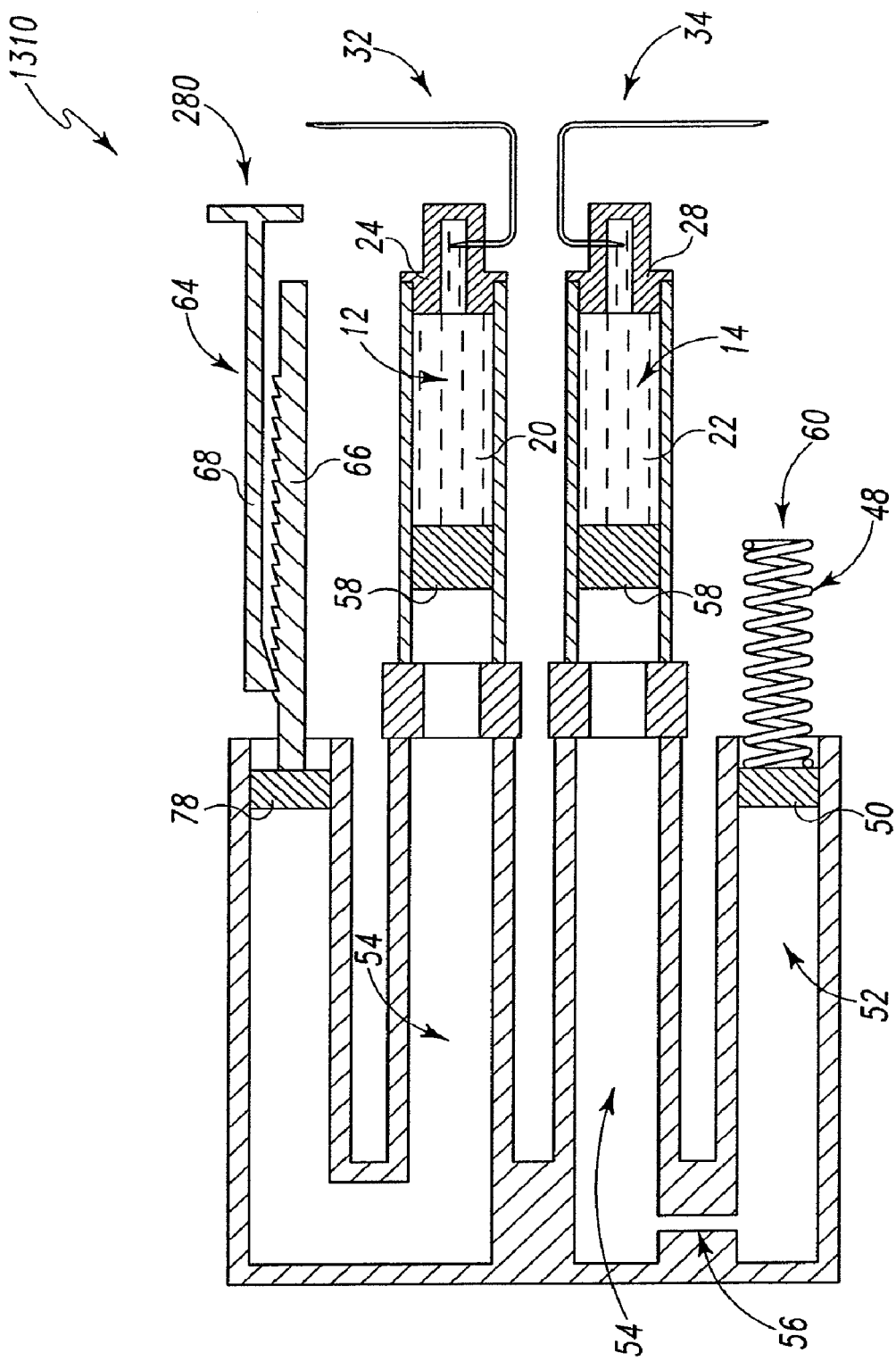
FIG. 14 is a schematic of another drug delivery device of the present disclosure which provides a bolus delivery of only the first medicament and a basal delivery of only the second medicament.

Looking now to FIG. 14, a fluid delivery device 1310 provides a basal delivery of the second medicament 22 and a bolus delivery of the first medicament 20. Illustratively, no basal delivery is provided for the first medicament 20 while no bolus delivery is provided for the second medicament 22. Such an arrangement may be beneficial where only basal delivery of a first medicament is desired while only supplemental bolus delivery of the second medicament desired. It is within the scope of this disclosure to provide a fluid delivery device capable of providing a basal delivery of only the first medicament 20 while providing a bolus delivery of only the second medicament 22, for example. Illustratively, the fluid delivery device 1310 shown in FIG. 14 includes the bolus drive mechanism 280 associated with the first fluid reservoir 12 and the basal drive mechanism 60 associated with the second fluid reservoir 14.

The fluid delivery devices 10, 110, 210, 310, 410, 510, 550, 610, 710, 810, 910, 1010, 1310, and 1410 described above each include one or more of the basal fluid reservoirs 52, 352 fluidly coupled to one or more pump chambers 54 by a flow restrictor, such as flow restrictors 56, 356, 357, 358, 856, 858. Illustratively, the fluid reservoirs 52, 352 each define an inner chamber wherein the respective basal drive piston 50 of the particular basal drive mechanism is positioned within the inner chamber. However, other various basal fluid reservoirs which in fluid communication with one or more pump chambers may be provided as well. For example, looking to FIGS. 15 and 16, fluid delivery devices 1410 and 1510 are provided which each include a flexible, balloon-type fluid delivery reservoir 1452 containing hydraulic fluid, such as oil, therein.

Figure 15:
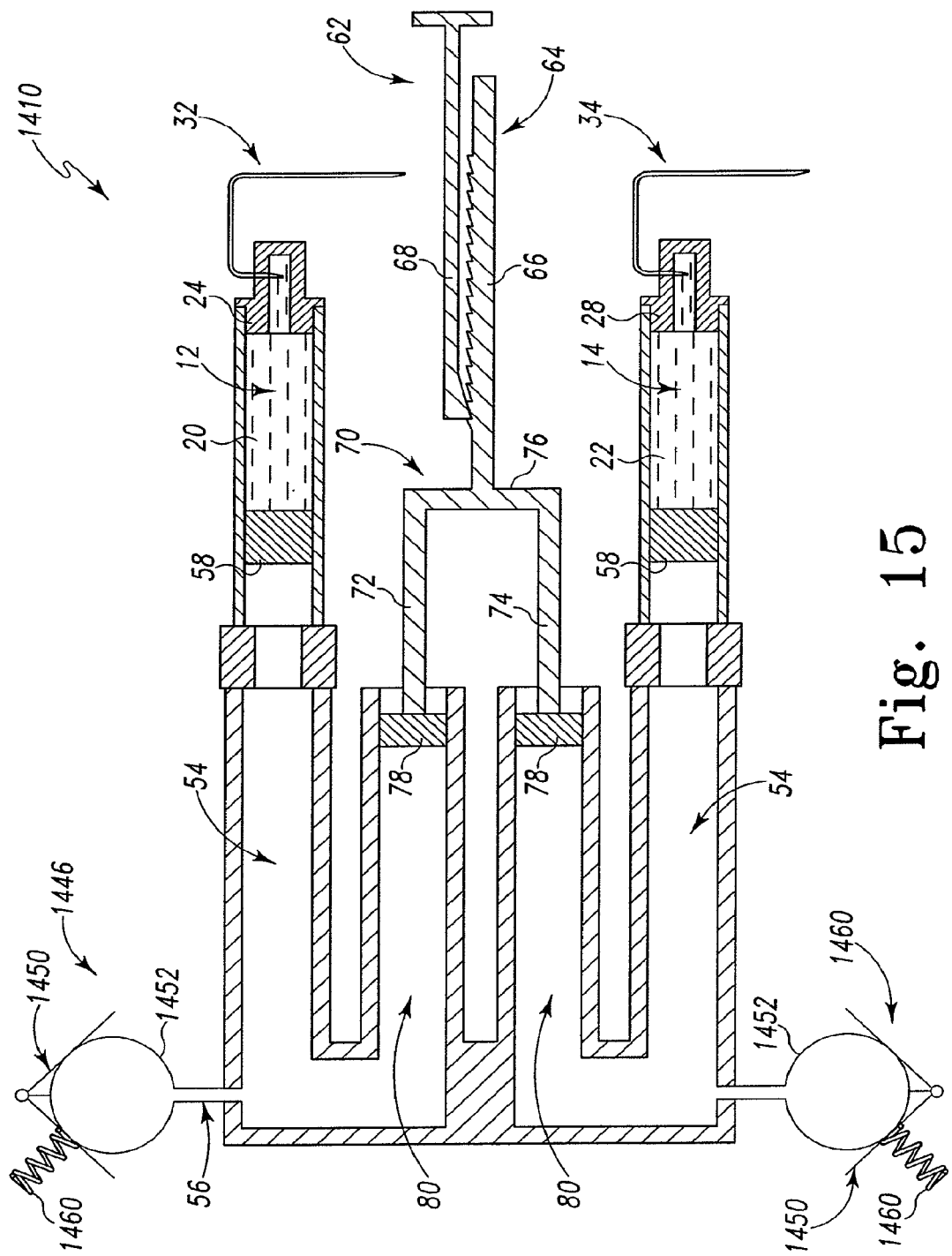
FIG. 15 is a schematic of another drug delivery device of the present disclosure which provides a balloon-like basal fluid reservoir associated with each of the first and second medicaments and an alternative basal drive mechanism coupled to the respective basal fluid reservoirs.

Looking specifically to FIG. 15, two separate fluid delivery reservoirs 1452 are provided which are each associated with one of the first and second fluid reservoirs 12, 14. Further an alternative basal drive mechanism 1446 is provided to force fluid from the respective basal fluid reservoir 1452 through the flow restrictor 56 and into the pump chamber 54. Illustratively, each basal drive mechanism 1446 includes a hinged plate member 1450 coupled to the respective flexible basal fluid reservoir 1452. The hinged plate member 1450 may be compressed by a spring 1460 or other external force in order to force hydraulic fluid from within the reservoir 1452 through the flow restrictor and into the pump chamber 54 to advance the drive piston 58 and provide a basal delivery of the first medicament 20, for example. While the hinged plate member 1450 and spring 1460 are disclosed, it is within the scope of this disclosure to provide other suitable drive mechanisms for compressing the flexible basal fluid reservoir 1452.

As shown in FIG. 15, the first and second basal drive mechanisms 1446, 1460 operate to compress the respective flexible basal fluid reservoir 1452 in order to provide a basal delivery of each of the first and second medicaments 20, 22. Alternatively, a single basal drive mechanism 1446 of the fluid delivery device 1510 shown in FIG. 16 operates to provide a basal delivery of both the first and second medicaments 20, 22.

Figure 16:
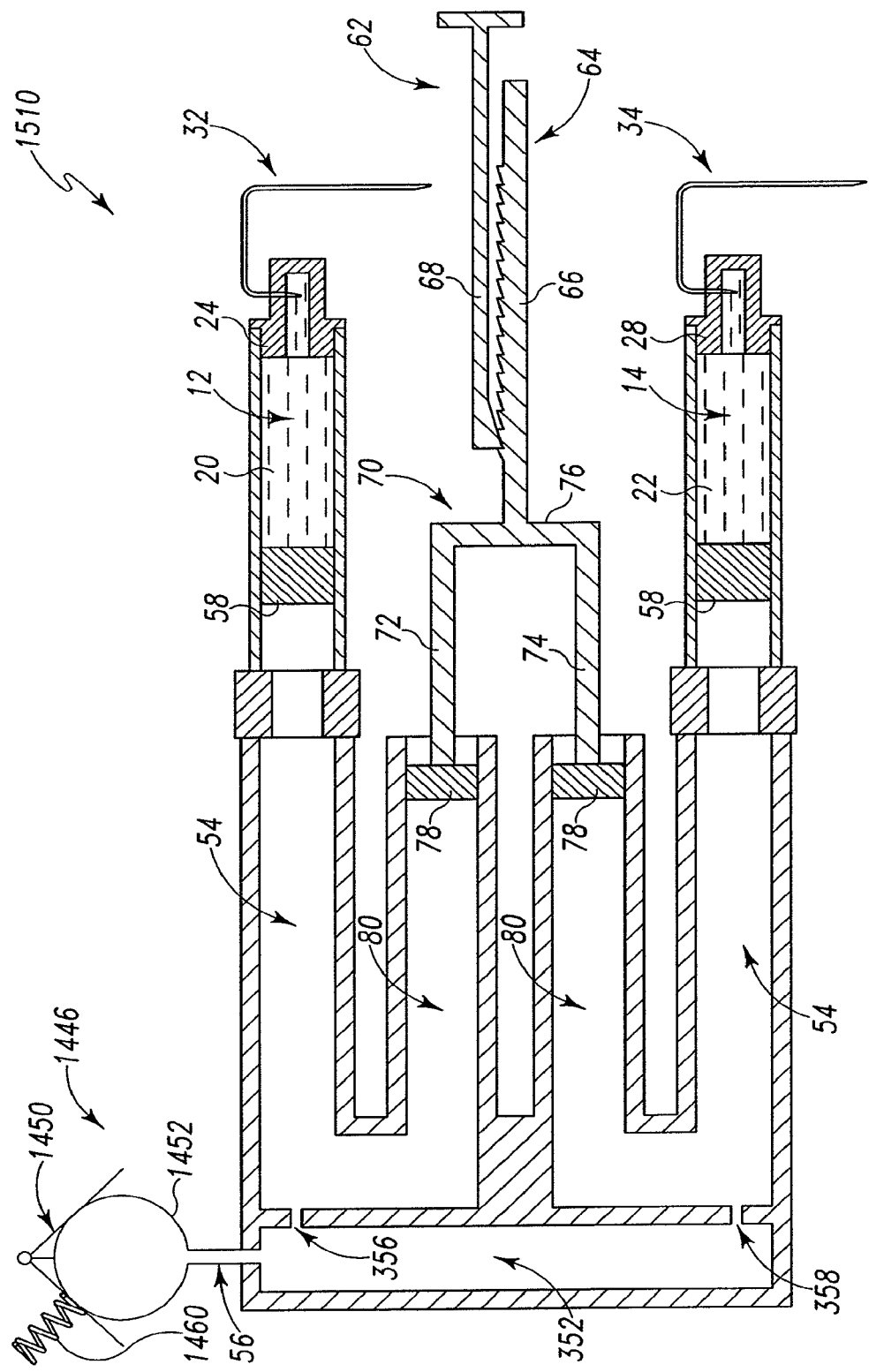
FIG. 16 is a schematic of another drug delivery device of the present disclosure similar to the device shown in FIG. 15 and providing a single alternative basal drive mechanism and balloon-like basal fluid reservoir for providing a basal delivery of each of the first and second medicaments.

Illustratively, any of the fluid delivery devices disclosed herein may include basal and/or bolus drive mechanisms including a hinged plate member and a compressible fluid reservoir such as that shown in FIGS. 15 and 16. It is also within the scope of this disclosure to include other suitable drive mechanisms for advancing a fluid through a flow restrictor. For example, a gas drive mechanism may generate gas, such as oxygen, for example, which exerts a force on either a piston, such as the basal and bolus drive pistons described herein, or which exerts a force on a flexible membrane to push a hydraulic liquid through a flow restrictor to then advance the medicament to be delivered. Alternatively, such a flexible membrane may directly force the medicament through a needle or other such infusion device. Further, a spring compressed bellows crank, a paired roller set, or other mechanism to force hydraulic fluid (from a fluid reservoir, for example) through a flow restrictor and into a pump chamber to thereby exert a pressure on a movable barrier within a drug delivery chamber to expel at least some fluid from within the drug delivery chamber through an aperture of the drug delivery chamber may be provided.

Figure 17:
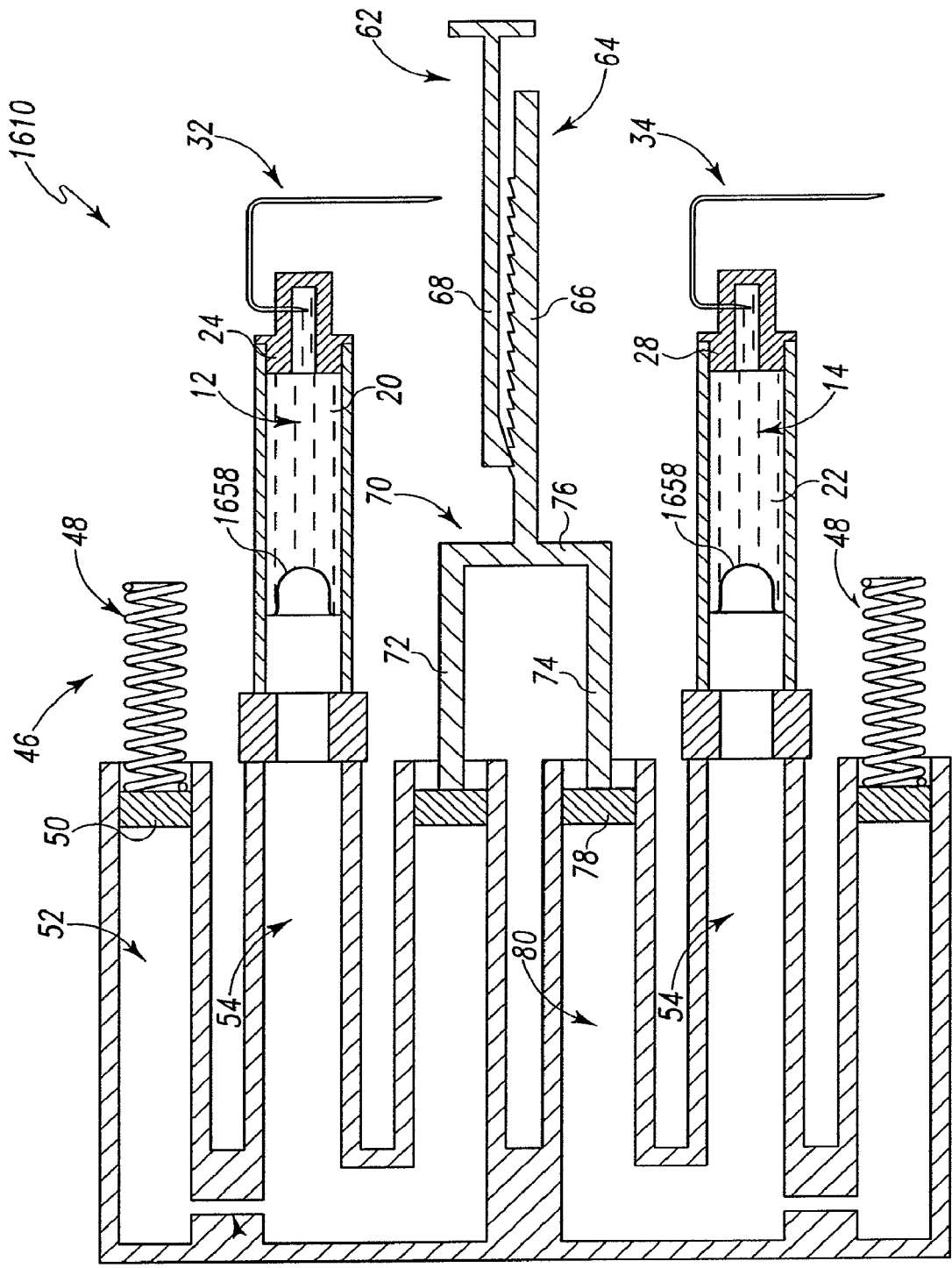
FIG. 17 is a schematic of another drug delivery device of the present disclosure similar to the device shown in FIG. 1 where a delivery piston associated with each of the first and second medicaments of FIG. 1 is substituted with a flexible member.

Looking now to FIG. 17, a fluid delivery device 1610 is provided. The fluid delivery device 1610 is similar to the fluid delivery devices described above. As such, like reference numerals are used to denote like components. A flexible member 1658 of the fluid delivery device 1610 has replaced the driven piston 58 of previous embodiments. The flexible member 1658 is able to deform in response to the pressure exerted upon it from hydraulic fluid forced into the pump chamber 54 from either the basal fluid reservoir 52 through the flow restrictor 56 or from the bolus fluid reservoir 80. The deformation of the flexible member 1658 into the drug reservoir 12 forces the first medicament 20 within the reservoir 12 through the needle 32.

Illustratively, the flexible member 1658 as well as the piston 58 described in previous embodiments operate as barrier mechanisms between the one of the medicaments 20, 22 and the hydraulic fluid exerting pressure onto the barrier mechanism. Although the piston 58 and the flexible member 1658 have been specifically disclosed herein, it is within the scope of this disclosure to include other such suitable barrier mechanisms separating the medicament 20, 22 from the hydraulic fluid. At least a portion of such barrier mechanisms are capable of moving within the inner chamber of the fluid reservoir relative to the outer walls of the fluid reservoir in order to force medicament out of the fluid reservoir. Various other barrier mechanisms are described in greater detail in U.S. Pat. No. 6,969,324 and U.S. Patent Application Publication No. US 2005/0119618, the disclosures of which are hereby incorporated by reference herein.

Each of the fluid delivery devices described above includes a first needle 32 in fluid communication with the reservoir 12 containing the first medicament 20 and a second needle 34 in fluid communication the reservoir 14 containing with the second medicament 22. These separate needles 32, 34 may be spaced-apart from each other a desired distance in order to prevent any mixing or comingling of the first and second medicaments 20, 22 once the medicaments are introduced subcutaneously into the patient. It is often desirable, for example, to prevent any mixing of two different medicaments before delivery, during delivery, and after delivery of the medicaments into the patient if and when there may be compatibility issues between the two medicaments, for example. As such, the needles 32, 34 may be positioned at opposite ends of the respective fluid delivery device in order to maximize the distance between the two medicaments when each is delivered into the patient.

Figure 18:
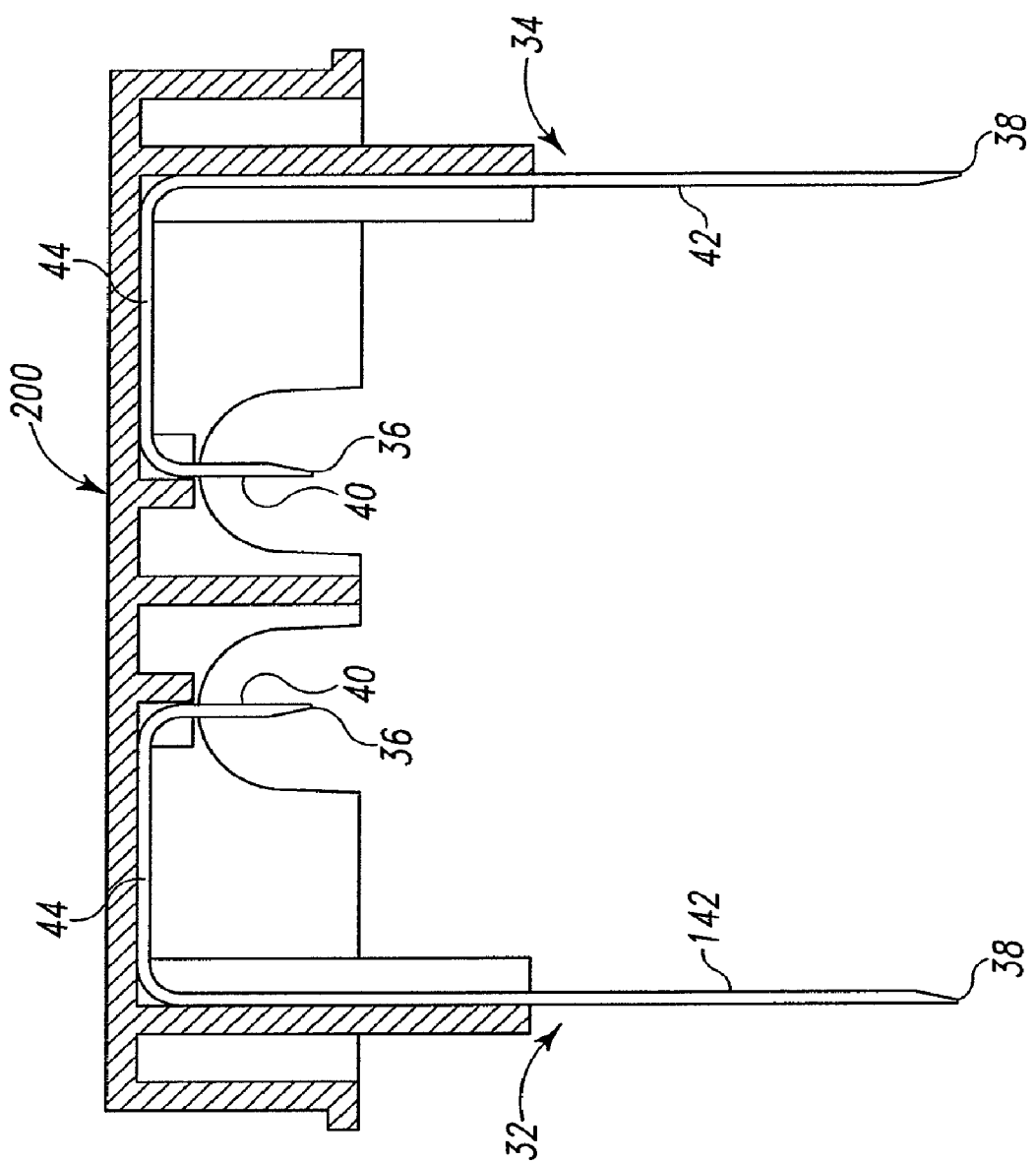
FIG. 18 is a schematic of a needle configuration of the present disclosure including first and second needles having delivery arms of different lengths to deliver the first and second medicaments at a different subcutaneous depth within the patient.

Additionally, or as an alternative, the first needle 32 may be provided with a delivery arm 142 which is significantly longer than the delivery arm 42 of the second needle 34, as shown in FIG. 18, for example. As such, the delivery arm 142 of the first needle 32 will be inserted to a greater subcutaneous depth within the patient than the delivery arm 42 of the second needle 34. In such an instance, the first medicament 20 is delivered to the patient at a different subcutaneous depth than the subcutaneous depth to which the second medicament 22 is delivered. By varying the depth to which the delivery end of the needles 32, 34 are inserted within a patient, the first and second medicaments 20, 22 may be substantially prevented from mixing once injected into the patient.

Illustratively, therefore, separate needles 32, 34 may be used to separately deliver the first and second medicaments 20, 22. In instances where there may be compatibility issues between the two medicaments 20, 22, the needles 32, 34 may be spaced-apart from each other a suitable distance to substantially prevent any mixing of the medicaments 20, 22 during and after delivery of the medicaments 20, 22 to the patient. Additionally, or as an alternative, the needles 32, 34 may be inserted into the patient at different depths to further prevent any mixing of the medicaments 20, 22 during or after delivery of the medicaments 20, 22.

Looking again to FIG. 18, a needle cover button 200 is provided which illustratively houses both needles 32, 34 therein. As such, actuation of the needle cover button 200 by a user or patient actuates both needles 32, 34 at the same time. Illustratively, in operation, the needles 32, 34 are positioned in a first, un-activated position (not shown) whereby the uptake arm 40 of each needle 32, 34 is spaced apart from the respective stoppers 24, 28. Further, the delivery arm 142, 42 of each needle 32, 34 is contained within an external housing (not shown) of the fluid delivery device. In order to move the needles to an activated position, a user depresses the button 200 to lower each needle 32, 34 such that the uptake arm 40 of each needle 32, 34 pierces the respective stopper 24, 28 and is in fluid communication with the hollow chamber 26 containing the respective first and second medicaments 20, 22, as shown in FIGS. 1-17, for example. Further, in the activated position the distal end 38 of the delivery arm 142, 42 of each needle 32, 34 extends beyond the external housing of the delivery device for subcutaneous placement within the patient. Although the single needle cover button 200 is shown in FIG. 18, it is within the scope of this disclosure to include a separate needle cover button associated with each needle 32, 34 such that the needles 32, 34 may be activated separately.

Figure 19:
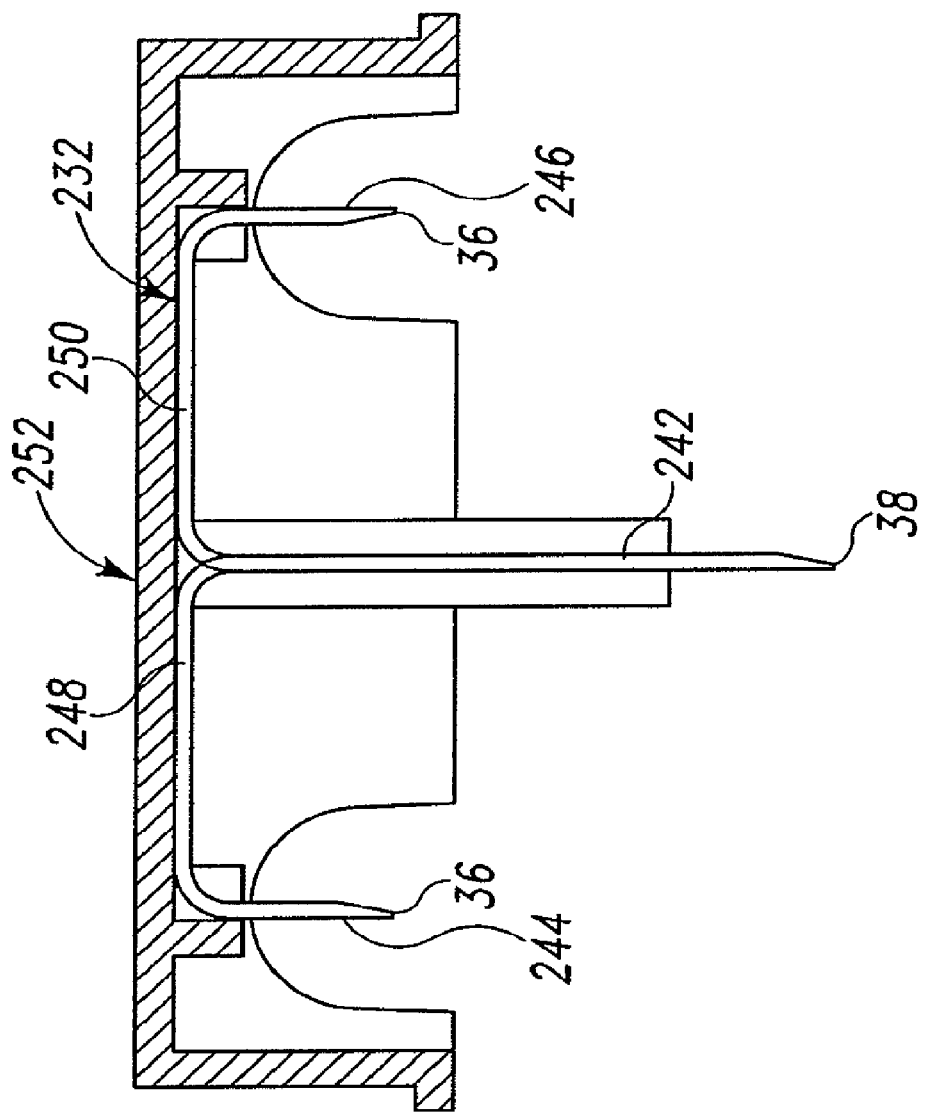
FIG. 19 is a schematic of a generally "Y-shaped" needle for fluid communication with the reservoir of each of the first and second medicaments.

Looking now to FIG. 19, a generally "Y-shaped" needle 232 is provided and may be used with one or more of the delivery devices disclosed herein. Illustratively, the needle 232 includes a single delivery arm 242, a first uptake arm 244 spaced-apart from and illustratively parallel to the delivery aim 242, and a second uptake arm 246 spaced-apart from and illustratively parallel to the delivery arm 242 as well. A respective first and second transverse or connector arm 248, 250 couples each of the uptake arms 244, 246 to the delivery arm 242. The needle 232 is cannulated to define a continuous passageway extending through each of the arms 242, 244, 246, 248, 250. In an activated position, the first end 36 of each uptake arm 244, 246 is received through an outer wall of the respective first and second stoppers 24, 28 of the various fluid delivery devices disclosed herein. As such, the first end 36 of each uptake arm 244, 246 is positioned within the hollow chamber 26 of each stopper 24, 28 when the needle 232 is in the activated position. The second end 38 of the delivery arm 242 of the needle 232 is provided for subcutaneous insertion into a patient in order to deliver the first and second medicaments 20, 22 to the patient.

Illustratively, the needle 232 permits the first and second medicaments 20, 22 to mix with each other prior to being delivered into the patient. For example, the first medicament 20 may enter the uptake arm 244 of the needle 232 and travel along the transverse arm 248 to the delivery arm 242. The second medicament 22 may similarly enter the uptake arm 246 of the needle 232 and travel along the transverse arm 250 to mix with the first medicament 20 in the delivery arm 242. The needle 232 may be used with delivery devices where the first and second medicaments 20, 22 contained within such delivery devices are compatible with each other and may be mixed prior to delivery into the patient. Of course, with separate basal and bolus delivery mechanisms, there may be instances where only the first medicament 20 or only the second medicament 22 is being delivered through the needle 232.

While the "Y-shaped" needle 232 is disclosed herein for use with compatible medicaments able to be mixed together, it should be understood that other suitable needles may be used which permit the medicaments to mix with each other after leaving the fluid reservoirs within which each is stored. For example, it is to be understood that Y-shapes are intended to encompass T-shapes. Further illustratively, a cover button 252 is shown in FIG. 19 to cover and maintain the needle 232 in the un-activated position until the button 252 is depressed or activated by a user or patient. Further, upon depressing the cover button 252, the needle 232 may be moved to the activated position to allow fluids from the first and second reservoirs 12, 14 to enter the respective uptake arms 244, 246.

According to one aspect of the present disclosure, a fluid delivery device may include a plurality of drug reservoirs for containing and delivering a plurality of different medicaments. For example, while the fluid delivery devices described above and shown in FIGS. 1-17, include first and second medicaments 20, 22 contained within first and second reservoirs 12, 14, it is within the scope of this disclosure to include a fluid delivery device having a third medicament contained within a third reservoir. A separate or shared basal drive mechanism may be associated with the third reservoir containing the third medicament while a separate or shared bolus drive mechanism may also be associated with the third reservoir containing the third medicament. Further, a shared or separate needle may also be associated with each of the first, second, and third medicaments to deliver each medicament separately or combined. Similarly, it is within the scope of this disclosure to include a fluid delivery device having more than three medicaments each contained within separate fluid reservoirs.

According to another aspect of the present disclosure, the delivery devices disclosed herein are relatively compact, portable, and able to be fixed to the user or patient during use and subsequently disposed of when the treatment is finished. Of course, other such non-portable and non-disposable delivery devices are included within the scope of this disclosure as well.

According to still another aspect of the present disclosure, the fluid delivery devices described herein are adapted to deliver two different medicaments 20 and 22. In one embodiment, the first and second medicaments 20, 22 are selected as being adapted for treating two different diseases that may occur in a co-morbid disease state. In another embodiment, the first and second medicaments 20, 22 are selected as being adapted for treating two different symptoms that may be present in a single disease. In another embodiment, the first and second medicaments 20, 22 are selected as being adapted for treating the same disease and/or symptom where such a combination of such two or more medicaments may be contemplated or desirable.

In another embodiment, the first and second medicaments 20, 22 are selected as being adapted for treating a disease state where for example, one of the first or second medicaments 20, 22 causes undesirable or unwanted side effects or other adverse events, and the other of the first and second medicaments 20, 22 mediates, ameliorates, or alleviates those side effects or adverse events.

In another embodiment, the first and second medicaments 20, 22 are selected as being adapted for treating a disease state where the efficacy or performance of one of the first or second medicaments 20, 22 is enhanced or improved by the co-administration of the other of the first or second medicaments 20, 22. Efficacy enhancement may be additive or synergistic, or may correct for or mediate sensitization, desensitization or tolerance that may accompany the use of one of the first or second medicaments 20, 22. It is appreciated that such enhancement or improvement may lead to the lowering of the overall amount of the medicament whose efficacy or performance is enhanced.

It is understood that the devices described herein may allow for the pairing of two medicaments that otherwise could not be delivered in a unitary dosage form by conventional means. For example, certain pairings of medicaments may not be possible in conventional unitary dosage forms due to chemical incompatibility, differential stability requirements, different formulation requirements, and other optimization parameters needed for efficacy. Further, certain pairings of medicaments may not be possible in conventional unitary dosage forms due to the need for flexibility in altering the ratio of the first and second medicaments. It is suggested that conventional dosage forms would require a fixed ratio. Further, certain pairings of medicaments may not be possible in conventional unitary dosage forms due to complicated dosing regimens requiring alternate administration over predetermined time periods. It is to be further understood that though the foregoing describes drug pairings, those aspects apply equally to embodiments of the delivery devices described herein that are configured to deliver three or more medicaments.

In one embodiment, the devices described herein are adapted for delivering medicaments to treat diabetes, including Type I and Type II diabetes, diabetic symptoms, and diabetic conditions.

In one embodiment, the first or second medicament 20, 22 is insulin or an insulin analog, and the other medicament 20, 22 is drug selected to improve the performance, or decrease the side effect profile of the insulin or insulin analog. It is to be understood that the first and second medicaments 20, 22 may each refer to the insulin or analog thereof. For example, as used herein, insulin analogs include pro-insulin, pre-insulin, and insulins that have been modified with various amino acids, such as with insertions, deletions, and substitutions. The devices described herein include various options as to the presence or absence of bolus and/or basal delivery, the relative size of the bolus delivery, the relative rate of the basal delivery, and other features. Accordingly, in some embodiments of the devices, the insulin or insulin analog is the first medicament 20, while in other embodiments, the insulin or insulin analog is the second medicament 22. Accordingly, as used throughout the terms first medicament 20 and second medicament 22 may be interchanged with the identification of the medicament for different configurations and embodiments of the devices described herein.

In another embodiment, both natural and synthetic insulins and insulin analogs may be used as the first or second medicament 20, 22. In one aspect, insulins used are naturally occurring, such as naturally occurring human insulins and analogs thereof, including but not limited to those produced using recombinant methods from other organisms such as bacteria. In another aspect, insulins used are synthetic insulins, or modified insulins including amino acid chain modifications such as insertions, deletions, and exchanges in the insulin sequence. Illustratively, the insulins are Lispro insulin, Aspart insulin, Glargine insulin, Detemir insulin, and the like. Further, insulins include but are not limited to the amino acid insertions, amino acid deletions, and amino acid substitutions of various insulins from human and other sources. It is understood that such modifications may be made on the A or B chains. Illustratively, insulins may be included as medicaments 20, 22 herein, where Asp28 on the B-chain is substituted, such as with Pro28 or Lys28; where Lys29 in the B-chain is substituted with Pro29 or Glu29; where the B-chain is extended, such as with Arg31 or Arg31-Arg32; where Asn 21 on the A-chain is substituted, such as with Gly21; where Asn3 on the B-chain is substituted, such as with Lys3; and similar modifications.

In another aspect, insulins used as medicaments herein are intermediate acting insulins, including but not limited to HUMULIN L, HUMULIN N, NOVOLIN N, NOVOLIN R, and the like. In another aspect, insulins used as medicaments herein are rapid acting insulins, including but not limited to APIDRA, HUMALOG HUMULIN R, NOVOLIN R, NOVOLOG, and the like. In another aspect, insulins used as medicaments herein are long acting insulins, including but not limited to HUMULIN U, LANTUS, and the like. In another aspect, insulins used as medicaments herein are mixtures of various insulins, including but not limited to HUMALOG MIX 75/25, HUMULIN 50/50, HUMULIN 70/30, NOVOLIN 70/30, NOVOLOG MIX 70/30, and the like.

In one variation, both medicaments 20, 22 are insulins. It is appreciated that more varied mixtures of insulins may be delivered to certain patients using configurations where the first medicament 20 is one insulin, and the second medicament 22 is another insulin. It is understood that insulins may be selected to suit the needs of various subpopulations of patients for which readily available premixed insulins are less desirable, or where mixing insulins is not desirable. In another aspect the first insulin is long acting insulins such as HUMULIN U, LANTUS, and the like, and the second insulin is an intermediate or short acting insulin, as described herein. In one configuration, the device is selected such that both the first and second medicaments 20, 22 are primarily or exclusively administered to the patient in a bolus manner rather than a basal manner. In those configuration, it is understood that for example, the long acting insulin may be administered as a once-per-day bolus amount, and the short or intermediate acting insulin is administered in a meal-time ready bolus amount. In one variation it is contemplated that the short or intermediate acting insulin may be administered in a basal manner as well, or in another variation the short or intermediate acting insulin may be administered in a basal manner over a shortened period of time to correspond with meal time.

In an alternate embodiment, the other medicament 20, 22 may be included to increase the efficacy of, improve the performance of, or decrease the side effect profile of the insulin or insulin analog used as a medicament. The mechanisms for this increased insulin efficacy or improved performance may be any, including improving endogenous insulin production, decreasing insulin resistance or insulin insensitivity, improving the utilization of insulin and glucose by peripheral tissues, increasing the uptake of glucose by peripheral tissues, decreasing the amount or slowing the rate of endogenous sugar production from certain organs, including but not limited to the liver, decreasing the amount or slowing the rate of gastrointestinal sugar absorption, and the like.

In one configuration, the other medicament is an incretin, incretin mimetic or incretin analog, such as glucagon-like-peptide (GLP), a GLP-1 analog, exenatide (BYETTA, Amylin, Lilly), Extendin-4, and the like. Incretin mimetics and/or incretin analogs may act analogous to Glucagon-Like Peptide-1 (GLP-1), a naturally occurring peptide which enhances insulin secretion in response to elevated plasma glucose levels, may be included as helper drugs. It is understood that the GLP-1 system increases insulin secretion only in the presence of elevated plasma glucose levels, avoiding inappropriately high insulin levels during fasting. It is appreciated that incretins may enhance glucose-dependent insulin secretion and exhibit other antihyperglycemic actions following their release into the circulation. Incretins may also moderate peak serum glucagon levels during hyperglycemic periods following meals, without interfering with glucagon release in response to hypoglycemia. Incretins may also have beneficial secondary effects of reducing the rate of gastric emptying and decrease food intake, mitigating the potential severity of hyperglycemic events after meals. In one embodiment, the devices described herein include a daily dose of BYETTA in the range from about 5 to about 10 micrograms. In the foregoing configuration, it is appreciated that devices may be selected that include a separate needle for each of the reservoirs containing medicaments 20, 22, such that substantial mixing of the two medicaments does not occur at, or optionally near, the sites of injection.

In another configuration, the other medicament is an amylin peptide, such as pramlintide (SIMLYN, Amylin). It is appreciated that deficiencies in insulin may parallel deficiencies in amylin. Amylin may have a moderating effect on blood glucose absorption from the gut into the blood, slowing and managing meal-derived glucose inflow, controlling pancreatic glucagon secretion, and consequently regulating hepatic glucose production. In the foregoing configuration, it is appreciated that devices may be selected that include a separate needle for each of the reservoirs containing medicaments 20, 22, such that substantial mixing of the two medicaments does not occur at, or optionally near, the sites of injection.

In another configuration, the other medicament is a biguanide or biguanide combination In one illustrative aspect, the biguanide is metformin (GLUCOPHAGE, FORTAMET, RIOMET). In another illustrative aspect, the biguanide is an inhibitor of hepatic glucose production. In another aspect, the biguanide is an inhibitor of gastrointestinal glucose absorption. It is appreciated that biguanides may increase the efficacy of insulin therapy by decreasing hepatic glucose production, decreasing intestinal absorption of glucose, and/or increasing peripheral glucose uptake and utilization. In one variation, pharmaceutically acceptable salts of such medicaments are included in the devices described herein.

In another configuration, the other medicament is a glucosidase inhibitor, such as acarbose (PRECOSE, Bayer), and the like. It is appreciated that glucosidase inhibitors may increase the efficacy of insulin therapy by slowing either the pancreatic and/or intestinal hydrolysis of complex carbohydrates to glucose.

In another configuration, the other medicament is a sulfonylurea, such as Amaryl glimepiride (AMARYL, Aventis), glyburide (DIABETA, Aventis), glipizide (GLUCOTROL, Pfizer), and like insulin secretagogues. It is appreciated that sulfonylureas may increase the efficacy of insulin therapy by increasing the amount of endogenous insulin secretion, such as from pancreatic beta cells. In addition, sulfonylureas may increase the efficacy of insulin therapy by increasing the sensitivity of peripheral tissues to insulin.

In another configuration, the other medicament is a meglitinide, such as repaglinide (PRANDIN, Novo Nordisk), nateglidine (STARLIX, Novatis), and like insulin secretagogues. It is appreciated that meglitinides may increase the efficacy of insulin therapy by increasing the amount of endogenous insulin secretion, such as from pancreatic beta cells, by blocking ATP-dependent potassium channels.

In another configuration, the other medicament is an agonist of a peroxisome proliferator activated receptor (PPAR) such as PPARγ. In one embodiment, the PPARγ agonist is a thiazolidinedione (TZD) insulin sensitizer, including but not limited to pioglitazone (ACTOS, Takeda), AVANDAMET (GlaxoSmithKline), rosiglitazone maleate (AVANDIA, GlaxoSmithKline), phenformin, buformin, and the like. It is appreciated that TZD insulin sensitizers and other PPARγ agonists may increase the efficacy of insulin therapy by decreasing insulin resistance or insensitivity in peripheral tissues and in the liver, resulting in increased insulin dependent glucose disposal and decreased hepatic glucose output. It is appreciated that compounds that also lack PPARα binding action may be advantageously included in the devices described herein.

In another configuration, mixtures of such other medicaments are contemplated. Illustratively, the mixture may be of a TZD insulin sensitizer or PPARγ agonist and a biguanide, such as metformin mixed with rosiglitazone maleate (AVANDAMET, GlaxoSmithKline), and like mixtures. It is appreciated that other drugs that reduce hepatic gluconeogenesis may be included alone or in combination with TZDs. It is also appreciated that other drugs that decrease intestinal absorption of glucose may be included alone or in combination with TZDs. It is also appreciated that other drugs that improves insulin sensitivity by increasing peripheral glucose uptake and utilization may be included alone or in combination with TZDs. In addition, the mixture may be of an incretin mimetic or incretin analog and a biguanide or sulfonyl urea, such as exenatide mixed with metformin or glimepiride, and like mixtures. In addition, the mixture may be of a biguanide and a sulfonylurea, such as metformin mixed with glipizide (METAGLIP, Bristol Meyers Squibb), and like mixtures.

In another configuration, the other medicament is a saccharide, such as a glucagon or an analog thereof. It is appreciated that during insulin administration with the devices described herein, it may be desirable or necessary to moderate and/or lessen the impact of insulin administration that may result in hypoglycemia or a hypoglycemic condition. It is further appreciated that the administration of such a saccharide may be controlled by the basal functions of the devices described herein, or alternatively by the bolus functions of the devices described herein. For example, in one illustrative embodiment, upon the onset of hypoglycemia or a hypoglycemic condition, the patient being treated may initiate a bolus administration of the saccharide. It is understood that the onset of hypoglycemia or a hypoglycemic condition may be determined using any conventional method of monitoring blood-glucose levels, including but not limited to blood-glucose strips, and the like. In one variation, the onset of hypoglycemia or a hypoglycemic condition may be determined by the patient through training, and/or experience in recognizing certain symptoms indicating such hypoglycemia or a hypoglycemic condition. It is further understood that in other configurations, it is less desirable to have any sustained levels of glucagon administration, and therefore one variation of this embodiment would include bolus delivery of the saccharide as the primary or exclusive route of administration.

In another configuration, the other medicament is insulin-like growth factor (IGF) 1 or 2, or an analog or derivative thereof. It is appreciated that IGF-1 and/or IGF-2 may be administered with insulin, or analogs thereof, to decrease hypoglycemia and/or hypoglycemic conditions that may be caused by insulin administration alone. IGF-1 and IGF-2 bind to insulin receptors, but with much lower affinity than does insulin, such as at about 10-fold or even 100-fold less affinity than insulin. Without being bound by theory, it is suggested co-administration of IGF-1 or IGF-2, or an analog or derivative thereof, may decrease insulin sensitivity and therefore may decrease the potential for the onset of hypoglycemia and/or hypoglycemic conditions caused by insulin administration. It is understood that IGF-1 and IGF-2 may be rapidly bound to binding proteins upon administration. Accordingly, ligand conjugates of IGF-1 and IGF-2, and their analogs, are also contemplated herein. Such ligand conjugates may increase the overall bioavailability of the IGF-1 and IGF-2, or analog thereof that is administered as described herein.

In another configuration, the other medicament is C-peptide, or an analog thereof. It is understood that in endogenous insulin production and metabolism, pro-insulin is made in the β-cells and once release it is cleaved by peptidases to release the C-peptide fragment. Finally, carboxypeptidase E produces the mature insulin by truncating the terminus of the B-chain. It is appreciated that C-peptide may be co-administered with the insulin, or any analog or derivative thereof, as the second medicament. Without being bound be theory, it is suggested that C-peptide is useful in regulation of glucose metabolism and also in other biologically important processes, and therefore, the complete or near complete replacement of endogenous insulin with exogenous sources may lead to an undesirable level of C-peptide. For example, neuropathy is a co-morbid pathology that may accompany diabetes or other diabetic conditions or condition of glucose dysregulation. Thus, it is suggested that C-peptide administration may treat neuropathy, decrease the progression of neuropathy, or delay or halt the onset of neuropathy. It is appreciated that the devices described herein may lead to better patient compliance than conventional methods, including conventional methods that include administering C-peptide by injection.

In one aspect, the C-peptide, or analog or derivative thereof, is administered to the patient at a ratio of about 1:1 on a molar basis compared to the insulin, thus mirroring the endogenous condition in healthy patients. In another aspect, the C-peptide, or analog or derivative thereof, is administered to the patient at a ratio of less than 1:1 on a molar basis compared to the insulin. In this latter embodiment, it is understood that levels of C-peptide may not need to be maintained as high as those of insulin to treat diabetes and associated conditions.

In addition, it is understood that C-peptide administration may lead to a plateau effect, and accordingly, patient needs for C-peptide may decrease over time. Thus, in this alternate aspect, the C-peptide, or analog or derivative thereof, is administered to the patient at a ratio of about 4:5, about 3:4, about 2:3, or about 1:2 on a molar basis compared to the insulin.

In addition, it is appreciated that though the foregoing embodiment where the second medicament is C-peptide, or an analog or derivative thereof, may be administered using any of the devices described herein, in one variation, devices are selected that include a single needle, whereby both medicaments 20, 22 mix prior to administration. In another variation, devices are selected that include two or more needles, where at least two of such needles are located proximally to the other, thus allowing both medicaments 20, 22 to mix immediately or soon after administration at the site of entry into the patient.

In another configuration, the first and second medicaments 20, 22 are both anti-infective compounds. In one aspect, the anti-infective compounds are antibacterial agents, such as penicillins and related compounds, including carbacephems, carbapenems, cephalosporins, and the like, monobactams, polypeptides, aminoglycosides, glycopeptides, vancomycins, macrolide antibiotics including erythromycins, quinolones, sulfonamides, tetracyclines, and the like.

Illustrative aminoglycosides that may be included in the devices described herein include, but at not limited to, amikacin, gentamicin, kanamycin, neomycin, netilmicin, streptomycin, tobramycin, and the like. Illustrative carbacephems include loracarbef and the like. Illustrative carbapenems include ertapenem, imipenem, cilastatin, meropenem, and the like. Illustrative cephalosporins include first, second, third, and fourth generation cephalosporins, such as cefadroxil, cefazolin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and the like.

Illustrative macrolides that may be included in the devices described herein include, but at not limited to, azithromycin, clarithromycin, dirithromycin, erythromycin, roxithromyucin, troleandomycin, and the like. Illustrative glycopeptides that may be included in the devices described herein include teicoplanin, vancomycin, and the like. Illustrative penicillins include amoxicillin, ampicillin, azlocillin, cabenicillin, cloxacillin, and the like, and monobactams include aztreonam, and the like. Illustrative polypeptides include bacitracin, colistin, polymyxin B, and the like.

Illustrative quinolones includes ciprofloxacin, enoxacin, gatifloxacin, levofloxacin moxifloxacin, and the like. Illustrative sulfonamides include mafenide, sulfacetamide, sulfamethizole, sulfasalazine, sulfisoxazole, trimethoprim, BACT- RIM, and the like. Illustrative tetracyclines include demeclocycline, doxycycline, minocycline, oxytetracycline, tetracycline, and the like. Still other illustrative antibiotics that may be included in the devices described herein include, but at not limited to, arsphenamine, chloramphenicol, floramphenicol, clindamycin, ethambutol, fosfomycin, furzolidone, isoniazid, linezolid, metronidazole, nitrofurantoin, rifampin, spectinomycin, telithromycin, and the like.

In another embodiment, the first and second medicaments 20, 22 are agonists or antagonists of neurotransmitter receptors. In one illustrative aspect, the first medicament is dopamine or a dopamine receptor agonist, and the second medicament is a dopamine receptor antagonist. Illustrative dopamine receptor agonists and antagonists are described in PCT international application serial No. PCT/US2004/043145, the disclosure of which is incorporated herein in its entirety by reference. In one aspect, the dopamine agonist is selective for the dopamine $D_1$ receptor. In another aspect, the dopamine antagonist is selective for the dopamine $D_2$ receptor. It is appreciated that the co-administration of a dopamine $D_2$ receptor antagonist may enhance or improve the efficacy or overall benefit of the dopamine receptor agonist, including dopamine $D_1$ receptor agonists. It is also appreciated that the co-administration of a dopamine $D_2$ receptor antagonist may decrease, ameliorate, or alleviate side effects associated with the dopamine receptor agonist, including dopamine $D_1$ receptor agonists.

Illustrative dopamine $D_2$ receptor antagonists that may be included in the devices described herein include, but at not limited to, compounds of the formulae:

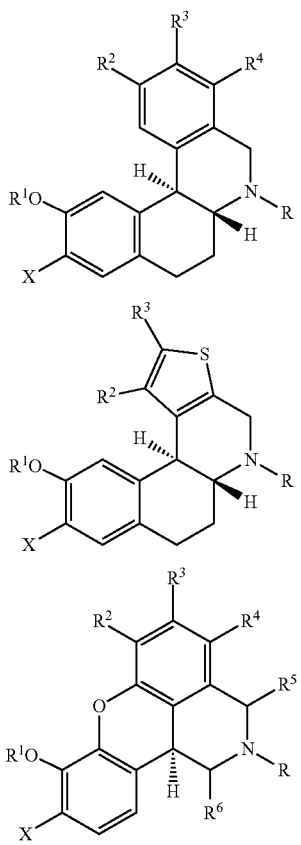

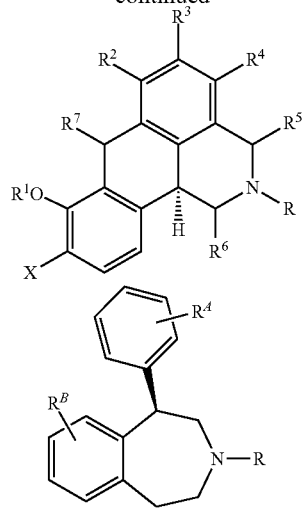

and pharmaceutically acceptable salts thereof, wherein R is hydrogen or $C_1$-$C_4$ alkyl; $R^1$ is hydrogen, acyl, such as $C_1$-$C_4$ alkanoyl, benzoyl, pivaloyl, and the like, or an optionally substituted phenyl or phenoxy protecting group, such as a prodrug and the like; X is hydrogen, fluoro, chloro, bromo, iodo or a group of the formula —$OR^8$ wherein $R^8$ is hydrogen, $C_1$-$C_4$ alkyl, acyl, such as $C_1$-$C_4$ alkanoyl, benzoyl, pivaloyl, and the like, or an optionally substituted phenyl or phenoxy protecting group, provided that when X is a group of the formula —$OR^8$, the groups $R^1$ and $R^8$ can optionally be taken together to form a —$CH_2$— or —$(CH_2)_2$— group, thus representing a methylenedioxy or ethylenedioxy functional group; $R^A$, $R^2$, $R^3$, $R^4$, $R^5$, $R^6$, and $R^7$ are each independently selected from hydrogen, $C_1$-$C_4$ alkyl, phenyl, fluoro, chloro, bromo, iodo, and a group —$OR^9$ wherein $R^9$ is hydrogen, acyl, such as $C_1$-$C_4$ alkanoyl, benzoyl, pivaloyl, and the like, or an optionally substituted phenyl or phenoxy protecting group; and $R^B$ is selected from hydrogen, $C_1$-$C_4$ alkyl, phenyl, fluoro, chloro, bromo, iodo, a group —$OR^9$ wherein $R^9$ is hydrogen, acyl, such as $C_1$-$C_4$ alkanoyl, benzoyl, pivaloyl, and the like, —$OR^1$ and X, as defined above, and optionally substituted phenyl or phenoxy protecting groups, providing that at least one of $R^B$ is —$OR^1$.

Illustrative dopamine $D_2$ receptor antagonists that may be included in the devices described herein include, but at not limited to, antipsychotic agents, illustratively selected from the typical and atypical families of antipsychotic agents. It is appreciated that atypical antipsychotics may generally be associated with less acute extrapyramidal symptoms, especially dystonias, and less frequent and smaller increases in serum prolactin concentrations associated with therapy. In one aspect, the typical antipsychotic agents include phenothiazines and non-phenothiazines such as loxapine, molindone, and the like. In another aspect, the atypical antipsychotic agents include the clozapine-like agents, and others, including aripiprazole, risperidone (3-[2-[4-(6-fluoro-1,2-benzisoxazol-3-yl)piperidino]ethyl]-2-methyl-6,7,8,9-tetrahydro-4H-pyrido-[1,2-a]pyrimidin-4-one), amisulpiride, sertindole (1-[2-[4-[5-chloro-1-(4-fluorophenyl)-1H-indol-3-yl]-1-piperidinyl]ethyl]imidazolidin-2-one), and the like. Phenothiazines include, but are not limited to chlorpromazine, fluphenazine, mesoridazine, perphenazine, prochlorperazine, thioridazine, and trifluoperazine. Non-phenothiazines include, but are not limited to haloperidol, pimozide, and thiothixene. Other clozapine-like agents include, but are not limited to olanzapine (2-methyl-4-(4-methyl-1-piperazinyl)-10H-thieno[2,3-b][1,5]benzodiazepine), clozapine (8-chloro-11-(4-methyl-1-piperazinyl)-5H-dibenzo[b,e][1,4]diazepine), quetiapine (5-[2-(4-dibenzo[b,f][1,4]thiazepin-11-yl-1-piperazinyl)ethoxy]ethanol), ziprasidone (5-[2-[4-(1,2-benzoisothiazol-3-yl)-1-piperazinyl]ethyl]-6-chloro-1,3-dihydro-2H-indol-2-one), and the like. It is appreciated that other typical and atypical antipsychotic agents may be used as the dopamine receptor antagonist described herein. It is also appreciated that various combinations of typical and atypical antipsychotic agents may be used.

The devices described herein may be configured to deliver daily dosage amounts of the various first and second medicaments 20, 22 at bioequivalency levels comparable to conventional drug formulations. Illustratively, metformin may be delivered at rates that correlate to the conventional oral dosage of 500, 850, 1,000, or 2,000 mg/day. It is to be understood that the amount delivered by the parenteral routes described herein for the various devices will often be substantially lower than the equivalent oral dosage form. For example, metformin may be delivered in a pulsatile or bolus delivery profile at a rate that corresponds to values that do not exceed the peak plasma concentration ($C_{max}$) observed for the oral dosage form, such as in the range from about 0.5 to about 4 µg/mL. Alternatively, metformin may be delivered in a sustained or basal delivery profile at a rates lower than the $C_{max}$, and corresponding to the average value under the area under curve (AUC), such as in the range from about 4 to about 10 µg·h/mL. These and other values for metformin, as well as for other first and second medicaments 20, 22 described herein are found in and/or routinely derived from values presented for the conventional dosage forms of such medicaments in Physicians' Desk Reference, Thompson PDR, Montvale N.J. (59$^{th}$ edition, 2005), the disclosure of which is incorporated herein by reference.

It is suggested that the devices described herein may be particularly appropriate for basal delivery, or alternatively bolus delivery at more frequent and lower doses, of medicaments that are delivered conventionally once or twice per day due to formulation issues, convenience, or poor expected patient compliance. Accordingly, the devices described herein may be configured to deliver pharmacokinetic (PK) profiles of medicaments that are not possible with conventional formulations. For example, the peak-valley PK profile generally accompanying once a day dosing may be converted to a lower level sustained release PK profile, or a lower peak-higher valley more frequent pulsatile PK profile.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A method of administering first and second medicaments from a fluid delivery device, the method comprising:
    forcing hydraulic fluid from a hydraulic fluid reservoir into a first pump chamber, the hydraulic fluid in the first pump chamber exerting a force on a first piston to expel at least a portion of the first medicament through an aperture of a first fluid reservoir and deliver a first basal delivery of the first medicament;
    forcing hydraulic fluid from the hydraulic fluid reservoir into a second pump chamber, the hydraulic fluid in the second pump chamber exerting a force on a second piston to expel at least a portion of the second medicament through an aperture of a second fluid reservoir and deliver a second basal delivery of the second medicament.

2. The method of claim 1, wherein forcing hydraulic fluid from the hydraulic fluid reservoir includes applying a spring force to a piston within the hydraulic fluid reservoir.

3. The method of claim 1, wherein forcing the hydraulic fluid from the hydraulic fluid reservoir includes forcing hydraulic fluid from the hydraulic fluid reservoir through a flow restrictor and into the first and second pump chambers.

4. A method of administering first and second medicaments from a fluid delivery device, the method comprising:
    delivering a first basal delivery of the first medicament, and delivering a second basal delivery of the second medicament,
    wherein the fluid delivery device comprises:
        a housing;
        a first reservoir within the housing and configured to contain the first medicament;
        a second reservoir within the housing and configured to contain the second medicament;
        a first basal drive mechanism within the housing and having a first hydraulic fluid reservoir;
        a first pump chamber in fluid communication with the first hydraulic fluid reservoir of the first basal drive mechanism via a first flow restrictor, the first pump chamber configured to engage the first reservoir to provide a basal delivery of the first medicament during use;
        a second basal drive mechanism within the housing and having a second hydraulic fluid reservoir;
        a second pump chamber in fluid communication with the second hydraulic fluid reservoir of the second basal drive mechanism via a second flow restrictor, the second pump chamber configured to engage the second reservoir to provide a basal delivery of the second medicament during use; and
    a needle having a first end configured for fluid communication with the first reservoir and a second end configured to extend exteriorly from the housing.

5. The method of claim 4, wherein the fluid delivery device further comprises a bolus drive mechanism coupled to the first pump chamber and configured to provide a bolus delivery of the first medicament.

6. The method of claim 5, wherein the bolus drive mechanism is coupled to the second pump chamber and is configured to provide a bolus delivery of the second medicament.

7. The method of claim 5, wherein the bolus drive mechanism is a first bolus drive mechanism and wherein the fluid delivery device further comprises a second bolus drive mechanism coupled to the second pump chamber and configured to provide a bolus delivery of the second medicament.

8. The method of claim 5, wherein the bolus drive mechanism includes a ratchet and a bolus piston coupled to the ratchet.

9. The method of claim 8, wherein the bolus of the first medicament is larger than the bolus of the second medicament.

10. The method of claim 4, wherein the first and second basal drive mechanisms each include a coil spring coupled to a drive piston.

11. The method of claim 4, wherein the fluid delivery device further comprises a first delivery piston coupled to the first pump chamber and positioned within the first fluid reservoir to exert a force on the first medicament within the first fluid reservoir and a second delivery piston coupled to the second pump chamber and positioned within the second fluid reservoir to exert a force on the second medicament within the second fluid reservoir.

12. The method of claim 4, wherein the fluid delivery device is an ambulatory infusion pump.

13. The method of claim 4, wherein the needle includes a third end configured for fluid communication with the second reservoir.

14. The method of claim 4, wherein the needle configured for fluid communication with the first reservoir is a first needle, the fluid delivery device further comprising a second needle configured for fluid communication with the second reservoir.

15. A method of administering first and second medicaments from a fluid delivery device, the method comprising:
   delivering a first basal delivery of the first medicament, and delivering a second basal delivery of the second medicament,
   wherein the fluid delivery device comprises:
      a housing;
      a first reservoir within the housing and configured to contain the first medicament;
      a second reservoir within the housing and configured to contain the second medicament;
      a basal drive mechanism within the housing and having a hydraulic fluid reservoir;
      a first pump chamber in fluid communication with the hydraulic fluid reservoir of the basal drive mechanism via a first flow restrictor, the first pump chamber configured to engage the first reservoir to provide basal delivery of the first medicament during use; and
      a second pump chamber in fluid communication with the hydraulic fluid reservoir of the basal drive mechanism via a second flow restrictor, the second pump chamber configured to engage the second reservoir to provide basal delivery of the second medicaments during use.

16. The method of claim 15, wherein the fluid delivery device further comprises a bolus drive mechanism coupled to the first and second pump chambers to provide bolus deliveries of the first and second medicaments.

17. The method of claim 16, wherein the bolus drive mechanism includes a ratchet and piston.

18. The method of claim 16, wherein the bolus of the first medicament is larger than the bolus of the second medicament.

19. The method of claim 15, wherein the fluid delivery device further comprises a first bolus drive mechanism coupled to the first pump chamber to provide a bolus delivery of the first medicament and a second bolus drive mechanism coupled to the second pump chamber to provide a bolus delivery of the second medicament.

20. The method of claim 15, wherein the fluid delivery device further comprises a needle having a first end configured for fluid communication with the first reservoir, a second end configured for fluid communication with the second reservoir and a third end configured to engage a user.

21. The method of claim 15, wherein the fluid delivery device further comprises a first needle configured for fluid communication with the first reservoir and a user and a second needle configured for fluid communication with the second reservoir and the user.

22. The method of claim 15, wherein the fluid delivery device is an ambulatory infusion pump.

* * * * *